(12) United States Patent
Wyman et al.

(10) Patent No.: US 12,109,235 B2
(45) Date of Patent: Oct. 8, 2024

(54) TGF-BETA RECEPTORS AND METHODS OF USE

(71) Applicant: Kite Pharma, Inc., Santa Monica, CA (US)

(72) Inventors: Sarah Wyman, Oakland, CA (US); Peter Emtage, Lafayette, CA (US); Gabrielle Romain, Berkeley, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 376 days.

(21) Appl. No.: 16/946,388

(22) Filed: Jun. 19, 2020

(65) Prior Publication Data

US 2020/0397823 A1    Dec. 24, 2020

Related U.S. Application Data

(60) Provisional application No. 62/951,217, filed on Dec. 20, 2019, provisional application No. 62/865,063, filed on Jun. 21, 2019.

(51) Int. Cl.
*A61K 38/00* (2006.01)
*A61K 35/17* (2015.01)
*A61P 35/00* (2006.01)
*C07K 14/71* (2006.01)
*C07K 14/725* (2006.01)

(52) U.S. Cl.
CPC .............. *A61K 35/17* (2013.01); *A61P 35/00* (2018.01); *C07K 14/7051* (2013.01); *C07K 14/71* (2013.01)

(58) Field of Classification Search
CPC ......... A61K 35/17; A61K 38/00; A61P 35/00; C07K 14/71; C07K 14/495; C07K 2319/00; C07K 2319/03; C07K 14/7051
See application file for complete search history.

(56) References Cited

U.S. PATENT DOCUMENTS

| | | | |
|---|---|---|---|
| 5,219,740 A | 6/1993 | Miller et al. | |
| 6,207,453 B1 | 3/2001 | Maass et al. | |
| 8,993,524 B2 * | 3/2015 | Bedi .................. | C07K 14/495 514/19.2 |
| 9,926,377 B2 | 3/2018 | Polakis et al. | |
| 2003/0125251 A1 | 7/2003 | Wakefield et al. | |
| 2018/0066057 A1 | 3/2018 | Govindappa et al. | |
| 2019/0151362 A1 | 5/2019 | Li et al. | |
| 2020/0002402 A1 | 1/2020 | Emtage et al. | |
| 2023/0020993 A1 | 1/2023 | Drever et al. | |

FOREIGN PATENT DOCUMENTS

| | | |
|---|---|---|
| CN | 105949324 A | 9/2016 |
| EP | 3569709 A1 | 11/2019 |
| EP | 3615574 A1 | 3/2020 |
| WO | 9309228 A1 | 5/1993 |
| WO | 9409815 A1 | 5/1994 |
| WO | 03000883 A1 | 1/2003 |
| WO | 04022597 A1 | 3/2004 |
| WO | 11109789 A2 | 9/2011 |
| WO | 12145469 A1 | 10/2012 |
| WO | 13070468 A1 | 5/2013 |
| WO | 13181543 A1 | 12/2013 |
| WO | 2014127261 A1 | 8/2014 |
| WO | 2014134165 A1 | 9/2014 |
| WO | 14180306 A1 | 11/2014 |
| WO | 15027082 A1 | 2/2015 |
| WO | 2015142675 A2 | 9/2015 |
| WO | 2015150526 A2 | 10/2015 |
| WO | 2015179658 A2 | 11/2015 |
| WO | 16036973 A1 | 3/2016 |
| WO | 16049459 A1 | 3/2016 |
| WO | 16113203 A1 | 7/2016 |
| WO | 16115482 A1 | 7/2016 |
| WO | 2017196847 A1 | 11/2017 |
| WO | 18018958 A1 | 2/2018 |
| WO | 2018038945 A1 | 3/2018 |
| WO | 2018044866 A1 | 3/2018 |
| WO | 2018111763 A1 | 6/2018 |
| WO | 18131586 A1 | 7/2018 |
| WO | 18200586 A1 | 11/2018 |
| WO | 18204594 A1 | 11/2018 |
| WO | 19094482 A1 | 5/2019 |
| WO | 2019109980 A1 | 6/2019 |
| WO | 2020190217 A2 | 9/2020 |
| WO | 2021110095 A1 | 6/2021 |

OTHER PUBLICATIONS

UniProt A0A213SZG2, pp. 1-6. Accessed on Oct. 27, 2022. (Year: 2022).*
Office Action, issued in TW Application No. 108121854, dated Nov. 3, 2020.
Yu et al., "Development of GPC3-Specific Chimeric Antigen Receptor-Engineered Natural Killer Cells for the Treatment of Hepatocellular Carcinoma," Molecular Therapy, vol. 26, No. 2, (2017), pp. 366-378.
International Search Report, issued in PCT/US2020/070157, dated Jan. 18, 2021.
Barrett et al., "Chimeric antigen receptor therapy for cancer", Annu Rev Med (2014) 65:333-47.
Cheadle et al., "CART cells: driving the road from the laboratory to the clinic", Immunol Rev (2014) 257(1):91-106.
Fedorov et al., "PD-1- and CTLA-4-based inhibitory chimeric antigen receptors (iCARs) divert off-target immunotherapy responses", Sci Transl Med (2013) 5(215):215ra172.
Glienke et al., "Advantages and applications of CAR-expressing natural killer cells", Front Pharmacol (2015) 6:21.
Kakarla et al., "CART cells for solid tumors: armed and ready to go?", Cancer J (2014) 20(2):151-5.
Palmer et al., "Interleukin-? receptor signaling network: an integrated systems perspective", Cell. Mol. Immunol. 5(2):79-89, 2008.

(Continued)

*Primary Examiner* — Julie Ha
(74) *Attorney, Agent, or Firm* — Barnes & Thornburg LLP

(57) ABSTRACT

Provided herein are engineered receptors involved in cytokine signaling. Also provided herein are engineered receptors for modulating TGF-β signaling, methods of modulating TGF-β signaling and treating cancer using chimeric antigen receptors.

11 Claims, 1 Drawing Sheet

Specification includes a Sequence Listing.

(56) References Cited

OTHER PUBLICATIONS

Pegram et al., "CD28z CARs and armored CARs, " Cancer J (2014) 20(2):127-33.
Riddell et al., "Adoptive therapy with chimeric antigen receptor-modified T cells of defined subset composition," Cancer J (2014) 20(2):141-4.
Chen et al., "Molecular mechanisms ofT cell co-stimulation and co-inhibition", Nature Reviews Immunol. 13:227-242, 2013.
Sadelain et al., "The basic principles of chimeric antigen receptor design", Cancer Discov (2013) 3(4):388-98.
Cartellieri et al., "Chimeric antigen receptor-engineered T cells for immunotherapy of cancer" J Biomed Biotechnol (2010) 956304.
Kershaw et al., "Supernatural T cells: genetic modification of T cells for cancer therapy", Nature Reviews Immunol. 5(12):928-940, 2005.
Eshhar et al.,"Specific activation and targeting of cytotoxic lymphocytes through chimeric single chains consisting of antibody-binding domains and the gamma or zeta subunits of the immunoolobulin and T-cell receptors" Proc. Natl. Acad. Sci. U.S.A. 90(2):720-724, 1993.
Sadelain et al.,"The promise and potential pitfalls of chimeric antigen receptors.", Curr. Opin. Immunol. 21(2): 215-223, 2009.
Ranganathan, "Pinpointing the putative heparin/sialic acid-binding residues in the 'sushi' domain 7 of factor H: a molecular modeling study", Pac. Symp Biocomput. 20 2000:155-67.
Carlens et al., "Ex vivo T lymphocyte expansion for retroviral transduction", Exp. Hematol. 28(10):1137-1146, 2000.
Park et al., "Treating cancer with genetically engineered T cells", Trends Biotechnol. 29(11):550-557,2011.
Alonso-Camino et al., "CARbodies: Human Antibodies Against Cell Surface Tumor Antigens Selected From Repertoires Displayed on T Cell Chimeric Antigen Receptors" Mol. Ther. Nucleic Acids 2:e93, 2013.
Miller et al., "Improved retroviral vectors for gene transfer and expression", BioTechniques 7:980-990, 1989.
Miller, "Retrovirus packaging cells" Human Gene Therapy 1:5-14, 25 1990.
Scarpa et al., "Characterization of recombinant helper retroviruses from Moloney-based vectors in ecotropic and amphotropic packaging cell lines." Virology 180:849-852, 1991.
Burns et al., "Vesicular stomatitis virus G glycoprotein pseudotyped retroviral vectors: concentration to very high titer and efficient gene transfer into mammalian and nonmammalian cells" Proc. Natl. Acad. Sci. U.S.A. 90:8033-8037, 1993.
Boris-Lawrie et al., "Recent Advances in Retrovirus Vector Technology", Cur. Opin. Genet. Develop. 3:102-109, 1993.
Wang et al., "Phenotypic and Functional Attributes of Lentivirus Modified CD19-specific Human CDS+ Central Memory T Cells Manufactured at Clinical Scale", J. Immunother. 35(9):689-701, 2003.
Cooper et al., "T-cell clones can be rendered specific for CD19: toward the selective augmentation of the graft-versus-B-lineage leukemia effect", Blood 101:1637-1644, 2003.
Verhoeyen et al., "Lentiviral vector gene transfer into human T cells", Methods Mol. Biol. 506:97-114, 2009.
Cavalieri et al., "Human T lymphocytes transduced by lentiviral vectors in the absence of TCR activation maintain an intact immune competence", Blood 30 102(2):497-505, 2003.
Gao et al., Clin Cancer Res. 20(24):6418-28 (2014).
Li et al., Hum Gene Ther. 28(5):437-48 (2017).
Wieser et al., Molecular and Cellular Biology 13(12): 7239-7247 (1993).
Bollard et al., Blood. 99(9):3179-3187 (2002).
Kloss, Christopher C., et al. "Dominant-negative TGF-β receptor enhances PSMA-targeted human CAR T cell proliferation and augments prostate cancer eradication." Molecular therapy 26.7 (2018): 1855-1866.
Zhai, Bo, et al. "A phase I study of anti-GPC3 chimeric antigen receptor modified T cells (GPC3 CAR-T) in Chinese patients with refractory or relapsed GPC3+ hepatocellular carcinoma (r/r GPC3+ HCC)." (2017): 3049-3049.
Bendle, Gavin M., et al. "Blockade of TGF-β signaling greatly enhances the efficacy of TCR gene therapy of cancer." The Journal of Immunology 191.6 (2013): 3232-3239.
Ishiguro, Takahiro, et al. "Anti-glypican 3 antibody as a potential antitumor agent for human liver cancer." Cancer research 68.23 (2008): 9832-9838.
Phung, Yen, et al. "High-affinity monoclonal antibodies to cell surface tumor antigen glypican-3 generated through a combination of peptide immunization and flow cytometry screening." MAbs. vol. 4. No. 5. Taylor & Francis, 2012.
Vong, Queenie, et al. "Inhibiting TGFβ signaling in CAR T-cells may significantly enhance efficacy of tumor immunotherapy." Blood 130 (2017): 1791.
Zhang, Yi-Fan, and Mitchell Ho. "Humanization of high-affinity antibodies targeting glypican-3 in hepatocellular carcinoma." Scientific reports 6.1 (2016): 1-11.
Jul. 25, 2019 (Jul. 25, 2019), "IL2RG fusion protein, SEQ ID 27.", retrieved from EBI accession No. GSP:BGL03586 Database accession No. BGL03586 sequence & DATABASE Geneseq [Online].
Jul. 25, 2019 (Jul. 25, 2019), "Human TGF-beta receptor I protein extracellular domain, SEQ ID 4.", retrieved from EBI accession No. GSP:BGL03563 Database accession No. BGL03563 Sequence.
Aug. 9, 2018 (Aug. 9, 2018), "Dominant negative TGFB-RII protein, SEQ ID 97.", retrieved from EBI accession No. GSP:BFK39104 Database accession No. BFK39104 Sequence.
May 3, 2018 (May 3, 2018), "Cixutumumab light chain-TGF-beta RII ECO fusion protein.", retrieved from EBI accession No. GSP:BFD37600 Database accession No. BFD37600 Sequence.
Hurton Lenka V., et al. "Tethered IL-15 augments antitumor activity and promotes a stem-cell memory subset in tumor-specific T cells." Proceedings of the National Academy of Sciences, Nov. 14, 2016, p. E7788-E7797, vol. 113, No. 48.
Shochat Chen, et al. "Novel activating mutations lacking cysteine in type I cytokine receptors in acute lymphoblastic leukemia." Blood, The Journal of the American Society of Hematology, Jul. 3, 2014, p. 106-110, vol. 124, No. 1.

* cited by examiner

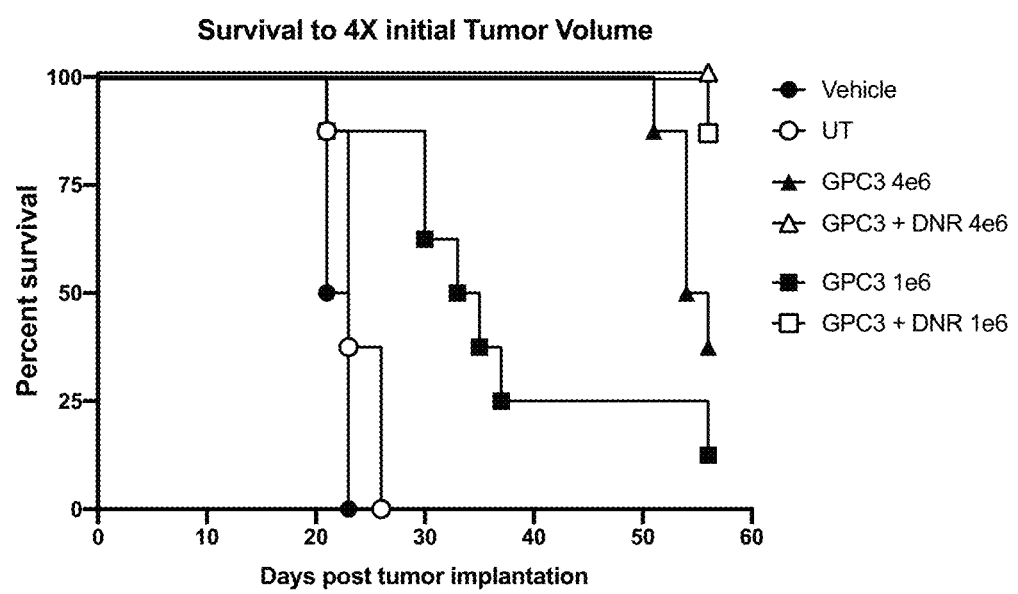

TGF-BETA RECEPTORS AND METHODS OF USE

CROSS-REFERENCE FOR RELATED APPLICATIONS

This application claims priority to U.S. Provisional Patent Application No. 62/865,063 filed Jun. 21, 2019, and to U.S. Provisional Patent Application No. 62/951,217 filed Dec. 20, 2019, both of which are incorporated by reference herein in their entirety.

STATEMENT REGARDING SEQUENCE LISTING

The Sequence Listing associated with this application is provided in text format in lieu of paper copy, and is hereby incorporated by reference into the specification. The name of the text file containing the Sequence Listing is "K1075_ST25." The text file is 109 KB, was created on Jun. 17, 2020, and is being submitted electronically via EFS-Web, concurrent with the filing of this specification.

BACKGROUND

Technical Field

The present disclosure relates to engineered receptors involved in TGF-β signaling. The disclosure also relates to engineered TGF-β receptors for modulating TGF-β signaling and methods of modulating TGF-β signaling, cytokine signaling and treating cancers.

Description of the Related Art

Transforming growth factor β (TGF-β) is a pleotropic immunosuppressive molecule secreted by many cell types that limits both the function and expansion of effector T cells. Clinical and pre-clinical data has suggested that tumor cells, stromal cells, and suppressive immune subsets including regulatory T cells secrete TGF-β, and many groups report that TGF-β inhibits effector T cell function and proliferation in the tumor microenvironment (TME) (Thomas et al., *Cancer Cell*, 8(5):369-380 (2005), Yang et al., *Trends in Immunology*, 31(6) (2010), and Pickup et al., *Nat Rev Cancer*, 13(11), 788-799 (2013)).

The TGF-β signaling pathway begins with endogenous expression of two, dimeric, transmembrane Transforming Growth Factor-β protein receptors: TGF-β Receptor Type I (TGF-βRI) and TGF-β Receptor Type II (TGF-βRII) (collectively "TGF-β Receptors"). In T cells, TGF-βRII is constitutively phosphorylated. Upon TGF-β ligand binding, two molecules each of TGF-βRI and TGF-βRII form a hetero-tetramer receptor complex that induces TGF-βRII trans-phosphorylation of TGF-βRI at four key threonine sites between amino acids (aa) 185-205 of the TGF-βRI protein (Heldin et al., *Cold Spring Harb Perspect Biol*. August 1:8(8) (2016)). Phosphorylated TGF-βRI then initiates phosphorylation of a set of receptor regulated signal transducing proteins: SMAD2 and SMAD3. Both pSMAD2 and pSMAD3 form hetero-trimeric oligomers with pSMAD4. The resulting activated SMAD complex then enters the nucleus and docks at target transcription factor binding sites to induce expression of target genes that support immunosuppression (Inman et al., *Mol Cell*, 10(2): 283-294 (2002)).

Some studies have attempted to limit the immunosuppressive effects of TGF-β on effector T cell function. These include the use of small molecule and antibody-based inhibitors of TGF-β binding and the TGF-β signaling pathway (Fabregat et al., *Current Pharmaceutical Design*, 20, 1-14 (2014)). Also, T cell receptor (TCR) constructs with modified TGF-β receptor molecules have been used. One example is a truncated form of TGF-βRII, in which the intracellular portion of the Type II receptor was removed, thus preventing downstream signaling events and thereby acting as a dominant-negative inhibitor of the TGF-β signaling pathway in engineered T cells (Wieser et al., *Molecular and Cellular Biology* 13(12): 7239-7247 (1993) and Bollard et al., *Blood*. 99(9):3179-3187 (2002)). Nonetheless, there are no effective treatments based solely on TGF-β inhibition and several systemic therapies have dose limiting toxicity. Accordingly, there is a need to develop new modalities for inhibiting TGF-β.

SUMMARY

One embodiment of the disclosure is a recombinant polypeptide comprising an extracellular domain (ECD) from a TGF-β receptor and a transmembrane domain (TMD), wherein the recombinant polypeptide lacks amino acid residues responsible for signaling and phosphorylation present in a wild-type TGF-β receptor.

In one aspect, the ECD is selected from TGF-βRI or TGF-βRII. In another aspect, the TMD is selected from TGF-βRI, PDGFR, CD4, CD8, CD28, CD127, CD132, CD3ζ, 4-1BB, OX40, ICOS, CTLA-4, PD-1, LAG-3, 2B4, IL-5, IL-7, IL-7Rα, BTLA, or mutants of any of the foregoing. In another aspect, the polypeptide further comprises a heterologous intracellular domain (ICD) which lacks amino acid residues responsible for signaling and phosphorylation present in wild-type TGF-β receptor. In yet another aspect, the polypeptide further comprises a signal sequence.

In one aspect, the ECD comprises the amino acid sequence having at least 75% sequence identity to SEQ ID NO: 15 and the TMD comprises the amino acid sequence having at least 75% sequence identity to SEQ ID NO: 16. In another aspect, the ICD comprises the amino acid sequence having at least 75% sequence identity to SEQ ID NO: 6. In one aspect, the polypeptide comprises the amino acid sequence having at least 75% sequence identity to SEQ ID NO: 14.

In one aspect the polypeptide binds TGF-β1.

Another aspect of the disclosure is an expression vector comprising a nucleic acid encoding the polypeptide described herein. In another aspect, the expression vector further comprises a nucleic acid sequence encoding a chimeric antigen receptor (CAR). In yet another aspect, the CAR binds to a tumor antigen comprising CD19, PSMA or GPC3.

Another aspect of the disclosure is a T cell transduced with the expression vectors described herein.

Another aspect of the disclosure is a method of treating cancer comprising administering to a subject in need thereof a therapeutically effective amount of the T cell described herein.

In another embodiment of the disclosure, is a recombinant nucleotide encoding a chimeric antigen receptor (CAR) comprising the nucleotide sequence of SEQ ID NO: 51. In one aspect, the recombinant nucleic acid further comprises the nucleotide sequence of SEQ ID NO: 48. In another aspect, the recombinant nucleic acid sequence encodes a polypeptide of SEQ ID NO: 47. In another aspect of the disclosure is an expression vector comprising the nucleic acid encoding the polypeptides described herein.

In another aspect, the CAR binds to a tumor antigen comprising GPC3. Another aspect of the disclosure is a T cell transduced with the expression vectors described herein.

Another aspect of the disclosure is a method of treating hepatic cancer comprising administering to a subject in need thereof a therapeutically effective amount of the T cell described herein.

BRIEF DESCRIPTION OF THE DRAWINGS

FIG. 1: Long-term efficacy and tumor growth delay was determined by progression towards survival to a tumor volume endpoint set at four-fold the initial volume.

DETAILED DESCRIPTION

The present disclosure relates to engineered receptors for modulating TGF-β signaling and methods of modulating TGF-β signaling. In certain aspects, the disclosure relates to an engineered receptor that may function as a dominant negative inhibitor which may be useful for modulating TGF-β activities. In some aspects, the disclosure relates to dominant-negative TGF-β Receptors, including TGF-β Type I (TGF-βRI) or TGF-β Type II (TGF-βRII), for inhibiting TGF-β activity. In one aspect, the disclosure relates to the use of dominant negative TGF-β Receptors for treating diseases or disorders, such as in T cell immunotherapies. In another aspect, the disclosure relates to the use of dominant negative TGF-β Receptors to stimulate cytokine signaling that may enhance T cell function in the TME. In yet another aspect, the disclosure relates to the use of dominant negative TGF-β Receptors in combination with other immunotherapies.

Definitions

Unless otherwise defined, all technical and scientific terms used herein have the same meaning as commonly understood by one of ordinary skill in the art. In case of conflict, the present document, including definitions, will control. Methods and materials are described below, although methods and materials similar or equivalent to those described herein may be used in practice or testing of the present disclosure. All publications, patent applications, patents and other references mentioned herein are incorporated by reference in their entirety. The materials, methods, and examples disclosed herein are illustrative only and not intended to be limiting.

The articles "a," "an," and "the" refer to one or to more than one (i.e., to at least one) of the grammatical object of the article. By way of example, "an element" can mean one element or more than one element.

As used herein, the term "about" or "approximately" refers to a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In some embodiments, the terms "about" or "approximately" when preceding a numerical value indicates the value plus or minus a range of 15%, 10%, 5%, or 1%.

The terms, "activated" and "activation" refer to the state of a T cell that has been sufficiently stimulated to induce detectable cellular proliferation. In one embodiment, activation may also be associated with induced cytokine production, and detectable effector functions. The term "activated T cells" refers to, among other things, T cells that are proliferating. Signals generated through the TCR alone may be insufficient for full activation of the T cell and one or more secondary or costimulatory signals may also be required. Thus, T cell activation comprises a primary stimulation signal through the TCR/CD3 complex and one or more secondary costimulatory signals. Costimulation may be evidenced by proliferation and/or cytokine production by T cells that have received a primary activation signal, such as stimulation through the TCR/CD3 complex.

Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, administration is via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "amount" refers to "an amount effective" or "therapeutically effective amount" of an agent, such as a genetically modified therapeutic cell, e.g., T cell, to achieve a beneficial or desired prophylactic or therapeutic result, including clinical results. A "therapeutically effective amount" of a genetically modified therapeutic cell may vary according to factors such as the disease state, age, sex, and weight of the individual, and the ability of the T cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient). When a therapeutic amount is indicated, the precise amount of the compositions of the present disclosure to be administered may be determined by a physician with consideration of individual differences in age, weight, tumor size, extent of infection or metastasis, and condition of the patient (subject).

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system. In general, human antibodies are approximately 150 kD tetrameric agents composed of two identical heavy (H) chain polypeptides (about 50 kD each) and two identical light (L) chain polypeptides (about 25 kD each) that associate with each other into what is commonly referred to as a "Y-shaped" structure. The heavy and light chains are linked or connected to one another by a single disulfide bond; two other disulfide bonds connect the heavy chain hinge regions to one another, so that the dimers are connected to one another and the tetramer is formed. Naturally-produced antibodies are also glycosylated, e.g., on the CH2 domain.

The term "human antibody" is intended to comprise antibodies having variable and constant domain sequences generated, assembled, or derived from human immunoglobulin sequences, or sequences indistinguishable therefrom. In some embodiments, antibodies (or antibody components) may be considered to be "human" even though their amino acid sequences comprise residues or elements not encoded by human germline immunoglobulin sequences (e.g., variations introduced by in vitro random or site-specific mutagenesis or introduced by in vivo somatic mutation). The term "humanized" is intended to comprise antibodies having a variable domain with a sequence derived from a variable domain of a non-human species (e.g., a mouse), modified to be more similar to a human germline encoded sequence. In some embodiments, a "humanized" antibody comprises one or more framework domains having substantially the amino acid sequence of a human framework domain, and one or more complementary determining regions having substantially the amino acid sequence as that of a non-human antibody. In some embodiments, a humanized antibody comprises at least a portion of an immunoglobulin constant region (Fc), generally that of a human immunoglobulin constant domain. In some embodiments, a humanized antibodies may comprise a $C_H1$, hinge, $C_H2$, $C_H3$, and, optionally, a $C_H4$ region of a human heavy chain constant domain.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a mouse. In some embodiments, a CAR contemplated herein comprises an antigen-specific binding domain that is a chimeric antibody or antigen binding fragment thereof.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen binding fragments of any of the above. In certain embodiments, antibodies described herein refer to polyclonal antibody populations. Antibodies may also comprise, for example, Fab' fragments, Fd' fragments, Fd fragments, isolated CDRs, single chain Fvs, polypeptide-Fc fusions, single domain antibodies (e.g., shark single domain antibodies such as IgNAR or fragments thereof), camelid antibodies, single chain or Tandem diabodies (TandAb®), Anticalins®, Nanobodies® minibodies, BiTE®s, ankyrin repeat proteins or DARPINs®, Avimers®, DARTs, TCR-like antibodies, Adnectins®, Affilins®, Transbodies®, Affibodies®, TrimerX®, MicroProteins, Fynomers®, Centyrins®, and KALBITOR®s.

An immunoglobulin may derive from any of the commonly known isotypes, including but not limited to IgA, secretory IgA, IgG, IgE and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or non-human Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen binding fragment or an antigen-binding portion of any of the aforementioned immunoglobulins, and includes a monovalent and a divalent fragment or portion, and a single chain Ab.

An "antigen binding molecule," "antigen binding portion," or "antibody fragment" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

In some instances, a CDR is substantially identical to one found in a reference antibody and/or the sequence of a CDR provided in the present disclosure. In some embodiments, a CDR is substantially identical to a reference CDR (e.g., a CDR provided in the present disclosure) in that it is either identical in sequence or contains between 1, 2, 3, 4, or 5 (e.g. 1-5) amino acid substitutions as compared with the reference CDR. In some embodiments a CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR (e.g., 85-90%, 85-95%, 85-100%, 90-95%, 90-100%, or 95-100%). In some embodiments a CDR is substantially identical to a reference CDR in that it shows at least 96%, 96%, 97%, 98%, 99%, or 100% sequence identity with the reference CDR. In some embodiments a CDR is substantially identical to a reference CDR in that one amino acid within the CDR is deleted, added, or substituted as compared with the reference CDR while the CDR has an amino acid sequence that is otherwise identical with that of the reference CDR. In some embodiments a CDR is substantially identical to a reference CDR in that 2, 3, 4, or 5 (e.g. 2-5) amino acids within the CDR are deleted, added, or substituted as compared with the reference CDR while the CDR has an amino acid sequence that is otherwise identical to the reference CDR. In various embodiments, an antigen binding fragment binds a same antigen as a reference antibody.

An antigen binding fragment may be produced by any means. For example, in some embodiments, an antigen binding fragment may be enzymatically or chemically produced by fragmentation of an intact antibody. In some embodiments, an antigen binding fragment may be recombinantly produced (i.e., by expression of an engineered nucleic acid sequence. In some embodiments, an antigen binding fragment may be wholly or partially synthetically produced. In some embodiments, an antigen binding fragment may have a length of at least about 50, 60, 70, 80, 90, 100, 110, 120, 130, 140, 150, 160, 170, 180, 190 amino acids or more; in some embodiments at least about 200 amino acids (e.g., 50-100, 50-150, 50-200, or 100-200 amino acids).

The term "variable region" or "variable domain" is used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

References to "VH" or "$V_H$" refer to the variable region of an immunoglobulin heavy chain, including that of an antibody, Fv, scFv, dsFv, Fab, or other antibody fragment as disclosed herein. References to "VL" or "$V_L$" refer to the variable region of an immunoglobulin light chain, including that of an antibody, Fv, scFv, dsFv, Fab, or other antibody fragment as disclosed herein.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

CDR Numbering

| Loop | Kabat | AbM | Chothia | Contact |
|---|---|---|---|---|
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 | H31-H35B (Kabat Numbering) | H26-H35B | H26-H32 . . . 34 | H30-H35B |
| H1 | H31-H35 (Chothia Numbering) | H26-H35 | H26-H32 | H30-H35 |
| H2 | H50-H65 | H50-H58 | H52-H56 | H47-H58 |
| H3 | H95-H102 | H95-H102 | H95-H102 | H93-H101 |

The term "Kabat numbering" and like terms are recognized in the art and refer to a system of numbering amino acid residues in the heavy and light chain variable regions of an antibody, or an antigen-binding molecule thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), *J Mol Biol* 196: 901-917; Al-Lazikani B et al., (1997) *J Mol Biol* 273: 927-948; Chothia C et al., (1992) *J Mol Biol* 227: 799-817; Tramontano A et al., (1990) *J Mol Biol* 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

The terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

The term "heavy chain" when used in reference to an antibody can refer to any distinct type, e.g., alpha (α), delta (Δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

The term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

The term "antigen (Ag)" refers to a compound, composition, or substance that may stimulate the production of antibodies or a T cell response in a human or animal, including compositions (such as one that includes a tumor-specific protein) that are injected or absorbed into a human or animal. An antigen reacts with the products of specific humoral or cellular immunity, including those induced by heterologous antigens, such as the disclosed antigens. A "target antigen" or "target antigen of interest" is an antigen that is not substantially found on the surface of other normal (desired) cells and to which a binding domain of a TCR or CAR contemplated herein, is designed to bind. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens. A "target" is any molecule bound by a binding motif, antigen binding system, or binding agent, e.g., an antibody. In some embodiments, a target is an antigen or epitope of the present disclosure.

The term "cancer" relates generally to a class of diseases or conditions in which abnormal cells divide without control and may invade nearby tissues. Examples of cancers that can be treated by the methods of the present disclosure include, but are not limited to, cancers of the immune system including lymphoma, leukemia, myeloma, and other leukocyte malignancies. In some embodiments, the methods of the present disclosure can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In one particular embodiment, the cancer is multiple myeloma. The particular cancer can be responsive to chemo- or radiation therapy or the cancer can be refractory. A refractory cancer refers to a cancer that is not amendable to surgical intervention and the cancer is either initially unresponsive to chemo- or radiation therapy or the cancer becomes unresponsive over time. Cancer further includes relapsed or refractory large B-cell lymphoma after two or more lines of systemic therapy, including diffuse large B-cell lymphoma (DLBCL) not otherwise specified, primary mediastinal large B-cell lymphoma after two or more lines of systemic therapy, high grade B-cell lymphoma, and DLBCL arising from follicular lymphoma.

The term "cancerous cell," "cancer cell," "tumor cell" or variant thereof refers to an individual cell of a cancerous growth or tissue. A tumor refers generally to a swelling or lesion formed by an abnormal growth of cells, which may be benign, pre-malignant, or malignant. Most cancers form tumors, but some, e.g., leukemia, do not necessarily form tumors. For those cancers that form tumors, the terms cancer (cell) and tumor (cell) are used interchangeably. The amount of a tumor in an individual is the "tumor burden" which may be measured as the number, volume, or weight of the tumor. Unless the context requires otherwise, the words "comprise", "comprises" and "comprising" will be understood to imply the inclusion of a stated step or element or group of steps or elements but not the exclusion of any other step or element or group of steps or elements. By "consisting of" is meant to include, and be limited to, whatever follows the phrase "consisting of." Thus, the phrase "consisting of" indicates that the listed elements are required or mandatory, and that no other elements may be present. By "consisting essentially of" is meant including any elements listed after the phrase, and be limited to other elements that do not interfere with or contribute to the activity or action specified in the disclosure for the listed elements.

A "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding molecule thereof can be replaced with an amino acid residue with a similar side chain. In general, two sequences are generally considered to be "substantially similar" if they contain a conservative amino acid substitution in corresponding positions. For example, certain amino acids are generally classified as "hydrophobic" or "hydrophilic" amino acids, and/or as having "polar" or "non-polar" side chains. Substitution of one amino acid for another of the same type may be considered a conservative substitution. Exemplary amino acid categorizations are summarized in Tables 2 and 3 below:

TABLE 2

Exemplary Amino Acid Categorizations

| Amino Acid | 3-Letter | 1-Letter | Property | Property | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 3

Exemplary Amino Acid Categorizations

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

By "decrease" or "lower," or "lessen," or "reduce," or "abate" refers generally to the ability of a composition contemplated herein to produce, elicit, or cause a lesser physiological response (i.e., a downstream effect) compared to the response caused by either the vehicle alone (i.e., an active moiety) or a control molecule/composition. A "decrease" or "reduced" amount is typically a "statistically significant" amount, and may include an decrease that is 1.1, 1.2, 1.5, 2, 2.5, 3, 3.5, 4, 4.5, 5, 5.5, 6, 6.5, 7, 7.5, 8, 8.5, 9, 9.5, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition.

The term "dominant negative" refers to a truncation or mutation of a polypeptide coding sequence such that the altered gene product inhibits the downstream signaling function normally transmitted through the unmodified gene product.

The terms "enhance" or "promote," or "increase" or "expand" refers generally to the ability of a composition contemplated herein to produce, elicit, or cause a greater physiological response (e.g., downstream effects) compared to the response caused by either vehicle or a control molecule/composition. A measurable physiological response may include an increase in T cell expansion, activation, persistence, and/or an increase in cancer cell death killing ability, among others apparent from the understanding in the art and the description herein. An "increased" or "enhanced" amount is typically a "statistically significant" amount, and may include an increase that is 1.1, 1.2, 1.5, 2, 2.5, 3, 3.5, 4, 4.5, 5, 5.5, 6, 6.5, 7, 7.5, 8, 8.5, 9, 9.5, 10, 15, 20, 30 or more times (e.g., 500, 1000 times) (including all integers and decimal points in between and above 1, e.g., 1.5, 1.6, 1.7, 1.8, etc.) the response produced by vehicle or a control composition.

As used herein, the term "epitope" refers to a region of an antigen to which a binding agent binds. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) *Acta Crystallogr D Biol Crystallogr* 50(Pt 4): 339-350; McPherson A (1990) *Eur J Biochem* 189: 1-23; Chayen N E (1997) *Structure* 5: 1269-1274; McPherson A (1976) *J Biol Chem* 251: 6300-6303). Antibody:antigen crystals may be studied using well known X-ray diffraction techniques and may be refined using computer software such as X-PLOR (Yale University, 1992, distributed by Molecular Simulations, Inc.; see e.g. *Meth Enzymol* (1985) volumes 114 & 115, eds Wyckoff H W et al.; U.S. 2004/0014194), and BUSTER (Bricogne G (1993) *Acta Crystallogr D Biol Crystallogr* 49(Pt 1): 37-60; Bricogne G (1997) *Meth Enzymol* 276A: 361-423, ed Carter C W; Roversi P et al., (2000) *Acta Crystallogr D Biol Crystallogr* 56(Pt 10): 1316-1323). Mutagenesis mapping studies may be accomplished using any method known to one of skill in the art. See, e.g., Champe M et al., (1995) *J Biol Chem* 270: 1388-1394 and Cunningham B C & Wells J A (1989) *Science* 244: 1081-1085 for a description of mutagenesis techniques, including alanine scanning mutagenesis techniques.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome. Engineering generally comprises manipulation by the hand of man. For example, a polynucleotide is considered to be "engineered" when two or more sequences, that are not linked or connected together in that order in nature, are manipulated by the hand of man to be directly linked or connected to one another in the engineered polynucleotide. In the context of manipulation of cells by techniques of molecular biology, a cell or organism is considered to be "engineered" if it has been manipulated so that its genetic information is altered (e.g., new genetic material not previously present has been introduced, for example by transformation, somatic hybridization, transfection, transduction, or other mechanism, or previously present genetic material is altered or removed, for example by substitution or deletion mutation, or by other protocols). In some embodiments, a binding agent is a modified lymphocyte, e.g., a T cell, may be obtained from a patient or a donor. An engineered cell may be modified to express an exogenous construct, such as, e.g., a chimeric antigen receptor (CAR) or a T cell receptor (TCR), which is incorporated into the cell's genome. Progeny of an engineered polynucleotide or binding agent are generally referred to as "engineered" even though the actual manipulation was performed on a prior entity. In some embodiments, "engineered" refers to an entity that has been designed and produced. The term "designed" refers to an agent (i) whose structure is or was selected by the hand of man; (ii) that is produced by a process requiring the hand of man; and/or (iii) that is distinct from natural substances and other known agents. A "T cell receptor" or "TCR" refers to antigen-recognition molecules present on the surface of T-cells. During normal T-cell development, each of the four TCR genes, α, β, γ, and δ, may rearrange leading to highly diverse TCR proteins. The terms, "genetically modified cells," "modified cells," and, "redirected cells," are used interchangeably.

An "immune effector cell," is any cell of the immune system that has one or more effector functions (e.g., cytotoxic cell killing activity, secretion of cytokines, induction of ADCC and/or CDC). The illustrative immune effector cells contemplated herein are T lymphocytes, for example pan CD3$^+$ T cells, cytotoxic T cells (CTLs; CD8$^+$ T cells), TILs, and helper T cells (HTLs; CD4$^+$ T cells).

The terms "individual" and "subject" are often used interchangeably and refer to any animal that may be treated with the methods disclosed herein. Suitable subjects (e.g., patients) include laboratory animals (such as mouse, rat, rabbit, or guinea pig), farm animals, and domestic animals or pets (such as a cat or dog). Non-human primates and human patients, are included. In one embodiment, subjects may include human patients that have a cancer, have been diagnosed with a cancer, are suspected to have a cancer, or are at risk or having a cancer. As used herein, the term "patient" refers to a subject that may receive a treatment of a disease or condition.

The term "isolated peptide" or an "isolated polypeptide" and the like, refer to in vitro isolation and/or purification of a peptide or polypeptide molecule from a cellular environment, and from association with other components of the cell, i.e., it is not significantly associated with in vivo substances. Similarly, an "isolated cell" refers to a cell that has been obtained from an in vivo tissue or organ and is substantially free of extracellular matrix.

The term "isolated polynucleotide" refers to a polynucleotide that has been purified from the sequences which flank it in a naturally-occurring state, e.g., a DNA fragment that has been removed from the sequences that are normally adjacent to the fragment. An "isolated polynucleotide" also refers to a complementary DNA (cDNA), a recombinant DNA, or other polynucleotide that does not exist in nature and that has been made by the hand of man.

The term "lymphocyte" includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4$^+$ cells), Cytotoxic T-cells (also known as TC, cytotoxic T lymphocyte, CTL, T-killer cell, cytolytic T cell, CD8$^+$ T-cells or killer T cell), Memory T-cells ((i) stem memory $T_{SCM}$ cells, like naive cells, are CD45RO$^-$, CCR7$^+$, CD45RA$^+$, CD62L$^+$ (L-selectin), CD27$^+$, CD28$^+$ and IL-7Re, but they also express large amounts of CD95, IL-2R13, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4$^+$ CD25$^+$ regulatory T cells), Natural Killer T-cells (NKT) and Gamma Delta T-cells. T cell is intended to include gamma delta T cells, pan CD3$^+$ T cells, including thymocytes, naive T lymphocytes, immature T lymphocytes, mature T lymphocytes, resting T lymphocytes, or activated T lymphocytes. A T cell may be a T helper (Th) cell, for example a T helper 1 (Th1) or a T helper 2 (Th2) cell. The T cell may be a helper T cell (HTL; CD4$^+$ T cell) CD4$^+$ T cell, a cytotoxic T cell (CTL; CD8$^+$ T cell), a tumor infiltrating cytotoxic T cell (TIL; CD8$^+$ T cell), CD4$^+$ CD8$^+$ T cell, CD4$^-$CD8$^-$ T cell, or any other subset of T cells. Other illustrative populations of T cells suitable for use in some embodiments include naive T cells and memory T cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "modified T cells" refer to T cells that have been modified by the introduction of a polynucleotide encoding an engineered polypeptide as described herein. Modified T cells include both genetic and non-genetic modifications (e.g., episomal or extrachromosomal). In one embodiment, the modified T cells may include a TGF-β receptor or a CAR-DN TGF-β Receptor as described herein.

By "maintain," or "preserve," or "maintenance," or "no change," or "no substantial change," or "no substantial decrease" refers generally to the ability of a composition contemplated herein to produce, elicit, or cause a lesser physiological response (i.e., downstream effect) in a cell, as compared to the response caused by either vehicle, a control molecule/composition. A comparable response is one that is not significantly different or measurably different from the reference response.

The term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primacy) tumor. As used herein, the term "benign" or "non-malignant" refers to tumors that may grow larger but do not spread to other parts of the body. Benign tumors are self-limited and typically do not invade or metastasize.

The term "proliferation" refers to an increase in cell division, either symmetric or asymmetric division of cells. In some embodiments, "proliferation" refers to the symmetric or asymmetric division of T cells. "Increased proliferation" occurs when there is an increase in the number of cells in a treated sample compared to cells in a non-treated sample.

The term "stimulation" refers to a primary response induced by binding of a stimulatory molecule (e.g., a TCR/CD3 complex) with its cognate ligand thereby mediating a signal transduction event including, but not limited to, signal transduction via the TCR/CD3 complex. A "stimulatory molecule," refers to a molecule on a T cell that specifically binds with a cognate stimulatory ligand. A "stimulatory ligand," as used herein, means a ligand that when present on an antigen presenting cell (APC) (e.g., a dendritic cell, a B-cell, and the like) may specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands include, but are not limited to CD3 ligands, e.g., an anti-CD3 antibody (such as OKT3) and CD2 ligands, e.g., anti-CD2 antibody, peptides, e.g., Cytomegalovirus (CMV), Hepatitis B virus (HBV), and Epstein-Barr virus (EBV) peptides, an MHC Class I molecule loaded with a peptide, a superagonist ant-CD2 antibody, and a superagonist anti-CD28 antibody.

A "co-stimulatory signal," refers to a signal, which in combination with a primary signal, such as TCR/CD3 ligation, leads to T cell proliferation, cytokine production, and/or upregulation or downregulation of molecules (e.g., CD28).

A "co-stimulatory ligand" as used herein, includes a molecule on an antigen presenting cell that specifically binds a cognate co-stimulatory molecule on a T cell. Binding of the co-stimulatory ligand provides a signal that mediates a T cell response, including, but not limited to, proliferation, activation, differentiation, and the like. A co-stimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

[1] A "co-stimulatory molecule" is a cognate binding partner on a T cell that specifically binds with a co-stimulatory ligand, thereby mediating a co-stimulatory response by the T cell, such as, but not limited to, proliferation. Co-stimulatory molecules include, but are not limited to, A "co-stimulatory molecule" is a cognate binding partner on a T cell that specifically binds with a co-stimulatory ligand, thereby mediating a co-stimulatory response by the T cell, such as, but not limited to, proliferation. Co-stimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CD5, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL-2R beta, IL-2R gamma, IL-7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher of a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment may involve optionally either the reduction or amelioration of symptoms of the disease or condition, or the delaying of the progression of the disease or condition. "Treatment" does not necessarily indicate complete eradication or cure of the disease or condition, or associated symptoms thereof.

The term "viral induced cancer" includes any malignancy induced by either DNA or RNA viruses. Such viruses may include, but are not limited to, for example: Cytomegalovirus (CMV), Hepatitis B virus (HBV-liver cell carcinoma), Human papillomavirus (HPV-squamous cell carcinoma, cervical carcinoma), Human T-lymphotropic virus (HTLV-I-adult T-cell leukemia), and Epstein-Barr virus (EBV-Burkitt's lymphoma, nasopharyngeal carcinoma).

"Chimeric antigen receptor" or "CAR" refers to a molecule engineered to comprise a binding motif and a means of activating immune cells (for example T cells such as naive T cells, central memory T cells, effector memory T cells or combination thereof) upon antigen binding. CARs are also known as artificial T cell receptors, chimeric T cell receptors or chimeric immunoreceptors. In some embodiments, a CAR comprises a binding motif, an extracellular domain, a transmembrane domain, one or more co-stimulatory domains, and an intracellular signaling domain. A T cell that has been genetically engineered to express a chimeric antigen receptor may be referred to as a CAR T cell. "Extracellular domain" (or "ECD") refers to a portion of a polypeptide that, when the polypeptide is present in a cell membrane, is understood to reside outside of the cell membrane, in the extracellular space.

The term "neutralizing" refers to an antigen binding molecule, scFv, antibody, or a fragment thereof that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

"Transformation" refers to any process by which exogenous DNA is introduced into a host cell. Transformation may occur under natural or artificial conditions using various methods. Transformation may be achieved using any known method for the insertion of foreign nucleic acid sequences into a prokaryotic or eukaryotic host cell. In some embodiments, some transformation methodology is selected based on the host cell being transformed and/or the nucleic acid to be inserted. Methods of transformation may comprise, yet are not limited to, viral infection, electroporation, and lipofection. In some embodiments, a "transformed" cell is stably transformed in that the inserted DNA is capable of replication either as an autonomously replicating plasmid or as part of the host chromosome. In some embodiments, a transformed cell may express introduced nucleic acid.

Term "vector" refers to a recipient nucleic acid molecule modified to comprise or incorporate a provided nucleic acid sequence. One type of vector is a "plasmid," which refers to a circular double stranded DNA molecule into which additional DNA may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) may be integrated into the genome of a host cell upon introduction into the host cell, and thereby are replicated along with the host genome. Moreover, certain vectors comprise sequences that direct expression of inserted genes to which they are operatively linked. Such vectors may be referred to herein as "expression vectors." Standard techniques may be used for engineering of vectors, e.g., as found in Sambrook et al., Molecular Cloning: A Laboratory Manual (2d ed., Cold Spring Harbor Laboratory Press, Cold Spring Harbor, N.Y. (1989)), which is incorporated herein by reference for any purpose.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising at least one costimulatory domain and at least one activating domain. The co-stimulatory domain can be derived from a naturally-occurring co-stimulatory domain, or a variant thereof, e.g., a variant having a truncated hinge domain ("THD"), and the activating domain can be derived from, e.g., CD3-zeta. In certain embodiments, the CAR is designed to have two, three, four, or more costimulatory domains. The CAR scFv can be designed to target, for example, CD19, which is a transmembrane protein expressed by cells in the B cell lineage, including all normal B cells and B cell malignances, including but not limited to NHL, CLL, and non-T cell ALL. In some embodiments, the CAR is engineered such that the costimulatory domain is expressed as a separate polypeptide chain. Example CAR T cell therapies and constructs are described in U.S. Patent Publication Nos. 2013/0287748, 2014/0227237, 2014/0099309, and 2014/0050708, and these references are incorporated by reference in their entirety. "Adoptive cell therapy" or "ACT" involves transfer of immune cells with anti-tumor activity into a subject, e.g., a cancer patient. In some embodiments, ACT is a treatment approach that involves the use of lymphocytes (e.g., engineered lymphocytes) with anti-tumor activity.

"Antigen presenting cell" or "APC" refers to cells that process and present antigens to T-cells. Exemplary APCs comprise dendritic cells, macrophages, B cells, certain activated epithelial cells, and other cell types capable of TCR stimulation and appropriate T cell costimulation.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

Term "identity" refers to the overall relatedness between polymeric molecules, e.g., between nucleic acid molecules (e.g., DNA molecules and/or RNA molecules) and/or between polypeptide molecules. Methods for the calculation of a percent identity as between two provided polypeptide sequences are known. Calculation of the percent identity of two nucleic acid or polypeptide sequences, for example, may be performed by aligning the two sequences for optimal comparison purposes (e.g., gaps may be introduced in one or both of a first and a second sequences for optimal alignment and non-identical sequences may be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. Comparison or alignment of sequences and determination of percent identity between two sequences may be accomplished using a mathematical algorithm, such as BLAST (basic local alignment search tool). In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical (e.g., 85-90%, 85-95%, 85-100%, 90-95%, 90-100%, or 95-100%).

To calculate percent identity, the sequences being compared are typically aligned in a way that gives the largest match between the sequences. One example of a computer program that can be used to determine percent identity is the GCG program package, which includes GAP (Devereux et al., 1984, *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, *Proc. Natl. Acad. Sci. U.S.A.* 89:10915-10919 for the BLOSUM 62 comparison matrix) is also used by the algorithm. Other algorithms are also available for comparison of amino acid or nucleic acid sequences, comprising those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., Methods in Enzymology; Altschul, et al., "Gapped BLAST and PSI-BLAST: a new generation of protein database search programs," *Nucleic Acids Res.* 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying similar sequences, the programs mentioned above generally provide an indication of the degree of similarity. In some embodiments, two sequences are considered to be substantially similar if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are similar and/or identical over a relevant stretch of residues (e.g., 85-90%, 85-95%, 85-100%, 90-95%, 90-100%, or 95-100%). In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues. Sequences with substantial sequence similarity may be homologs of one another.

"Combination therapy" refers to those situations in which a subject is simultaneously exposed to two or more therapeutic regimens (e.g., two or more therapeutic moieties). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

The term "dosage form" may be used to refer to a physically discrete unit of an active agent (e.g., an antigen binding system or antibody) for administration to a subject. Generally, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population. The total amount of a therapeutic composition or agent administered to a subject is determined by one or more medical practitioners and may involve administration of more than one dosage forms.

The term "dosing regimen" may be used to refer to a set of one or more unit doses that are administered individually to a subject. In some embodiments, a given therapeutic agent has a recommended dosing regimen, which may involve one or more doses. In some embodiments, a dosing regimen comprises a plurality of doses each of which is separated in time from other doses. In some embodiments, a dosing regimen comprises a plurality of doses and consecutive doses are separated from one another by time periods of equal length; in some embodiments, a dosing regimen comprises a plurality of doses and consecutive doses are separated from one another by time periods of at least two different lengths. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen is periodically adjusted to achieve a desired or beneficial outcome.

"Effector function" refers to a biological result of interaction of an antibody Fc region with an Fc receptor or ligand. Effector functions comprise, without limitation, antibody-dependent cell-mediated cytotoxicity (ADCC), antibody-dependent cell-mediated phagocytosis (ADCP), and complement-mediated cytotoxicity (CMC). An effector function may be antigen binding dependent, antigen binding independent, or both. ADCC refers to lysis of antibody-bound target cells by immune effector cells. Without wishing to be bound by any theory, ADCC is generally understood to involve Fc receptor (FcR)-bearing effector cells recognizing and subsequently killing antibody-coated target cells (e.g., cells that express on their surface antigens to which an antibody is bound). Effector cells that mediate ADCC may comprise immune cells, comprising yet not limited to, one or more of natural killer (NK) cells, macrophages, neutrophils, eosinophils.

"Effector cell" refers to a cell of the immune system that expresses one or more Fc receptors and mediates one or more effector functions. In some embodiments, effector cells may comprise, without limitation, one or more of monocytes, macrophages, neutrophils, dendritic cells, eosinophils, mast cells, platelets, large granular lymphocytes, Langerhans' cells, natural killer (NK) cells, T-lymphocytes, and B-lymphocytes. Effector cells may be of any organism comprising, without limitation, humans, mice, rats, rabbits, and monkeys.

The term "excipient" refers to an agent that may be comprised in a composition, for example to provide or contribute to a desired consistency or stabilizing effect. In some embodiments, a suitable excipient may comprise, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

A "fragment" or "portion" of a material or entity as described herein has a structure that comprises a discrete portion of the whole, e.g., of a physical entity or abstract entity. In some embodiments, a fragment lacks one or more moieties found in the whole. In some embodiments, a fragment consists of or comprises a characteristic structural element, domain or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer (e.g., 85-90%, 85-95%, 85-100%, 90-95%, 90-100%, or 95-100%). The whole material or entity may in some embodiments be referred to as the "parent" of the fragment.

The term "fusion polypeptide" or "fusion protein" generally refers to a polypeptide comprising at least two segments. Generally, a polypeptide containing at least two such segments is considered to be a fusion polypeptide if the two segments are moieties that (1) are not comprised in nature in the same peptide, and/or (2) have not previously been linked or connected to one another in a single polypeptide, and/or (3) have been linked or connected to one another through action of the hand of man.

The term "isolated" refers to a substance that (1) has been separated from at least some components with which it was associated at an earlier time or with which the substance would otherwise be associated, and/or (2) is present in a composition that comprises a limited or defined amount or concentration of one or more known or unknown contaminants. An isolated substance, in some embodiments, may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% (e.g., 85-90%, 85-95%, 85-100%, 90-95%, 90-100%, or 95-100%) of other non-substance components with which the substance was associated at an earlier time, e.g., other components or contaminants with which the substance was previously or otherwise would be associated. In certain instances, a substance is isolated if it is present in a composition that comprises a limited or reduced amount or concentration of molecules of a same or similar type. For instance, in certain instances, a nucleic acid, DNA, or RNA substance is isolated if it is present in a composition that comprises a limited or reduced amount or concentration of non-substance nucleic acid, DNA, or RNA molecules. For instance, in certain instances, a polypeptide substance is isolated if it is present in a composition that comprises a limited or reduced amount or concentration of non-substance polypeptide molecules. In certain embodiments, an amount may be, e.g., an amount measured relative to the amount of a desired substance present in a composition. In certain embodiments, a limited amount may be an amount that is no more than 100% of the amount of substance in a composition, e.g., no more than 1%, 5%, 10%, 20%, 30%, 40%, 50%, 60%, 70%, 80%, 90%, or 95% of the amount of substance in a composition (e.g., 85-90%, 85-95%, 85-100%, 90-95%, 90-100%, or 95-100%). In certain instances, a composition is pure or substantially pure with respect to a selected substance. In some embodiments, an isolated substance is about 80%, about 85%, about 90%, about 91%, about 92%, about 93%, about 94%, about 95%, about 96%, about 97%, about 98%, about 99%, or more than about 99% pure (e.g., 85-90%, 85-95%, 85-100%, 90-95%, 90-100%, or 95-100%). A substance is "pure" if it is substantially free of other components or of contaminants. In some embodiments, a substance may still be considered "isolated" or even "pure," after having been combined with certain other components such as, for example, one or more carriers or excipients (e.g., buffer, solvent, water, etc.); in such embodiments, percent isolation or purity of the substance is calculated without comprising such carriers or excipients.

"Nucleic acid" refers to any polymeric chain of nucleotides. A nucleic acid may be DNA, RNA, or a combination thereof. In some embodiments, a nucleic acid comprises one or more natural nucleic acid residues. In some embodiments, a nucleic acid comprises of one or more nucleic acid analogs. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long (e.g., 20 to 100, 20 to 500, 20 to 1000, 20 to 2000, or 20 to 5000 or more residues). In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide.

"Operably linked" refers to a juxtaposition where the components described are in a relationship permitting them to function in their intended manner. For example, a control element "operably linked" to a functional element is associated in such a way that expression and/or activity of the functional element is achieved under conditions compatible with the control element.

The term "pharmaceutically acceptable" refers to a molecule or composition that, when administered to a recipient, is not deleterious to the recipient thereof, or that any deleterious effect is outweighed by a benefit to the recipient thereof. With respect to a carrier, diluent, or excipient used to formulate a composition as disclosed herein, a pharmaceutically acceptable carrier, diluent, or excipient must be compatible with the other ingredients of the composition and not deleterious to the recipient thereof, or any deleterious effect must be outweighed by a benefit to the recipient. The term "pharmaceutically acceptable carrier" means a pharmaceutically-acceptable material, composition or vehicle, such as a liquid or solid filler, diluent, excipient, or solvent encapsulating material, involved in carrying or transporting an agent from one portion of the body to another (e.g., from one organ to another). Each carrier present in a pharmaceutical composition must be "acceptable" in the sense of being compatible with the other ingredients of the formulation and not deleterious to the patient, or any deleterious effect must be outweighed by a benefit to the recipient. Some examples of materials which may serve as pharmaceutically acceptable carriers comprise: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "pharmaceutical composition" refers to a composition in which an active agent is formulated together with one or more pharmaceutically acceptable carriers. In some embodiments, the active agent is present in a unit dose amount appropriate for administration in a therapeutic regimen that shows a statistically significant probability of achieving a predetermined therapeutic effect when administered to a relevant subject or population. In some embodiments, a pharmaceutical composition may be formulated for administration in solid or liquid form, comprising, without limitation, a form adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

The term "reference" describes a standard or control relative to which a comparison is performed. For example, in some embodiments, an agent, animal, individual, population, sample, sequence, or value of interest is compared with a reference or control that is an agent, animal, individual, population, sample, sequence, or value. In some embodiments, a reference or control is tested, measured, and/or determined substantially simultaneously with the testing, measuring, or determination of interest. In some embodiments, a reference or control is a historical reference or control, optionally embodied in a tangible medium. Generally, a reference or control is determined or characterized under comparable conditions or circumstances to those under assessment. When sufficient similarities are present to justify reliance on and/or comparison to a selected reference or control.

The disclosure may employ, unless indicated specifically to the contrary, methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); Transcription and Translation (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as Advances in Immunology.

The present disclosure describes engineered constructs of dominant negative TGF-β Receptors designed to inhibit the immunosuppressive effects of TGF-β in the TME. These constructs may also stimulate cytokine signaling to enhance T cell function in the TME. The constructs described herein may be used alone or in combination with each other, and/or in combination with other immunotherapies, in order to inhibit TGF-β induced immunosuppression. The engineered dominant negative TGF-β Receptors disclosed herein may comprise, consist essentially of, or consist of the sequences provided herein.

Wild-type TGF-β Receptor Type I (TGF-βRI) is the portion of the TGF-β receptor complex that transmits the intracellular, suppressive pSMAD signaling scheme. The full length wild-type nucleic acid sequence for TGF-βRI is 1509 nucleotides in length as shown in SEQ ID NO: 1.

```
                                              (SEQ ID NO: 1)
ATGGAGGCGGCGGTCGCTGCTCCGCGTCCCCGGCTGCTCCTCCTCGTGCT

GGCGGCGGCGGCGGCGGCGGCGGCGGCGCTGCTCCCGGGGGCGACGGCGT

TACAGTGTTTCTGCCACCTCTGTACAAAAGACAATTTTACTTGTGTGACA

GATGGGCTCTGCTTTGTCTCTGTCACAGAGACCACAGACAAAGTTATACA

CAACAGCATGTGTATAGCTGAAATTGACTTAATTCCTCGAGATAGGCCGT

TTGTATGTGCACCCTCTTCAAAAACTGGGTCTGTGACTACAACATATTGC

TGCAATCAGGACCATTGCAATAAAATAGAACTTCCAACTACTGTAAAGTC

ATCACCTGGCCTTGGTCCTGTGGAACTGGCAGCTGTCATTGCTGGACCAG

TGTGCTTCGTCTGCATCTCACTCATGTTGATGGTCTATATCTGCCACAAC

CGCACTGTCATTCACCATCGAGTGCCAAATGAAGAGGACCCTTCATTAGA

TCGCCCTTTTATTTCAGAGGGTACTACGTTGAAAGACTTAATTTATGATA

TGACAACGTCAGGTTCTGGCTCAGGTTTACCATTGCTTGTTCAGAGAACA

ATTGCGAGAACTATTGTGTTACAAGAAAGCATTGGCAAAGGTCGATTTGG

AGAAGTTTGGAGAGGAAAGTGGCGGGGAGAAGAAGTTGCTGTTAAGATAT

TCTCCTCTAGAGAAGAACGTTCGTGGTTCCGTGAGGCAGAGATTTATCAA
```

```
-continued
ACTGTAATGTTACGTCATGAAAACATCCTGGGATTTATAGCAGCAGACAA

TAAAGACAATGGTACTTGGACTCAGCTCTGGTTGGTGTCAGATTATCATG

AGCATGGATCCCTTTTTGATTACTTAAACAGATACACAGTTACTGTGGAA

GGAATGATAAAACTTGCTCTGTCCACGGCGAGCGGTCTTGCCCATCTTCA

CATGGAGATTGTTGGTACCCAAGGAAAGCCAGCCATTGCTCATAGAGATT

TGAAATCAAAGAATATCTTGGTAAAGAAGAATGGAACTTGCTGTATTGCA

GACTTAGGACTGGCAGTAAGACATGATTCAGCCACAGATACCATTGATAT

TGCTCCAAACCACAGAGTGGGAACAAAAAGGTACATGGCCCCTGAAGTTC

TCGATGATTCCATAAATATGAAACATTTTGAATCCTTCAAACGTGCTGAC

ATCTATGCAATGGGCTTAGTATTCTGGGAAATTGCTCGACGATGTTCCAT

TGGTGGAATTCATGAAGATTACCAACTGCCTTATTATGATCTTGTACCTT

CTGACCCATCAGTTGAAGAAATGAGAAAAGTTGTTTGTGAACAGAAGTTA

AGGCCAAATATCCCAAACAGATGGCAGAGCTGTGAAGCCTTGAGAGTAAT

GGCTAAAATTATGAGAGAATGTTGGTATGCCAATGGAGCAGCTAGGCTTA

CAGCATTGCGGATTAAGAAAACATTATCGCAACTCAGTCAACAGGAAGGC

ATCAAAATG.
```

The full length wild-type amino acid (aa) sequence for TGF-βRI is 503 amino acids as shown in SEQ ID NO: 2. The full length TGF-βRI polypeptide of SEQ ID NO: 2 includes a signal peptide (at approximately amino acids 1-33), an extracellular domain (at approximately amino acids 34-126), a transmembrane domain (at approximately amino acids 127-147) and an intracellular domain (at approximately amino acids 148-503). The intracellular domain includes four, key threonine sites located between amino acids 185-204 of the intracellular domain of TGF-βRI and initiates pSMAD signaling.

```
                                         (SEQ ID NO: 2)
MEAAVAAPRPRLLLLVLAAAAAAAAALLPGATALQCFCHLCTKDNFTCVT

DGLCFVSVTETTDKVIHNSMCIAEIDLIPRDRPFVCAPSSKTGSVTTTYC

CNQDHCNKIELPTTVKSSPGLGPVELAAVIAGPVCFVCISLMLMVYICHN

RTVIHHRVPNEEDPSLDRPFISEGTTLKDLIYDMTTSGSGSGLPLLVQRT

IARTIVLQESIGKGRFGEVWRGKWRGEEVAVKIFSSREERSWFREAEIYQ

TVMLRHENILGFIAADNKDNGTWTQLWLVSDYHEHGSLFDYLNRYTVTVE

GMIKLALSTASGLAHLHMEIVGTQGKPAIAHRDLKSKNILVKKNGTCCIA

DLGLAVRHDSATDTIDIAPNHRVGTKRYMAPEVLDDSINMKHFESFKRAD

IYAMGLVFWEIARRCSIGGIHEDYQLPYYDLVPSDPSVEEMRKVVCEQKL

RPNIPNRWQSCEALRVMAKIMRECWYANGAARLTALRIKKTLSQLSQQEG

IKM.
```

Because of its role in initiating the intracellular signaling cascade, a modified TGF-βR1 construct may be a potential therapeutic target. Without being bound by any theory, it is hypothesized that a dominant-negative TGF-βRI construct could be designed to inhibit the phosphorylation cascade and thus limit the immunosuppressive effects of TGF-β on T cell function. Any truncation or modification that results in suppressing or reducing phosphorylation such that it results in a non-functional signaling pathway is contemplated by the disclosure. In one embodiment the DN TGF-βRI may be truncated after the transmembrane domain or modified, such that the polypeptide lacks one or more amino acid residues responsible for signaling and phosphorylation and results in a non-functional signaling pathway as compared to the wild-type receptor. In some embodiments, the DN TGF-βRI may be truncated before the threonine at amino acid 185 of the intracellular domain of SEQ ID NO: 2. In some embodiments, the DN TGF-βRI may be truncated such that it has no intracellular domain. In other embodiments, the DN TGF-βRI may be modified to replace the intracellular domain with another natural or non-naturally occurring sequence that does not include amino acid residues involved in phosphorylation signaling. In another embodiment, the polypeptide is truncated or modified in such a way so as to reduce phosphorylation activity. In another embodiment, the polypeptide is truncated or modified in such a way so as to inhibit phosphorylation signaling molecules from interacting with pSMAD molecules. The present disclosure describes truncated, dominant-negative TGF-βRI constructs (DN TGF-β RI) that have been engineered to remove the amino acids involved in phosphorylation signaling of the intracellular domain of the wild-type TGF-βRI.

In some embodiments described herein, the DN TGF-βRI comprises an extracellular ligand binding domain for binding TGF-β having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 3.

```
                                         (SEQ ID NO: 3)
LQCFCHLCTKDNFTCVTDGLCFVSVTETTDKVIHNSMCIAEIDLIPRDRP

FVCAPSSKTGSVTTTYCCNQDHCNKIELPTTVKSSPGLGPVEL.
```

In some embodiments, the DN TGF-βRI extracellular ligand binding domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 3 may be fused to one or more heterologous polypeptide sequences. The extracellular domain of the DN TGF-βRI may be engineered to recognize and bind to the target TGF-β molecule in order to initiate oligomerization of the complex of TGF-βRII with the DN TGF-βRI. Furthermore, the present disclosure contemplates the binding of DN TGF-βRI to all TGF-β isoforms, including transforming growth factor β Type I (TGF-β1), transforming growth factor β Type II (TGF-β2), transforming growth factor β Type III (TGF-β3) and transforming growth factor β Type IV (TGF-β4). In some embodiments, the DN TGF-βRI may be engineered to bind TGF-β1, TGF-β2, TGF-β3 and/or TGF-β4. In one embodiment, the DN TGF-βRI binds TGF-β1.

In another embodiment described herein, the DN TGF-βRI comprises an extracellular binding domain fused to a transmembrane domain. The DN TGF-βRI may comprise a transmembrane domain that comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type TGF-βRI transmembrane domain or a portion thereof. By way of non-limiting example, the transmembrane domain may comprise an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 4, the wild-type TGF-βRI transmembrane domain. AAVIAGPVCFV-CISLMLMVYI (SEQ ID NO: 4). In other embodiments, the transmembrane domain is a heterologous transmembrane domain, including any of the various transmembrane domains described herein. The transmembrane domain of the DN TGF-βRI generally comprises a hydrophobic alpha helix that spans at least a portion of the membrane and assists in anchoring the DN TGF-βRI to the cell membrane and facilitates dimerization of the DN TGF-βRI construct. The transmembrane domain of the DN TGF-βRI may be designed such that after TGF-β binding, no intracellular signal is transmitted in the cell via the DN TGF-βRI. By way of a non-limiting example, the transmembrane domain of the DN TGF-βRI may be derived from any another polypeptide expressed in an immune cell or precursor cell thereof, having a transmembrane domain, including other transmembrane domains disclosed herein. In another embodiment, the transmembrane domain may be derived from a polypeptide that is either naturally or not naturally expressed in a T cell. It is understood that the portion of the polypeptide that comprises the transmembrane domain of a polypeptide may include additional sequences from the polypeptide, for example, additional sequences adjacent on the N-terminal or C-terminal end of the transmembrane domain, or other regions of the polypeptide, as desired. In one embodiment, the DN TGF-βRI may have a transmembrane domain derived from, by way of non-limiting example, TGF-βRI, PDGFR, CD4, CD8, CD28, CD127, CD132, CD3ζ, 4-1BB, OX40, ICOS, CTLA-4, PD-1, LAG-3, 2B4, IL-5, IL-7, IL-7Rα, BTLA or mutants thereof. In one embodiment described herein, the DN TGF-PRI comprises an extracellular ligand binding domain and a transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 5.

(SEQ ID NO: 5)
LQCFCHLCTKDNFTCVTDGLCFVSVTETTDKVIHNSMCIAEIDLIPRDRP

FVCAPSSKTGSVTTTYCCNQDHCNKIELPTTVKSSPGLGPVELAAVIAGP

VCFVCISLMLMVYI.

The DN TGF-βRI constructs described herein may be used with any suitable intracellular domain or portion thereof or without an intracellular domain. In another embodiment described herein, the DN TGF-βRI comprises an extracellular domain fused to a transmembrane domain further fused to an intracellular domain. The intracellular domain of wild-type TGF-βRI is where phosphorylation signaling occurs that inhibits T cell function through pSMAD2/3 activation. Thus, in one embodiment, the DN TGF-βRI described herein comprises an intracellular domain that is truncated after amino acid 147 of SEQ ID NO: 2 such that intracellular signaling of the cell is reduced or inhibited.

Such a truncation reduces the length of the receptor protein and results in a dominant-negative effect that inhibits the phosphorylation cascade that would have resulted in T cell suppression. As a result, the DN TGF-βRI intracellular domain may be derived from any polypeptide that is either naturally or not naturally expressed in the T cell, so long as the receptor is able to anchor in the membrane and prevent any intracellular signaling from occurring. By way of non-limiting example, the intracellular domain may be derived from TGF-βRI, TGF-PDGFR, CD4, CD8, CD28, CD127, CD132, CD3ζ, 4-1BB, OX40, ICOS, CTLA-4, PD-1, LAG-3, 2B4, IL-5, IL-7, IL-7Rα, BTLA or mutants thereof.

In one embodiment described herein, the DN TGF-βRI may include the intracellular domain of SEQ ID NO: 6. RVNRQ (SEQ ID NO: 6). In some embodiments, the DN TGF-βRI comprises an extracellular ligand binding domain of TGF-βRI, a transmembrane domain of TGF-βRI and an intracellular binding domain of SEQ ID NO: 6, having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 7.

(SEQ ID NO: 7)
LQCFCHLCTKDNFTCVTDGLCFVSVTETTDKVIHNSMCIAEIDLIPRDRP

FVCAPSSKTGSVTTTYCCNQDHCNKIELPTTVKSSPGLGPVELAAVIAGP

VCFVCISLMLMVYIRVNRQ.

The engineered DN TGF-βRI described herein may also comprise an N-terminal signal peptide at the N-terminus of the extracellular ligand binding domain of DN TGF-βRI. In one embodiment, a heterologous signal peptide may be used. The extracellular domain of a DN TGF-βRI may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as a DN TGF-βRI is generally expressed at the cell surface as a mature protein lacking the signal peptide, whereas the precursor form of the polypeptide includes the signal peptide. Any suitable signal sequence may be used. In one embodiment described herein, the DN TGF-βRI comprises the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 8 or a portion thereof.

(SEQ ID NO: 8)
MEAAVAAPRPRLLLLVLAAAAAAAAALLPGATA.

A signal peptide or leader may facilitate the glycosylation of DN TGF-βRI. The signal sequence or leader is a peptide sequence generally present at either the N-terminus or C-terminus of newly synthesized proteins that directs their entry into the secretory pathway. In the present disclosure, the signal peptide is joined to the N-terminus of the extracellular antigen-binding domain of the DN TGF-βRI as a fusion protein. In one embodiment, the DN TGF-βRI comprises an extracellular ligand binding domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type TGF-βRI and a signal peptide at the N-terminus of the extracellular domain TGF-βRI, having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 9.

(SEQ ID NO: 9)
MEAAVAAPRPRLLLLVLAAAAAAAAALLPGATALQCFCHLCTKDNFTCVT

DGLCFVSVTETTDKVIHNSMCIAEIDLIPRDRPFVCAPSSKTGSVTTTYC

CNQDHCNKIELPTTVKSSPGLGPVEL.

It is understood that use of this signal peptide is exemplary. Any suitable signal peptide, as are well known in the art, may be applied to the DN TGF-βRI to provide cell surface expression in an immune cell. Useful signal peptides may be derived from cell surface proteins naturally expressed in the T cell or precursor cell thereof, including any of the signal peptides of the polypeptides disclosed herein. Thus, any suitable signal peptide may be utilized to direct the DN TGF-βRI to be expressed at the cell surface of a T cell.

Thus one embodiment described herein is an engineered DN TGF-βRI comprising a signal peptide having at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type TGF-βRI, an extracellular domain of having at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type TGF-βRI, a transmembrane domain of TGF-βRI, and an intracellular domain of SEQ ID NO: 6 having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 10.

(SEQ ID NO: 10)
MEAAVAAPRPRLLLLVLAAAAAAAAALLPGATALQCFCHLCTKDNFTCVT

DGLCFVSVTETTDKVIHNSMCIAEIDLIPRDRPFVCAPSSKTGSVTTTYC

CNQDHCNKIELPTTVKSSPGLGPVELAAVIAGPVCFVCISLMLMVYIRVN

RQ.

In addition to TGF-βRI, TGF-βRII is the second member of the TGF-receptor complex. Unlike wild-type TGF-βRI, wild-type TGF-β Receptor Type II (TGF-β RII) is constitutively active. Upon binding of the TGF-β ligand and formation of the TGF-βRI dimer-/TGF-βRII dimer-complex, the cytoplasmic domain of TGF-βRII phosphorylates TGF-βRI. Thus, TGF-βRII is responsible for activating TGF-βRI and initiating the subsequent intracellular signal transduction cascade that results in pSMAD signaling. The full length wild-type nucleic acid sequence for TGF-βRII is 1701 nucleotides in length as shown in SEQ ID NO: 12.

(SEQ ID NO: 12)
ATGGGCAGGGGCCTGCTGAGGGGCCTGTGGCCCCTGCACATCGTGCTGTG

GACCAGGATCGCCAGCACCATCCCCCCCCACGTGCAGAAGAGCGTGAACA

ACGACATGATCGTGACCGACAACAACGGCGCCGTGAAGTTCCCCCAGCTG

TGCAAGTTCTGCGACGTGAGGTTCAGCACCTGCGACAACCAGAAGAGCTG

CATGAGCAACTGCAGCATCACCAGCATCTGCGAGAAGCCCCAGGAGGTGT

GCGTGGCCGTGTGGAGGAAGAACGACGAGAACATCACCCTGGAGACCGTG

TGCCACGACCCCAAGCTGCCCTACCACGACTTCATCCTGGAGGACGCCGC

CAGCCCCAAGTGCATCATGAAGGAGAAGAAGAAGCCCGGCGAGACCTTCT

TCATGTGCAGCTGCAGCAGCGACGAGTGCAACGACAACATCATCTTCAGC

GAGGAGTACAACACCAGCAACCCCGACCTGCTGCTGGTGATCTTCCAGGT

GACCGGCATCAGCCTGCTGCCCCCCCTGGGCGTGGCCATCAGCGTGATCA

TCATCTTCTACTGCTACAGGGTGAACAGGCAGCAGAAGCTGAGCAGCACC

TGGGAGACCGGCAAGACCAGGAAGCTGATGGAGTTCAGCGAGCACTGCGC

CATCATCCTGGAGGACGACAGGAGCGACATCAGCAGCACCTGCGCCAACA

ACATCAACCACAACACCGAGCTGCTGCCCATCGAGCTGGACACCCTGGTG

GGCAAGGGCAGGTTCGCCGAGGTGTACAAGGCCAAGCTGAAGCAGAACAC

CAGCGAGCAGTTCGAGACCGTGGCCGTGAAGATCTTCCCCTACGAGGAGT

ACGCCAGCTGGAAGACCGAGAAGGACATCTTCAGCGACATCAACCTGAAG

CACGAGAACATCCTGCAGTTCCTGACCGCCGAGGAGAGGAAGACCGAGCT

GGGCAAGCAGTACTGGCTGATCACCGCCTTCCACGCCAAGGGCAACCTGC

AGGAGTACCTGACCAGGCACGTGATCAGCTGGGAGGACCTGAGGAAGCTG

GGCAGCAGCCTGGCCAGGGGCATCGCCCACCTGCACAGCGACCACACCCC

CTGCGCAGGCCCAAGATGCCCATCGTGCACAGGGACCTGAAGAGCAGCA

ACATCCTGGTGAAGAACGACCTGACCTGCTGCCTGTGCGACTTCGGCCTG

AGCCTGAGGCTGGACCCCACCCTGAGCGTGGACGACCTGGCCAACAGCGG

CCAGGTGGGCACCGCCAGGTACATGGCCCCCGAGGTGCTGGAGAGCAGGA

TGAACCTGGAGAACGTGGAGAGCTTCAAGCAGACCGACGTGTACAGCATG

GCCCTGGTGCTGTGGGAGATGACCAGCAGGTGCAACGCCGTGGGCGAGGT

GAAGGACTACGAGCCCCCCTTCGGCAGCAAGGTGAGGGAGCACCCCTGCG

TGGAGAGCATGAAGGACAACGTGCTGAGGGACAGGGGCAGGCCCGAGATC

CCCAGCTTCTGGCTGAACCACCAGGGCATCCAGATGGTGTGCGAGACCCT

GACCGAGTGCTGGGACCACGACCCCGAGGCCAGGCTGACCGCCCAGTGCG

TGGCCGAGAGGTTCAGCGAGCTGGAGCACCTGGACAGGCTGAGCGGCAGG

AGCTGCAGCGAGGAGAAGATCCCCGAGGACGGCAGCCTGAACACCACCAA

G.

The full length wild-type amino acid sequence for TGF-βRII is 567 amino acids as shown in SEQ ID NO: 13. The full length TGF-βRII polypeptide of SEQ ID NO: 13 includes a signal peptide (at approximately amino acids 1-22), an extracellular domain (at approximately amino acids 33-170), a transmembrane domain (at approximately amino acids 171-201) and an intracellular domain (at approximately amino acids 202-567).

(SEQ ID NO: 13)
MGRGLLRGLWPLHIVLWTRIASTIPPHVQKSVNNDMIVTDNNGAVKFPQL

CKFCDVRFSTCDNQKSCMSNCSITSICEKPQEVCVAVWRKNDENITLETV

CHDPKLPYHDFILEDAASPKCIMKEKKKPGETFFMCSCSSDECNDNIIFS

EEYNTSNPDLLLVIFQVTGISLLPPLGVAISVIIIFYCYRVNRQQKLSST

WETGKTRKLMEFSEHCAIILEDDRSDISSTCANNINHNTELLPIELDTLV

GKGRFAEVYKAKLKQNTSEQFETVAVKIFPYEEYASWKTEKDIFSDINLK

-continued

HENILQFLTAEERKTELGKQYWLITAFHAKGNLQEYLTRHVISWEDLRKL

GSSLARGIAHLHSDHTPCGRPKMPIVHRDLKSSNILVKNDLTCCLCDFGL

SLRLDPTLSVDDLANSGQVGTARYMAPEVLESRMNLENVESFKQTDVYSM

ALVLWEMTSRCNAVGEVKDYEPPFGSKVREHPCVESMKDNVLRDRGRPEI

PSFWLNHQGIQMVCETLTECWDHDPEARLTAQCVAERFSELEHLDRLSGR

SCSEEKIPEDGSLNTTK.

Upon ligand binding, the intracellular domain of wild-type TGF-βRII is responsible for interaction with the intracellular domain of wild-type TGF-βRI, and phosphorylation of the four, key threonine sites located between amino acids 185-204 of the intracellular domain of wild-type TGF-βRI and initiating pSMAD signaling. Thus, without being bound by any theory and as described herein, it is believed that a truncated DN TGF-βRI would be unable to interact with TGF-βRII, and thus suppress pSMAD signal transduction.

Similarly, because of its role in initiating the phosphorylation cascade of DN TGF-βRI, it is hypothesized that an engineered dominant-negative TGF-βRII (DN TGF-βRII) may also be unable to initiate phosphorylation of DN TGF-βRI by omitting the amino acid sequences responsible for signal initiation of phosphorylation, and thus also suppress pSMAD signal transduction. Any truncation or modification that results in suppressing or reducing phosphorylation such that it results in a non-functional signaling pathway is contemplated by the disclosure. In one embodiment the DN TGF-βRII may be truncated after the transmembrane domain or modified, such that the polypeptide lacks one or more amino acid residues responsible for signaling and phosphorylation and results in a non-functional signaling pathway as compared to the wild-type receptor. In some embodiments, the DN TGF-βRII may be truncated such that it has no intracellular domain. In other embodiments, the DN TGF-βRII may be modified to replace the intracellular domain with another natural or non-naturally occurring sequence that does not include amino acid residues involved in phosphorylation signaling. In another embodiment, the polypeptide is truncated or modified in such a way so as to reduce phosphorylation activity. In another embodiment, the polypeptide is truncated or modified in such a way so as to inhibit phosphorylation signaling molecules from interacting with pSMAD molecules. Thus, in one embodiment described herein is a truncated DN TGF-βRII, where the polypeptide is truncated after the transmembrane domain and has at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 14:

(SEQ ID NO: 14)
MGRGLLRGLWPLHIVLWTRIASTIPPHVQKSVNNDMIVTDNNGAVKFPQL

CKFCDVRFSTCDNQKSCMSNCSITSICEKPQEVCVAVWRKNDENITLETV

CHDPKLPYHDFILEDAASPKCIMKEKKKPGETFFMCSCSSDECNDNIIFS

EEYNTSNPDLLLVIFQVTGISLLPPLGVAISVIIIFYCYRVNRQ.

In some embodiments described herein, the DN TGF-βRII comprises the extracellular ligand binding domain for binding of TGF-β to wild-type TGF-βRII having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 15.

(SEQ ID NO: 15)
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCScSSDECNDNIIFSEEYNTSNPD

In some embodiments, the DN TGF-βRII extracellular ligand binding domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 15 may be fused to one or more heterologous polypeptide sequences. The extracellular domain of the DN TGF-βRII may be engineered to recognize and bind to the target TGF-β molecule in order to initiate oligomerization of the complex of DN TGF-βRII with wild-type TGF-βRI or with a DN TGF-βRI as described herein. Furthermore, the present disclosure contemplates the binding of DN TGF-βRII to all TGF-β isoforms, including transforming growth factor β Type I (TGF-β1), transforming growth factor β Type II (TGF-β2), transforming growth factor β Type III (TGF-β3) and transforming growth factor β Type IV (TGF-β4). In some embodiments, the DN TGF-βRII may be engineered to bind TGF-β1, TGF-β2, TGF-β3 and/or TGF-β4. In another embodiment, the DN TGF-βRII binds TGF-β1.

In another embodiment described herein, the DN TGF-βRII comprises an extracellular binding domain fused to a transmembrane domain. The DN TGF-βRII may comprise a transmembrane domain that comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type TGF-βRII transmembrane domain or a portion thereof. By way of non-limiting example, the transmembrane domain may comprise an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 16 that includes the wild-type TGF-βRII transmembrane domain. LLLVIFQVTGISLLPPLGVAISVIIIFYCY (SEQ ID NO: 16). In other embodiments, the transmembrane domain is a heterologous transmembrane domain, including any of various transmembrane domains described herein. The transmembrane domain of the DN TGF-βRII generally comprises a hydrophobic alpha helix that spans at least a portion of the membrane and assists in anchoring the DN TGF-βRII to the membrane and facilitates dimerization of the DN TGF-βRII construct. The transmembrane domain of the DN TGF-βRII may be designed such that after TGF-β binding, no intracellular signal is transmitted in the cell via the DN TGF-βRII to TGF-βRI or DN TGF-βRI. In one embodiment described herein, the DN TGF-βRII comprises an extracellular ligand binding domain and a transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type TGF-βRII as shown in the amino acid sequence of SEQ ID NO: 17.

(SEQ ID NO: 17)
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCScSSDECNDNIIFSEEYNTSNPDLLLVIFQVTGISL

LPPLGVAISVIIIFYCY.

Without being bound by any theory, it is hypothesized that the transmembrane domain of DN TGF-βRII may impact the receptor's ability to interact with wild-type TGF-βRI or DN TGF-βRI and thus suppress pSMAD signal transduction. It is further hypothesized that changes in the transmembrane domain may also stimulate beneficial cytokine expression and signaling while suppressing pSMAD signal transduction. Thus, by way of non-limiting example, the transmembrane domain of the DN TGF-βRII may be derived from any another polypeptide expressed in an immune cell or precursor cell thereof, having a transmembrane domain, including other transmembrane domains disclosed herein. In another embodiment, the transmembrane domain may be derived from a polypeptide that is either naturally or not naturally expressed in a T cell. It is understood that the portion of the polypeptide that comprises the transmembrane domain of a polypeptide may include additional sequences from the polypeptide, for example, additional sequences adjacent on the N-terminal or C-terminal end of the transmembrane domain, or other regions of the polypeptide, as desired. In one embodiment, the DN TGF-βRII may have a transmembrane domain derived from, by way of non-limiting example, TGF-βRI, PDGFR, CD4, CD8, CD28, CD127, CD132, CD3ζ, 4-IBB, OX40, ICOS, CTLA-4, PD-1, LAG-3, 2B4, IL-5, IL-7, IL-7Rα, BTLA or mutants thereof.

In one embodiment described herein, the transmembrane domain may comprise an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 18 that includes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type IL-7Rα transmembrane domain. PILLTISILSFFSVALLVIL (SEQ ID NO: 18). In another embodiment described herein, the DN TGF-βRII comprises an extracellular ligand binding domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) wild-type TGF-βRII, a linker sequence, and the transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 18, and having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 19.

(SEQ ID NO: 19)
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGPILLTISILSF

FSVALLVIL.

In another embodiment described herein, the transmembrane domain may comprise an amino acid sequences having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 20, which is the wild-type IL-7Rα transmembrane domain having an amino acid insertion of "CPT". PILLTCPTISILSFFSVALLVIL (SEQ ID NO: 20). In another embodiment described herein, the DN TGF-βRII comprises an extracellular ligand binding domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) wild-type TGF-βRII, a linker sequence, and the transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 20, and having at least 75% sequence identity to (such as, at least 75%, at least 80%, at least 90%, at least 95%, or 100% identity; e.g., 85-90%, 85-95%, 85-100%, 90-95%, 90-100%, or 95-100%) as shown in the amino acid sequence of SEQ ID NO: 21.

(SEQ ID NO: 21)
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCScSSDECNDNIIFSEEYNTSNPDSGPILLTCPTISI

LSFFSVALLVIL.

The DN TGF-βRII constructs described herein may be used by themselves or with any suitable intracellular domain or portion thereof or with no intracellular domain and may be truncated. In one embodiment described herein, the DN TGF-βRII constructs described herein comprises an intracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 6. By way of non-limiting example, the extracellular domain of the DN TGF-βRII constructs described herein may be derived from TGF-βRI, PDGFR, CD4, CD8, CD28, CD127, CD132, CD3ζ, 4-IBB, OX40, ICOS, CTLA-4, PD-1, LAG-3, 2B4, IL-5, IL-7, IL-7Rα, BTLA, or mutants of any of the foregoing. In one embodiment described herein, the DN TGF-βRII comprises an extracellular domain fused to a transmembrane domain further fused to an intracellular domain. In another embodiment described herein, the DN TGF-βRII described herein comprises the intracellular domain of wild-type IL-7Rα having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 22.

(SEQ ID NO: 22)
ACVLWKKRIKPIVWPSLPDHKKTLEHLCKKPRKNLNVSFNPESFLDCQI

HRVDDIQARDEVEGFLQDTFPQQLEESEKQRLGGDVQSPNCPSEDVVIT

```
PESFGRDSSLTCLAGNVSACDAPILSSSRSLDCRESGKNGPHVYQDLLL

SLGTTNSTLPPPFSLQSGILTLNPVAQGQPILTSLGSNQEEAYVTMSSF

YQNQ.
```

In another embodiment, the DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type extracellular domain of TGF-βRII, a linker sequence, the transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 18, and the intracellular domain having at least 75% sequence identity to (such as, at least 75%, at least 80%, at least 90%, at least 95%, or 100% identity; e e.g., 85-90%, 85-95%, 85-100%, 90-95%, 90-100%, or 95-100%) SEQ ID NO: 22, and having at least 75% sequence identity to (such as, at least 75%, at least 80%, at least 90%, at least 95%, or 100% identity e.g., 85-90%, 85-95%, 85-100%, 90-95%, 90-100%, or 95-100%) the amino acid sequence of SEQ ID NO: 23.

```
                                       (SEQ ID NO: 23)
TIPPHVQKSVNNDMIVTDNNGAVKFPQLCKFCDVRFSTCDNQKSCMSNC

SITSICEKPQEVCVAVWRKNDENITLETVCHDPKLPYHDFILEDAASPK

CIMKEKKKPGETFFMCSCSSDECNDNIIFSEEYNTSNPDSGPILLTISI

LSFFSVALLVILACVLWKKRIKPIVWPSLPDHKKTLEHLCKKPRKNLNV

SFNPESFLDCQIHRVDDIQARDEVEGFLQDTFPQQLEESEKQRLGGDVQ

SPNCPSEDVVITPESFGRDSSLTCLAGNVSACDAPILSSSRSLDCRESG

KNGPHVYQDLLLSLGTTNSTLPPPFSLQSGILTLNPVAQGQPILTSLGS

NQEEAYVTMSSFYQNQ.
```

In another embodiment described herein, the DN TGF-βRII construct comprises the extracellular domain having at least 75% sequence identity to (such as, at least 75%, at least 80%, at least 90%, at least 95%, or 100% identity; e e.g., 85-90%, 85-95%, 85-100%, 90-95%, 90-100%, or 95-100%) wild-type TGF-βRII, a linker sequence, the transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 20 and the intracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 22, and having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the amino acid sequence of SEQ ID NO: 24.

```
                                       (SEQ ID NO: 24)
TIPPHVQKSVNNDMIVTDNNGAVKFPQLCKFCDVRFSTCDNQKSCMSNC

SITSICEKPQEVCVAVWRKNDENITLETVCHDPKLPYHDFILEDAASPK

CIMKEKKKPGETFFMCSCSSDECNDNIIFSEEYNTSNPDSGPILLTCPT

ISILSFFSVALLVILACVLWKKRIKPIVWPSLPDHKKTLEHLCKKPRKN

LNVSFNPESFLDCQIHRVDDIQARDEVEGFLQDTFPQQLEESEKQRLGG

DVQSPNCPSEDVVITPESFGRDSSLTCLAGNVSACDAPILSSSRSLDCR

ESGKNGPHVYQDLLLSLGTTNSTLPPPFSLQSGILTLNPVAQGQPILTS

LGSNQEEAYVTMSSFYQNQ.
```

The engineered DN TGF-βRII constructs described herein may also comprise an N-terminal signal peptide at the N-terminus of the extracellular ligand binding domain of TGF-βRII. In one embodiment, a heterologous signal peptide may be used. The extracellular domain of a DN TGF-βRII may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as a DN TGF-βRII is generally found at the cell surface as a mature protein lacking the signal peptide, whereas the precursor form of the polypeptide includes the signal peptide. Any suitable signal sequence may be used. In one embodiment described herein, the DN TGF-βRII constructs described herein comprise a signal sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 25 or a portion thereof. MGRGLLRGLWPL-HIVLWTRIAS (SEQ ID NO: 25). In another embodiment, the signal sequence is derived from Colony Stimulating Factor 2 Receptor Alpha subunit (CSF2Rα) comprising the amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 26 or a portion thereof. MLLLVTSLLLCELPHPAFLLIP (SEQ ID NO: 26). The signal sequences described herein may also be optionally used with any suitable protein tag, including but not limited to: V5-tag, myc-tag, HA-tag, Spot-tag, NE-tag. In one embodiment described herein, the signal sequence and tag comprise the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 27.

```
                                       (SEQ ID NO: 27)
MLLLVTSLLLCELPHPAFLLIPEQKLISEEDL.
```

A signal peptide or leader may facilitate the glycosylation of DN TGF-βRII. The signal sequence or leader is a peptide sequence generally present at either the N-terminus or C-terminus of newly synthesized proteins that directs their entry into the secretory pathway. In the instant disclosures, the signal peptide is joined to the N-terminus of the extracellular antigen-binding domain of the DN TGF-βRII as a fusion protein. In one embodiment, the DN TGF-βRII comprises an extracellular ligand binding domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type TGF-βRII and a signal peptide at the N-terminus of the extracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 28.

(SEQ ID NO: 28)
MLLLVTSLLLCELPHPAFLLIPTIPPHVQKSVNNDMIVTDNNGAVKFPQ

LCKFCDVRFSTCDNQKSCMSNCSITSICEKPQEVCVAVWRKNDENITLE

TVCHDPKLPYHDFILEDAASPKCIMKEKKKPGETFFMCSCSSDECNDNI

IFSEEYNTSNPD.

In one embodiment, the DN TGF-βRII comprises an extracellular ligand binding domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type TGF-βRII and a signal peptide at the N-terminus of the extracellular domain TGF-βRII and a tag sequence, and having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 29.

(SEQ ID NO: 29)
MLLLVTSLLLCELPHPAFLLIPEQKLISEEDLTIPPHVQKSVNNDMIVT

DNNGAVKFPQLCKFCDVRFSTCDNQKSCMSNCSITSICEKPQEVCVAVW

RKNDENITLETVCHDPKLPYHDFILEDAASPKCIMKEKKKPGETFFMCS

CSSDECNDNIIFSEEYNTSNPD.

It is understood that use of this signal peptide is exemplary. Any suitable signal peptide, as are well known in the art, may be applied to the DN TGF-βRII to provide cell surface expression in an immune cell. Useful signal peptides may be derived from cell surface proteins naturally expressed in the T cell or precursor cell thereof, including any of the signal peptides of the polypeptides disclosed herein. Thus, any suitable signal peptide may be utilized to direct the DN TGF-βRII to be expressed at the cell surface of a T cell.

Thus one embodiment described herein is an engineered DN TGF-βRII comprising a signal peptide, an extracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) wild-type TGF-βRII, a linker sequence, the transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 18 and the intracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 22, as shown in the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 30.

(SEQ ID NO: 30)
MLLLVTSLLLCELPHPAFLLIPTIPPHVQKSVNNDMIVTDNNGAVKFPQ

LCKFCDVRFSTCDNQKSCMSNCSITSICEKPQEVCVAVWRKNDENITLE

TVCHDPKLPYHDFILEDAASPKCIMKEKKKPGETFFMCSCSSDECNDNI

IFSEEYNTSNPDSGPILLTISILSFFSVALLVILACVLWKKRIKPIVWP

SLPDHKKTLEHLCKKPRKNLNVSFNPESFLDCQIHRVDDIQARDEVEGF

LQDTFPQQLEESEKQRLGGDVQSPNCPSEDVVITPESFGRDSSLTCLAG

NVSACDAPILSSSRSLDCRESGKNGPHVYQDLLLSLGTTNSTLPPPFSL

QSGILTLNPVAQGQPILTSLGSNQEEAYVTMSSFYQNQ.

In another embodiment described herein is an engineered DN TGF-βRII comprising a signal peptide, a tag sequence, an extracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) wild-type TGF-βRII, a linker sequence, the transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 18 and the intracellular domain of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 22, as shown by the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 31.

(SEQ ID NO: 31)
MLLLVTSLLLCELPHPAFLLIPEQKLISEEDLTIPPHVQKSVNNDMIVT

DNNGAVKFPQLCKFCDVRFSTCDNQKSCMSNCSITSICEKPQEVCVAVW

RKNDENITLETVCHDPKLPYHDFILEDAASPKCIMKEKKKPGETFFMCS

CSSDECNDNIIFSEEYNTSNPDSGPILLTISILSFFSVALLVILACVLW

KKRIKPIVWPSLPDHKKTLEHLCKKPRKNLNVSFNPESFLDCQIHRVDD

IQARDEVEGFLQDTFPQQLEESEKQRLGGDVQSPNCPSEDVVITPESFG

RDSSLTCLAGNVSACDAPILSSSRSLDCRESGKNGPHVYQDLLLSLGTT

NSTLPPPFSLQSGILTLNPVAQGQPILTSLGSNQEEAYVTMSSFYQNQ.

Another embodiment described herein is an engineered DN TGF-βRII comprising a signal peptide, an extracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) wild-type TGF-βRII, a linker sequence, the transmembrane domain of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 18 and the intracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 22, as shown by the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 32.

(SEQ ID NO: 32)
MLLLVTSLLLCELPHPAFLLIPTIPPHVQKSVNNDMIVTDNNGAVKFPQ

LCKFCDVRFSTCDNQKSCMSNCSITSICEKPQEVCVAVWRKNDENITLE

TVCHDPKLPYHDFILEDAASPKCIMKEKKKPGETFFMCSCSSDECNDNI

IFSEEYNTSNPDSGPILLTISILSFFSVALLVILACVLWKKRIKPIVWP

SLPDHKKTLEHLCKKPRKNLNVSFNPESFLDCQIHRVDDIQARDEVEGF

LQDTFPQQLEESEKQRLGGDVQSPNCPSEDVVITPESFGRDSSLTCLAG

NVSACDAPILSSSRSLDCRESGKNGPHVYQDLLLSLGTTNSTLPPPFSL

QSGILTLNPVAQGQPILTSLGSNQEEAYVTMSSFYQNQ.

Another embodiment described herein is an engineered DN TGF-βRII comprising a signal peptide, a tag sequence, an extracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) wild-type TGF-βRII, a linker sequence, the transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 20 and the intracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 22, as shown by the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 33.

(SEQ ID NO: 33)
MLLLVTSLLLCELPHPAFLLIPEQKLISEEDLTIPPHVQKSVNNDMIVT

DNNGAVKFPQLCKFCDVRFSTCDNQKSCMSNCSITSICEKPQEVCVAVW

RKNDENITLETVCHDPKLPYHDFILEDAASPKCIMKEKKKPGETFFMCS

CSSDECNDNIIFSEEYNTSNPDSGPILLTCPTISILSFFSVALLVILAC

VLWKKRIKPIVWPSLPDHKKTLEHLCKKPRKNLNVSFNPESFLDCQIHR

VDDIQARDEVEGFLQDTFPQQLEESEKQRLGGDVQSPNCPSEDVVITPE

SFGRDSSLTCLAGNVSACDAPILSSSRSLDCRESGKNGPHVYQDLLLSL

GTTNSTLPPPFSLQSGILTLNPVAQGQPILTSLGSNQEEAYVTMSSFYQ

NQ.

Another embodiment described herein is an engineered DN TGF-βRII comprising a signal peptide, an extracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) wild-type TGF-βRII, a linker sequence, the transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 20 and the intracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 22, as shown by the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 34.

(SEQ ID NO: 34)
MLLLVTSLLLCELPHPAFLLIPTIPPHVQKSVNNDMIVTDNNGAVKFPQ

LCKFCDVRFSTCDNQKSCMSNCSITSICEKPQEVCVAVWRKNDENITLE

TVCHDPKLPYHDFILEDAASPKCIMKEKKKPGETFFMCSCSSDECNDNI

IFSEEYNTSNPDSGPILLTCPTISILSFFSVALLVILACVLWKKRIKPI

VWPSLPDHKKTLEHLCKKPRKNLNVSFNPESFLDCQIHRVDDIQARDEV

EGFLQDTFPQQLEESEKQRLGGDVQSPNCPSEDVVITPESFGRDSSLTC

LAGNVSACDAPILSSSRSLDCRESGKNGPHVYQDLLLSLGTTNSTLPPP

FSLQSGILTLNPVAQGQPILTSLGSNQEEAYVTMSSFYQNQ.

Both engineered T cell receptors (TCR) and chimeric antigen receptor (CAR) therapies harness the specificity and immunotherapeutic effect of T cells for the treatment of a wide variety of malignancies. Some studies suggest that these therapies may be susceptible to the suppressive factors in the TME that result from T cell suppression by TGF-β (Bendle et al., *J Immunol*, 191:3232-3239 (2013) and Vong et al., *Blood*, 130:1791 (2017)). The present disclosure contemplates the use of the DN TGF-β Receptors described herein in combination with either TCR or CAR therapies as a way to maintain, or in some cases, restore TCR and/or CAR expansion in the presence of TGF-β suppression.

Chimeric antigen receptor (CAR) T cell therapy provides another therapeutic approach against tumor progression. Clinically, investigators have demonstrated that CAR expansion and persistence is correlated with therapeutic efficacy. Without being bound by any theory, it is believed that TGF-β repressed T cell populations found in the TME may be limiting CAR T cell expansion and persistence in patients who do not respond to CAR therapy. The resulting inhibitory cytokines in the TME are believed to limit CAR cell function and expansion. Thus, TGF-β could limit the efficacy of therapeutic engineered T cells.

Since TGF-β Receptors are responsible for transmitting the intracellular, suppressive pSMAD signaling, a therapeutic strategy focused on modified TGF-β R1 and TGF-βRII constructs has potential. Furthermore, using such constructs in existing or new TCR and CAR therapies may enhance the ability of these cell therapies to target cancers. Thus, described herein are dominant-negative TGF-β Receptors that may be used to modulate TGF-β signaling. In some aspects, the dominant-negative TGF-β Receptors may be co-expressed with a TCR or CAR construct to limit the suppressive effects of TGF-β in the TME.

The present disclosure contemplates the use of the DN TGF-β Receptor constructs described herein with engineered T cell receptors (TCRs) used in T cell immunotherapy. Libraries of TCRs may be screened for their selectivity to target antigens. In this manner, natural TCRs, which have a high avidity and reactivity toward target antigens may be selected, cloned, and subsequently introduced into a population of T cells used for adoptive immunotherapy. A T cell with an engineered TCR that also expresses the DN TGF-β Receptor constructs described herein would not only be able to target specific antigens due to TCR specificity, but would also protect the T-cell from the suppressive effects of TGF-β. Thus, combining TCRs with the DN TGF-β Receptor constructs described herein may provide a way to maintain the therapeutic effect of adoptive T cell immunotherapy. In one embodiment described herein, the DN TGF-B Receptors described herein are co-expressed with a TCR.

In one embodiment described herein, T cells are modified by introducing a polynucleotide encoding subunit of a TCR that may form TCRs that confer specificity to T cells for tumor cells expressing a target antigen. In some embodiments, the subunits have one or more amino acid substitutions, deletions, insertions, or modifications compared to the naturally occurring subunit, so long as the subunits retain the ability to form TCRs conferring upon transfected T cells the ability to home to target cells, and participate in immunologically-relevant cytokine signaling. The engineered TCRs may also bind target cells displaying the relevant tumor-associated peptide with high avidity, and optionally mediate efficient killing of target cells presenting the relevant peptide in vivo.

The nucleic acids encoding engineered TCRs may be isolated from their natural context in a (naturally-occurring) chromosome of a T cell, and may be incorporated into suitable vectors as described elsewhere herein. Both the nucleic acids and the vectors comprising them may be transferred into a cell, which cell may be a T cell. The modified T cells are then able to express one or more chains of a TCR (and in some aspects two chains) encoded by the transduced nucleic acid or nucleic acids. In some embodiments, the engineered TCR is an exogenous TCR because it is introduced into T cells that do not normally express the introduced TCR. The essential aspect of the engineered TCRs is that it has high avidity for a tumor antigen presented by a major histocompatibility complex (MHC) or similar immunological component. In contrast to engineered TCRs, CARs are engineered to bind target antigens in an MHC independent manner.

The protein encoded by the nucleic acids described herein may be expressed with additional polypeptides attached to the amino-terminal or carboxyl-terminal portion of the α-chain or the β-chain of a TCR so long as the attached additional polypeptide does not interfere with the ability of the α-chain or the β-chain to form a functional T cell receptor and the MHC dependent antigen recognition.

Antigens that are recognized by the engineered TCRs contemplated herein include, but are not limited to cancer antigens, including antigens on both hematological cancers and solid tumors and viral induced cancers. TCR therapy for the treatment of HPV induced cervical carcinoma is an area of interest that holds promise. The oncolytic proteins HPV-16 E6 and HPV-16 E7 may thus be potential target antigens for use with TCR.

Other illustrative antigens include, but are not limited HPV oncoproteins, including HPV-16 E6 and HPV-16 E7, alpha folate receptor, 5T4, αvβ6 integrin, BCMA, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, FAP, fetal AchR, FRa, GD2, GD3, Glypican-3 (GPC3), HLA-A1+MAGEI, HLA-A2+MAGE1, HLAA3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Mud, Muc16, NCAM, NKG2D Ligands, NY-ESO-1, PRAME, PSCA, PSMA, RORI, SSX, Survivin, TAG72, TEMs, and VEGFRII.

Combining any TCR construct as described herein with the DN TGF-β Receptors of the present disclosure may restore, maintain or enhance the therapeutic effect of TCR therapy challenged by TGF-β suppression. Thus, in one embodiment described herein, the DN TGF-β Receptors are co-expressed in a T cell with a TCR directed against HPV. In another embodiment described herein, the DN TGF-β Receptors are co-expressed in a T cell with a TCR directed against the HPV-16 E6 protein. In another embodiment described herein, the DN TGF-Receptors are co-expressed in a T cell with a TCR directed against the HPV-16 E7 protein.

T cells may also be genetically engineered with vectors designed to express CARs that redirect cytotoxicity toward tumor cells. CARs are molecules that combine antibody based specificity for a target antigen (e.g., tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins. The present disclosure contemplates the use of the DN TGF-β Receptors described herein with chimeric antigen receptors (CARs). Like with the use of TCRs, co-expression of the DN TGF-β Receptors with a CAR may promote CAR expansion and protect, and in some cases restore, CAR therapies challenged by TGF-β suppression. In one embodiment described herein, the DN TGF-β Receptors are co-expressed with the CARs described herein.

The CARs contemplated herein comprise an extracellular domain that binds to a specific target antigen (also referred to as a binding domain or antigen-specific binding domain), a transmembrane domain and an intracellular signaling domain. The main characteristic of CARs are their ability to redirect immune effector cell specificity, thereby triggering proliferation, cytokine production, phagocytosis or production of molecules that may mediate cell death of the target antigen expressing cell in a major histocompatibility (MHC) independent manner, exploiting the cell specific targeting abilities of monoclonal antibodies, soluble ligands or cell specific co-receptors.

In some embodiments, a CAR comprises an extracellular binding domain including but not limited to an antibody or antigen binding fragment thereof, a tethered ligand, or the extracellular domain of a co-receptor, that specifically binds a target antigen.

By way of non-limiting examples, target antigens may include: HPV oncoproteins, including HPV-16 E6 and HPV-16 E7, alpha folate receptor, 5T4, integrin, BCMA, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, FAP, fetal AchR, FRa, GD2, GD3, Glypican-3 (GPC3), HLA-A1+MAGEI, HLA-A2+MAGE1, HLAA3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Mud, Muc16, NCAM, NKG2D Ligands, NYE-S0-1, PRAME, PSCA, PSMA, RORI, SSX, Survivin, TAG72, TEMs, and VEGFRII; one or more hinge domains or spacer domains; a transmembrane domain including, but not limited to, transmembrane domains from CD8α, CD4, CD45, PD-1, and CD152; one or more intracellular costimulatory signaling domains including but not limited to intracellular costimulatory signaling domains from CD28, CD54 (ICAM), CD134 (OX40), CD137 (41BB), CD152 (CTLA4), CD273 (PD-L2), CD274 (PD-L1), and CD278 (ICOS); and a primary signaling domain from CD3ζ or FcRγ. In one embodiment described herein, the CAR binds to a tumor antigen comprising CLL-1, CD19, CD20, CD28, CD137 (4-1BB), Glypican-3 (GPC3), PSCA or PSMA.

A hinge may be derived from a natural source or from a synthetic source. In some embodiments, an Antigen binding system of the present disclosure may comprise a hinge that is, is from, or is derived from (e.g., comprises all or a fragment of) CD2, CD3 delta, CD3 epsilon, CD3 gamma, CD4, CD7, CD8.alpha., CD8.beta., CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TN-FRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA1-1, SLAMF9, LAT, GADS (GrpL), SLP-76 (LCP2), PAG1/CBP, a CD83 ligand, Fc gamma receptor, WIC class 1 molecule, MHC class 2 molecule, a TNF receptor protein, an immunoglobulin protein, a cytokine receptor, an integrin, activating NK cell receptors, or Toll ligand receptor, or which is a fragment or combination thereof. In certain embodiments, a CAR does not comprise a CD28 hinge.

A transmembrane domain may be derived either from a natural or from a synthetic source. Where the source is natural, a domain may be derived from any membrane-bound or transmembrane protein. Exemplary transmembrane domains may be derived from (e.g., may comprise at least a transmembrane domain of) an alpha, beta or zeta chain of a T cell receptor, CD28, CD3 epsilon, CD3 delta, CD3 gamma, CD45, CD4, CD5, CD7, CD8, CD8 alpha, CD8beta, CD9, CD11a, CD11b, CD11c, CD11d, CD16, CD22, CD27, CD33, CD37, CD64, CD80, CD86, CD134, CD137, TNFSFR25, CD154, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD276 (B7-H3), CD29, CD30, CD40, CD49a, CD49D, CD49f, CD69, CD84, CD96 (Tactile), CD5, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that binds with CD83, LIGHT, LIGHT, LTBR, Ly9 (CD229), lymphocyte function-associated antigen-1 (LFA-1; CD1-1a/CD18), WIC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. In some embodiments, a transmembrane domain may be synthetic (and can, e.g., comprise predominantly hydrophobic residues such as leucine and valine). In some embodiments, a triplet of phenylalanine, tryptophan and valine are comprised at each end of a synthetic transmembrane domain. In some embodiments, a transmembrane domain is directly linked or connected to a cytoplasmic domain. In some embodiments, a short oligo- or polypeptide linker (e.g., between 2 and 10 amino acids in length) may form a linkage between a transmembrane domain and an intracellular domain. In some embodiments, a linker is a glycine-serine doublet.

In some embodiments, a signaling domain and/or activation domain comprises an immunoreceptor tyrosine-based activation motif (ITAM). Examples of ITAM containing cytoplasmic signaling sequences comprise those derived from TCR zeta, FcR gamma, FcR beta, CD3 zeta, CD3 gamma, CD3 delta, CD3 epsilon, CD5, CD22, CD79a, CD79b, and CD66d (see, e.g., Love et al., Cold Spring Harb. Perspect. Biol. 2:a002485 (2010); Smith-Garvin et al., Annu. Rev. Immunol. 27:591-619 (2009)).

In certain embodiments, suitable signaling domains comprise, without limitation, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11 a, CD11b, CD11 c, CD11d, CD5, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that binds with CD83, LIGHT, LIGHT, LTBR, Ly9 (CD229), Ly108), lymphocyte function-associated antigen-1 (LFA-1; CD1-1a/CD18), MEW class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

A CAR may comprise a costimulatory signaling domain, e.g., to increase signaling potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Annu. Rev. Pharmacol. Toxicol. 56:59-83 (2016). Signals generated through a TCR alone may be insufficient for full activation of a T cell and a secondary or co-stimulatory signal may increase activation. Thus, in some embodiments, a signaling domain further comprises one or more additional signaling domains (e.g., costimulatory signaling domains) that activate one or more immune cell effector functions (e.g., a native immune cell effector function described herein). In some embodiments, a portion of such costimulatory signaling domains may be used, as long as the portion transduces the effector function signal. In some embodiments, a cytoplasmic domain described herein comprises one or more cytoplasmic sequences of a T cell co-receptor (or fragment thereof). Non-limiting examples of such T cell co-receptors comprise CD27, CD28, 4-1BB (CD137), OX40, CD30, CD40, PD-1, ICOS, lymphocyte function-associated antigen-1 (LFA-1), MYD88, CD2, CD7, LIGHT, NKG2C, B7-H3, and a ligand that binds with CD83.

In some embodiments, the CARs contemplated herein comprise an extracellular binding domain that specifically binds to a target polypeptide, e.g., target antigen, expressed on tumor cell. As used herein, the terms, "binding domain," "extracellular domain," "extracellular binding domain," "antigen-specific binding domain," "antigen binding domain" and "extracellular antigen specific binding domain," are used interchangeably and provide a CAR with the ability to specifically bind to the target antigen of interest. A binding domain may comprise any protein, polypeptide, oligopeptide, or peptide that possesses the ability to specifically recognize and bind to a biological molecule (e.g., a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest.

In some embodiments, the extracellular binding domain of a CAR comprises an antibody or antigen binding fragment thereof. An "antibody" refers to a binding agent that is a polypeptide comprising at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments thereof. The term also includes genetically engineered forms such as chimeric antibodies (for example, humanized murine antibodies), hetero-conjugate antibodies (such as, bispecific antibodies) and antigen binding fragments thereof. See also, *Pierce Catalog and Handbook*, 1994-1995 (Pierce Chemical Co., Rockford, IL); Kuby, J., *Immunology*, 3rd Ed., W. H. Freeman & Co., New York, 1997.

In some embodiments, the target antigen is an epitope of an HPV oncoproteins, including HPV-16 E6 and HPV-16 E7, alpha folate receptor, 5T4, integrin, BCMA, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, F AP, fetal AchR, FRa, GD2, GD3, Glypican-3 (GPC3), HLA-A1+ MAGEI, HLA-A2+MAGE1, HLAA3+MAGE1, HLA-A1+ NY-ESO-1, HLA-A2+NY-ESO-1, HLA-A3+NY-ESO-1, IL-11Rα, IL-13Rα2, Lambda, Lewis-Y, Kappa, Mesothelin, Mud, Muc16, NCAM, NKG2D Ligands, NYE-S0-1, PRAME, PSCA, PSMA, RORI, SSX, Survivin, TAG72, TEMs, and VEGFRII polypeptide. In one embodiment described herein, the CAR binds to a tumor antigen epitope comprising CD19, CD20, CD28, CD137 (4-1BB), CLL-1, Glypican-3 (GPC3), PSCA or PSMA.

Hepatocellular carcinoma (HCC) is one of the most common cancers worldwide (El-Serag, *J Clin Gastroenterology* 35:S72-78 (2002)). Unlike any other tumor antigen associated with hepatocellular carcinoma to date, GPC3 is a glycophosphatidylinositiol-linked membrane-associated protein with a large extracellular domain attractive for antibody-directed therapy. Thus, the large extracellular domain and the relative specific expressions of GPC3 on cell surface of malignant HCC tissues make it an attractive target for HCC tumor immunotherapy. Thus, one embodiment contemplated by the present disclosure is a CAR directed to GPC3 for use with the DN TGF-β Receptors described herein.

In one embodiment described herein the CAR comprises the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 37.

```
                                            (SEQ ID NO: 37)
DIVNITQSPDSLAVSLGERATINCKSSQSLLYSSNQKNYLAWYQQKPGQ

PPKLLIYWASSRESGVPDRFSGSGSGTDFTLTISSLQAEDVAVYYCQQY

YNYPLTFGQGTKLEIKGSTSGSGKPGSGEGSTKGEVQLVESGGGLVQPG

GSLRLSCAASGFTFNKNAMNWVRQAPGKGLEWVGRIRNKTNNYATYYAD

SVKARFTISRDDSKNSLYLQMNSLKTEDTAVYYCVAGNSFAYWGQGTLV

TVSSGSTTTPAPRPPTPAPTIASQPLSLRPEACRPAAGGAVHTRGLDFA

CDIYIWAPLAGTCGVLLLSLVITLYCKRGRKKLLYIFKQPFMRPVQTTQ

EEDGCSCRFPEEEEGGCELRVKFSRSADAPAYQQGQNQLYNELNLGRRE

EYDVLDKRRGRDPEMGGKPRRKNPQEGLYNELQKDKMAEAYSEIGMKGE

RRRGKGHDGLYQGLSTATKDTYDALHMQALPPR.
```

"Single-chain Fv" or "scFv" antibody fragments comprise the VH and VL domains of antibody, wherein these domains are present in a single polypeptide chain and in either orientation (e.g., VL-VH or VH-VL). Generally, the scFv polypeptide further comprises a polypeptide linker between the VH and VL domains which enables the scFv to form the desired structure for antigen binding. For a review of scFv, see, e.g., Pluckthin, in *The Pharmacology of Monoclonal Antibodies*, vol. 113, Rosenburg and Moore eds., (Springer-Verlag, New York, 1994), pp. 269-315. In one embodiment described herein, the CARs described herein comprise a VH domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 38.

```
                                            (SEQ ID NO: 38)
EVQLVESGGGLVQPGGSLRLSCAASGFTFNKNAMNWVRQAPGKGLEWVG

RIRNKTNNYATYYADSVKARFTISRDDSKNSLYLQMNSLKTEDTAVYYC

VAGNSFAYWGQGTLVTVSS.
```

In another embodiment described herein, the CARs described herein comprise a VL domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 39.

```
                                            (SEQ ID NO: 39)
DIVMTQSPDSLAVSLGERATINCKSSQSLLYSSNQKNYLAWYQQKPGQP

PKLLIYWASSRESGVPDRFSGSGSGTDFTLTISSLQAEDVAVYYCQQYY

NYPLTFGQGTKLEIK.
```

In some embodiments, a CAR contemplated herein comprises antigen-specific binding domain that may be a scFv (a murine, human or humanized scFv) that binds an antigen expressed on a cancer cell. In a certain embodiment, the scFv binds HPV oncoproteins, including HPV-16 E6 and HPV-16 E7, alpha folate receptor, 5T4, integrin, BCMA, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, F AP, fetal AchR, FRa, GD2, GD3, Glypican-3 (GPC3), HLA-A1+MAGEI, HLA-A2+MAGE1, HLAA3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Mud, Muc16, NCAM, NKG2D Ligands, NYE-S0-1, PRAME, PSCA, PSMA, RORI, SSX, Survivin, TAG72, TEMs, and VEGFRII. In other embodiment described herein, the CAR comprises antigen specific binding domains scFv that bind CD19, CD20, CD28, CD137 (4-1BB), CLL-1, Glypican-3 (GPC3), PSCA or PSMA.

In certain embodiments, the CARs contemplated herein may comprise linker residues between the various domains, e.g., between VH and VL domains, added for appropriate spacing conformation of the molecule. CARs contemplated herein, may comprise one, two, three, four, or five or more linkers. In some embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers (G)n; glycine-serine polymers $(G_{1-5}S_{1-5})n$, where n is an integer of at least one, two, three, four, or five; glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs described herein. Glycine accesses more phi-psi space than even alanine, and is much less restricted than residues with longer side chains (see Scheraga, Rev. Computational Chem. 11173-142 (1992)). Other linkers contemplated herein include Whitlow linkers (see Whitlow, Protein Eng. 6(8): 989-95 (1993)). The ordinarily skilled artisan will recognize that design of a CAR in some embodiments may include linkers that are all or partially flexible, such that the linker may include a flexible linker as well as one or more portions that confer less flexible structure to provide for a desired CAR structure. In one embodiment, any of the constructs described herein may comprise a "GS" linker. In another embodiment, any of the constructs described herein comprise a "GSG" linker. In another embodiment, the CARs described herein comprise the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 40. GSTSGSGKPGSGEGSTKG (SEQ ID NO: 40).

In other embodiments, a CAR comprises a scFv that further comprises a variable region linking sequence. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In one embodiment, the variable region linking sequence is 1, 2, 3, 4, 5, 6, 7, 8, 9, 10, 11, 12, 13, 14, 15, 16, 17, 18, 19, 20, 21, 22, 23, 24, 25, or more amino acids long.

In other embodiments, the binding domain of the CAR is followed by one or more "spacer domains," which refers to the region that moves the antigen binding domain away from the effector cell surface to enable proper cell/cell contact, antigen binding and activation (Patel et al., Gene Therapy, 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain may include the amino acid sequence of a naturally occurring immunoglobulin hinge region or an altered immunoglobulin hinge region.

The binding domain of the CAR may generally be followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain. The hinge domain may be derived either from a natural, synthetic, semi-synthetic, or recombinant source. The hinge domain may include the amino acid sequence of a naturally occurring immunoglobulin hinge region or an altered immunoglobulin hinge region.

Illustrative hinge domains suitable for use in the CARs described herein include the hinge region derived from the extracellular regions of type 1 membrane proteins such as CD8α, CD4, CD28 and CD7, which may be wild-type hinge regions from these molecules or may be altered, for example a truncated CD28 hinge domain. A hinge may be derived from a natural source or from a synthetic source. In some embodiments, an Antigen binding system of the present disclosure may comprise a hinge that is, is from, or is derived from (e.g., comprises all or a fragment of) CD2, CD3 delta, CD3 epsilon, CD3 gamma, CD4, CD7, CD8.alpha., CD8.beta., CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA1-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, or which is a fragment or combination thereof. In certain embodiments, a CAR does not comprise a CD28 hinge. In another embodiment, the hinge domain comprises a CD8α hinge region. In one embodiment the CARs described herein comprise a hinge domain from CD8α having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 41. TTTPAPRPPTPAPTIA-SQPLSLRPEACRPAAGGAVHTRGLDFACD (SEQ ID NO: 41).

The "transmembrane domain" is the portion of the CAR that fuses the extracellular binding portion and intracellular signaling domain and anchors the CAR to the plasma membrane of the immune effector cell. Exemplary transmembrane domains may be derived from (e.g., may comprise at least a transmembrane domain of) an alpha, beta or zeta chain of a T cell receptor, CD28, CD3 epsilon, CD3 delta, CD3 gamma, CD45, CD4, CD5, CD7, CD8, CD8 alpha, CD8beta, CD9, CD11a, CD11b, CD11c, CD11d, CD16, CD22, CD27, CD33, CD37, CD64, CD80, CD86, CD134, CD137, TNFSFR25, CD154, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD276 (B7-H3), CD29, CD30, CD40, CD49a, CD49D, CD49f, CD69, CD84, CD96 (Tactile), CD5, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that binds with CD83, LIGHT, LIGHT, LTBR, Ly9 (CD229), lymphocyte function-associated antigen-1 (LFA-1; CD1-1a/CD18), WIC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. In some embodiments, a transmembrane domain may be synthetic (and can, e.g., comprise predominantly hydrophobic residues such as leucine and valine). In some embodiments, a triplet of phenylalanine, tryptophan and valine are comprised at each end of a synthetic transmembrane domain. In some embodiments, a transmembrane domain is directly linked or connected to a cytoplasmic domain. In some embodiments, a short oligo- or polypeptide linker (e.g., between 2 and 10 amino acids in length) may form a linkage between a transmembrane domain and an intracellular domain. In some embodiments, a linker is a glycine-serine doublet. In one embodiment, the CARs described herein comprise a transmembrane domain from CD8α having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 42. IYIWAPLAGTCGVLLLSLVITLYC (SEQ ID NO: 42).

In some embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. In some embodiments, a signaling domain and/or activation domain comprises an immunoreceptor tyrosine-based activation motif (ITAM). Examples of ITAM containing cytoplasmic signaling sequences comprise those derived from TCR zeta, FcR gamma, FcR beta, CD3 zeta, CD3 gamma, CD3 delta, CD3 epsilon, CD5, CD22, CD79a, CD79b, and CD66d (see, e.g., Love et al., Cold Spring Harb. Perspect. Biol. 2:a002485 (2010); Smith-Garvin et al., Annu. Rev. Immunol. 27:591-619 (2009)). In certain embodiments, suitable signaling domains comprise, without limitation, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CD5, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain may be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal may also be required. Thus, T cell activation may be said to be mediated by two distinct classes of intracellular signaling domains: primary signaling domains that initiate antigen-dependent primary activation through the TCR (e.g., a TCR/CD3 complex) and costimulatory signaling domains that act in an antigen independent manner to provide a secondary or costimulatory signal. In some embodiments, a CAR contemplated herein comprises an intracellular signaling domain that comprises one or more "costimulatory signaling domain" and a "primary signaling domain."

Illustrative examples of ITAM containing primary signaling domains that are useful in the present disclosure include those derived from TCRζ, FcRγ, FcRβ, DAP12, CD3γ, CD3δ, CD3ε, CD3ζ, CD22, CD79a, CD79b, and CD66d. In some embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain. In one embodiment, the CARs have a CD3ζ domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 43.

(SEQ ID NO: 43)
LRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTAT

KDTYDALHMQALPPR.

CARs contemplated herein comprise one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule. In some embodiments, costimulatory molecules may include CD27, CD28, CD137 (4-IBB), OX40 (CD134), CD30, CD40, PD-I, ICOS (CD278), CTLA4, LFA-1, CD2, CD7, LIGHT, TRIM, LCK3, SLAM, DAPIO, LAG3, HVEM, and NKD2C, and CD83. In one embodiment, the CARs described herein comprise a 4-IBB costimulatory domain having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 44.

(SEQ ID NO: 44)
KRGRKKLLYIFKQPFMRPVQTTQEEDGCSCRFPEEEEGGCE.

The engineered CARs described herein may also comprise an N-terminal signal peptide or tag at the N-terminus of the scFv or antigen binding domain. In one embodiment, a heterologous signal peptide may be used. The antigen binding domain or scFV may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as the CAR constructs described herein, are generally expressed at the cell surface as a mature protein lacking the signal peptide, whereas the precursor form of the polypeptide includes the signal peptide. Any suitable signal sequence known in the art may be used. Similarly any known tag sequence known in the art may also be used.

In one embodiment described herein, the CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 45.

(SEQ ID NO: 45)
EQKLISEEDLDIVMTQSPDSLAVSLGERATINCKSSQSLLYSSNQKNYLA

WYQQKPGQPPKLLIYWASSRESGVPDRFSGSGSGTDFTLTISSLQAEDVA

VYYCQQYYNYPLTFGQGTKLEIKGSTSGSGKPGSGEGSTKGEVQLVESGG

GLVQPGGSLRLSCAASGFTFNKNAMNWVRQAPGKGLEWVGRIRNKTNNYA

TYYADSVKARFTISRDDSKNSLYLQMNSLKTEDTAVYYCVAGNSFAYWGQ

GTLVTVSSGSTTTPAPRPPTPAPTIASQPLSLRPEACRPAAGGAVHTRGL

DFACDIYIWAPLAGTCGVLLLSLVITLYCKRGRKKLLYIFKQPFMRPVQT

TQEEDGCSCRFPEEEEGGCELRVKFSRSADAPAYQQGQNQLYNELNLGRR

EEYDVLDKRRGRDPEMGGKPRRKNPQEGLYNELQKDKMAEAYSEIGMKGE

RRRGKGHDGLYQGLSTATKDTYDALHMQALPPR.

Combining any CAR constructs as described herein with any of the DN TGF-β Receptors of the present disclosure may restore, maintain or enhance the therapeutic effect of CAR T therapy challenged by TGF-β suppression. Thus, in one embodiment described herein, the DN TGF-β Receptors described herein are co-expressed in a T cell with a CAR, forming a "CAR-DN TGF-β Receptor construct". In another embodiment described herein, any of the DN TGF-β Receptors are co-expressed in a T cell with a CAR that binds to antigens including but not limited to BCMA, CD19, CD20, CD28, CD137 (4-1BB), CLL-1, Glypican-3 (GPC3), PSCA or PSMA. In another embodiment described herein the CAR portion of a CAR-DN TGF-β Receptor construct comprises the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 37 or SEQ ID NO: 45. In another embodiment described herein, the DN TGF-β Receptor portion of a CAR-DN TGF-β Receptor construct comprises the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 10 or SEQ ID NO: 14.

To facilitate efficient expression of a CAR-DN TGF-β Receptor construct in a T cell as described herein, self-cleaving sequences may be used to enable co-expression of multiple gene constructs in equal amounts by expressing them in one open reading frame. Any suitable cleaving peptide sequence may be used with the constructs described herein, for example, 2A cleavable peptides (for example T2A), 2A-like linkers or functional equivalents thereof and combinations thereof. In some embodiments, the linkers include the picornaviral 2A-like linker, CHYSEL sequences of porcine teschovirus (P2A), virus (T2A) or combinations, variants and functional equivalents thereof. In one embodiment described herein, the CAR-DN TGF-β Receptor construct comprises a self-cleaving domain having an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 46. EGRGSLLTCGDVEENPGP (SEQ ID NO: 46).

In one embodiment, the CAR-DN TGF-β Receptor construct described herein comprises the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 47.

```
                                            (SEQ ID NO: 47)
DIVMTQSPDSLAVSLGERATINCKSSQSLLYSSNQKNYLAWYQQKPGQPP

KLLIYWASSRESGVPDRFSGSGSGTDFTLTISSLQAEDVAVYYCQQYYNY

PLTFGQGTKLEIKGSTSGSGKPGSGEGSTKGEVQLVESGGGLVQPGGSLR

LSCAASGFTFNKNAMNWVRQAPGKGLEWVGRIRNKTNNYATYYADSVKAR

FTISRDDSKNSLYLQMNSLKTEDTAVYYCVAGNSFAYWGQGTLVTVSSGS

TTTPAPRPPTPAPTIASQPLSLRPEACRPAAGGAVHTRGLDFACDIYIWA

PLAGTCGVLLLSLVITLYCKRGRKKLLYIFKQPFMRPVQTTQEEDGCSCR

FPEEEEGGCELRVKFSRSADAPAYQQGQNQLYNELNLGRREEYDVLDKRR

GRDPEMGGKPRRKNPQEGLYNELQKDKMAEAYSEIGMKGERRRGKGHDGL

YQGLSTATKDTYDALHMQALPPRGSGEGRGSLLTCGDVEENPGPMGRGLL

RGLWPLHIVLWTRIASTIPPHVQKSVNNDMIVTDNNGAVKFPQLCKFCDV

RFSTCDNQKSCMSNCSITSICEKPQEVCVAVWRKNDENITLETVCHDPKL

PYHDFILEDAASPKCIMKEKKKPGETFFMCSCSSDECNDNIIFSEEYNTS

NPDLLLVIFQVTGISLLPPLGVAISVIIIFYCYRVNRQ.
```

In one embodiment described herein, polynucleotides encoding one or more DN TGF-β Receptors or CAR-DN TGF-β Receptor construct polypeptides contemplated herein are provided. As used herein, the terms "polynucleotide" or "nucleic acid" refers to messenger RNA (mRNA), RNA, genomic RNA (gRNA), plus strand RNA (RNA(+)), minus strand RNA (RNA(−)),complementary DNA (cDNA) or recombinant DNA. Polynucleotides include single and double stranded polynucleotides. Polynucleotides of the disclosure include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. In various illustrative embodiments, the present disclosure contemplates, in part, polynucleotides comprising expression vectors, viral vectors, and transfer plasmids, and compositions, and cells comprising the same.

In some embodiments, polynucleotides are provided by this disclosure that encode at least about 5, 10, 25, 50, 100, 150, 200, 250, 300, 350, 400, 500, 1000, 1250, 1500, 1750, or 2000 or more contiguous amino acid residues of a polypeptide of the disclosure, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions may be made to a reference polynucleotide whereby the expressed altered polynucleotide retains the biological function or activity of the reference polynucleotide.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

The polynucleotides described herein, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, where the total length may be limited by the ease of preparation and use in the intended recombinant DNA protocol.

Polynucleotides may be prepared, manipulated and/or expressed using any of a variety of well-established techniques known and available in the art. In order to express a desired polypeptide, a nucleotide sequence encoding the polypeptide, may be inserted into appropriate vector. Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pCIneo vectors (Promega) for expression in mammalian cells; pLenti4N5-DEST™, pLenti6N5-DEST™, and pLenti6.2N5-GW/lacZ (Invitrogen) for lentivirus-mediated gene transfer and expression in mammalian cells. In some embodiments, the coding sequences of the chimeric proteins disclosed herein may be ligated into such expression vectors for the expression of the chimeric protein in mammalian cells.

The "control elements" or "regulatory sequences" present in an expression vector are those non-translated regions of the vector-origin of replication, selection cassettes, promoters, enhancers, translation initiation signals (Shine Dalgarno sequence or Kozak sequence), introns, a polyadenylation sequence, 5' and 3' untranslated regions-which interact with host cellular proteins to carry out transcription and translation. Such elements may vary in their strength and specificity. Depending on the vector system and host utilized, any number of suitable transcription and translation elements, including ubiquitous promoters and inducible promoters maybe used.

In other embodiments, a vector for use in practicing the embodiments described herein including, but not limited to expression vectors and viral vectors, will include exogenous, endogenous, or heterologous sequences such as promoters and/or enhancers. An "endogenous" control sequence is one which is naturally linked with a given gene in the genome. An "exogenous" control sequence is one which is placed in juxtaposition to a gene by means of genetic manipulation (i.e., molecular biological techniques) such that transcription of that gene is directed by the linked enhancer/promoter. A "heterologous" sequence is an exogenous sequence that may be from a different protein of the same species or a different species than the protein or cell being genetically manipulated.

The term "promoter" as used herein refers to a recognition site of a polynucleotide (DNA or RNA) to which an RNA polymerase binds. An RNA polymerase initiates and transcribes polynucleotides operably linked to the promoter. In some embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances may function independent of their orientation relative to another control sequence. An enhancer may function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide—of interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively. The present disclosure contemplates the use of any suitable cell line for use with the various constructs described herein including, but not limited to: CHO cells, BHK cells, MDCK cells, C3H 10T1/2 cells, FLY cells, Flp-cells, Psi-2 cells, BOSC 23 cells, P A317 cells, WEHI cells, COS cells, BSC 1 cells, BSC 40 cells, BMT 10 cells, Jurkat cells, VERO cells, W138 cells, MRCS cells, A549 cells, HTI080 cells, Hep cells, HEK cells, iHPC cells, 293 cells, 293T cells, B-50 cells, 3T3 cells, NIH3T3 cells, NK cells, HepG2 cells, Saos-2 cells, Huh7 cells, HeLa cells, W163 cells, 211 cells, and 211A cells or any other suitable cell line.

Illustrative ubiquitous expression control sequences suitable for use in some embodiments of the disclosure include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, HS, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B 1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-I (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) promoter (Challita et al., *J Virol.* 69(2):748-55 (1995)).

In another embodiment described herein, it may be desirable to co-express a polynucleotide comprising an the DN TGF-β Receptors described herein with an engineered TCR or CAR, from a promoter that provides stable and long-term expression in T cells and at sufficient levels to redirect the T cells to cells expressing the target antigen.

As used herein, "conditional expression" may refer to any type of conditional expression including, but not limited to, inducible expression; repressible expression; expression in cells or tissues having a physiological, biological, or disease state, etc. This definition is not intended to exclude cell type or tissue specific expression. Certain embodiments described herein provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene,* 323:67), the cumate inducible gene switch (WO 2002/088346), tetracycline-dependent regulatory systems, etc.

Conditional expression may also be achieved by using a site specific DNA recombinase. According to certain embodiments of the disclosure the vector comprises at least one (typically two) site(s) for recombination mediated by a site specific recombinase. As used herein, the terms "recombinase" or "site specific recombinase" include excisive or integrative proteins, enzymes, cofactors or associated proteins that are involved in recombination reactions involving one or more recombination sites (e.g., two, three, four, five, seven, ten, twelve, fifteen, twenty, thirty, fifty, etc.), which may be wild-type proteins (see Landy, *Current Opinion in Biotechnology* 3:699-707 (1993)), or mutants, derivatives (e.g., fusion proteins containing the recombination protein sequences or fragments thereof), fragments, and variants thereof. Illustrative examples of recombinases suitable for use in some embodiments of the present disclosure include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The present disclosure contemplates, co-expression of polynucleotides comprising the engineered DN TGF-β Receptors described herein with engineered TCR and CAR polypeptides constructs, including CAR-DN TGF-β Receptor constructs as described herein, and fragments thereof, cells and compositions comprising the same, and vectors that express polypeptides. "Polypeptide," "polypeptide fragment," "peptide" and "protein" are, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. In various embodiments, the polypeptides contemplated herein comprise a signal (or leader) sequence at the N-terminal end of the protein, which co-translationally or post-translationally directs transfer of the protein. Illustrative examples of suitable signal sequences useful in disclosed herein include, but are not limited to the IgG 1 heavy chain signal sequence and the CD8α signal sequence. Polypeptides may be prepared using any of a variety of well-known recombinant and/or synthetic techniques. Polypeptides contemplated herein specifically include the engineered, DN TGF-β Receptors, engineered TCRs and CARs of the present disclosure, or sequences that have deletions from, additions to, and/or substitutions of one or more amino acid of a polypeptide as contemplated herein.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in some embodiments, it may be desirable to improve the binding affinity and/or other biological properties of the engineered DN TGF-β Receptors, TCRs or CARs by introducing one or more substitutions, deletions, additions and/or insertions. Preferably, polypeptides of the disclosure include polypeptides having at least about 50%, 60%, 65%, 70%, 75%, 85%, 90%, 95%, 98%, or 99% amino acid identity thereto. Polypeptides of the disclosure include variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. Polypeptides include "polypeptide fragments." Polypeptide fragments refer to a polypeptide, which may be monomeric or multi-meric that has an amino-terminal deletion, a carboxyl-terminal deletion, and/or an internal deletion or substitution of a naturally-occurring or recombinantly-produced polypeptide. In certain embodiments, a polypeptide fragment may comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long.

The polypeptide may also be fused in-frame or conjugated to a linker or other sequence for ease of synthesis, purification or identification of the polypeptide (e.g., poly-His), or to enhance binding of the polypeptide to a solid support.

As noted above, polypeptides of the present disclosure may be altered in various ways including amino acid substitutions, deletions, truncations, and insertions. Methods for such manipulations are generally known in the art. For example, amino acid sequence variants of a reference polypeptide may be prepared by mutations in the DNA. Methods for mutagenesis and nucleotide sequence alterations are well known in the art. See, for example, Kunkel (1985, *Proc. Natl. Acad. Sci. USA*. 82: 488-492), Kunkel et al., (1987, *Methods in Enzymol*, 154: 367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present disclosure and still obtain a functional molecule that encodes a variant or derivative polypeptide with desirable characteristics.

Polypeptide variants further include glycosylated forms, aggregative conjugates with other molecules, and covalent conjugates with unrelated chemical moieties (e.g., pegylated molecules). Covalent variants may be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

Where expression of two or more polypeptides is desired, the polynucleotide sequences encoding them may be separated by an IRES sequence as discussed elsewhere herein. In another embodiment, two or more polypeptides may be expressed as a fusion protein that comprises one or more self-cleaving polypeptide sequences.

Polypeptides of the present disclosure include fusion polypeptides. In some embodiments, fusion polypeptides and polynucleotides encoding fusion polypeptides are provided. Fusion polypeptides and fusion proteins refer to a polypeptide having at least two, three, four, five, six, seven, eight, nine, or ten or more polypeptide segments. Fusion polypeptides are typically linked C-terminus to N-terminus, although they may also be linked C-terminus to C-terminus, N-terminus to N-terminus, or N-terminus to C-terminus. The polypeptides of the fusion protein may be in any order or a specified order. Fusion polypeptides or fusion proteins may also include conservatively modified variants, polymorphic variants, alleles, mutants, subsequences, and interspecies homologs, so long as the desired transcriptional activity of the fusion polypeptide is preserved. Fusion polypeptides may be produced by chemical synthetic methods or by chemical linkage between the two moieties or may generally be prepared using other common techniques. Ligated DNA sequences comprising the fusion polypeptide are operably linked to suitable transcriptional or translational control elements as discussed elsewhere herein.

In one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments or to facilitate transport of the fusion protein through the cell membrane.

Fusion polypeptides may further comprise a polypeptide cleavage signal between each of the polypeptide domains described herein. In addition, polypeptide site may be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic,* 5(8); 616-26).

Suitable protease cleavages sites and self-cleaving peptides are known to the skilled person (see, e.g., in Ryan et al., 1997. *J Gener. Viral.* 78, 699-722; Scymczak et al. (2004) *Nature Biotech.* 5, 589-594). Exemplary protease cleavage sites include, but are not limited to the cleavage sites of potyvirus Nia proteases (e.g., tobacco etch virus protease), potyvirus HC proteases, potyvirus P1 (P35) proteases, byovirus Nia proteases, byovirus RNA-2-encoded proteases, aphthovirus L proteases, enterovirus 2A proteases, rhinovirus 2A proteases, picoma 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites may be used. In other embodiments, self-cleaving peptides may include those polypeptide sequences obtained from potyvirus and cardiovirus 2A peptides, FMDV (foot-and-mouth disease virus), equine rhinitis A virus, Thosea asigna virus and porcine teschovirus. In other embodiments, the self-cleaving polypeptide site comprises a 2A or 2A-like site, sequence or domain (Donnelly et al., 2001. *J Gen. Viral.* 82:1027-1041).

Generally, it is understood that any appropriate viral vector may be used for transduction of the engineered constructs described herein. In one embodiment described herein, a cell (e.g., T cell) is transduced with a retroviral vector, e.g., a lentiviral vector, encoding an engineered DN TGF-β Receptor construct and an engineered TCR or CAR construct as described herein. The transduced T cells elicits a stable, long-term, and persistent T cell response.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in some embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis encephalitis virus (CAEV); equine infectious anemia virus (EIAV); feline immunodeficiency virus (Hy); bovine immune deficiency virus (BIV); and simian immunodeficiency virus (SIV).

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus. The term "hybrid vector" refers to a vector, LTR or other nucleic acid containing both retroviral, e.g., lentiviral, sequences and non-retroviral viral sequences. In one embodiment, a hybrid vector refers to a vector or transfer plasmid comprising retroviral e.g., lentiviral, sequences for reverse transcription, replication, integration and/or packaging.

In some embodiments, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the disclosure and are present in DNA form in the DNA plasmids of the disclosure. In one embodiment described herein, the expression vector is a lentivirus expression vector.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R, and U5. The U3 region contains the enhancer and promoter elements. The U5 region is the sequence between the primer binding site and the R region and contains the polyadenylation sequence. The R (repeat) region is flanked by the U3 and U5 regions. The LTR is composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site).

As used herein, the term "packaging signal" or "packaging sequence" refers to sequences located within the retroviral genome which are required for insertion of the viral RNA into the viral capsid or particle, see e.g., Clever et al., 1995. *J of Virology*, Vol. 69, No. 4; pp. 2101-2109. Several retroviral vectors use the minimal packaging signal (also referred to as the psi ['P'] sequence) needed for encapsidation of the viral genome. Thus, as used herein, the terms "packaging sequence," "packaging signal," "psi" and the symbol "P," are used in reference to the non-coding sequence required for encapsidation of retroviral RNA strands during viral particle formation.

In various embodiments, vectors comprise modified 5' LTR and/or 3' LTRs. Either or both of the LTR may comprise one or more modifications including, but not limited to, one or more deletions, insertions, or substitutions. Modifications of the 3' LTR are often made to improve the safety of lentiviral or retroviral systems by rendering viruses replication-defective. As used herein, the term "replication-defective" refers to virus that is not capable of complete, effective replication such that infective virions are not produced (e.g., replication-defective lentiviral progeny). The term "replication-competent" refers to wild-type virus or mutant virus that is capable of replication, such that viral replication of the virus is capable of producing infective virions (e.g., replication-competent lentiviral progeny).

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. This is because the right (3 ') LTR U3 region is used as a template for the left (5') LTR U3 region during viral replication and, thus, the viral transcript cannot be made without the U3 enhancer-promoter. In a further embodiment of the disclosure, the 3'LTR is modified such that the U5 region is replaced, for example, with an ideal poly(A) sequence. It should be noted that modifications to the LTRs such as modifications to the 3'LTR, the 5'LTR, or both 3' and 5'LTRs, are also contemplated herein.

An additional safety enhancement is provided by replacing the U3 region of the 5'LTR with a heterologous promoter to drive transcription of the viral genome during production of viral particles. Examples of heterologous promoters which may be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In certain embodiments, the heterologous promoter has additional advantages in controlling the manner in which the viral genome is transcribed. For example, the heterologous promoter may be inducible, such that transcription of all or part of the viral genome will occur only when the induction factors are present. Induction factors include, but are not limited to, one or more chemical compounds or the physiological conditions such as temperature or pH, in which the host cells are cultured.

In some embodiments, viral vectors comprise a TAR element. The term "TAR" refers to the "trans-activation response" genetic element located in the R region of lentiviral (e.g., HIV) LTRs. This element interacts with the lentiviral trans-activator (tat) genetic element to enhance viral replication.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a includes the central polypurine tract and central termination sequences (cPPT and CTS) of a retrovirus, e.g., HIV-I or HIV-2. Suitable FLAP elements are described in U.S. Pat. No. 6,682,907 and in Zennou, et al., 2000, *Cell*, 101: 173. During HIV-I reverse transcription, central initiation of the plus-strand DNA at the central polypurine tract (cPPT) and central termination at the central termination sequence (CTS) lead to the formation of a three-stranded DNA structure: the HIV-I central DNA flap. While not wishing to be bound by any theory, the DNA flap may act as a cis-active determinant of lentiviral genome nuclear import and/or may increase the titer of the virus.

In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J Virol.* 65: 1053; and Cullen et al., 1991. *Cell* 58: 423), and the hepatitis B virus post-transcriptional regulatory element (HPRE). Generally, the RNA export element is placed within the 3' UTR of a gene, and may be inserted as one or multiple copies.

In other embodiments, expression of heterologous sequences in viral vectors is increased by incorporating post-transcriptional regulatory elements, efficient polyadenylation sites, and optionally, transcription termination signals into the vectors. A variety of posttranscriptional regulatory elements may increase expression of a heterologous nucleic acid at the protein, e.g., woodchuck hepatitis virus post-transcriptional regulatory element (WPRE; Zufferey et al., 1999, *J Virol.*, 73:2886); the post-transcriptional regulatory element present in hepatitis B virus (HPRE) (Huang et al., *Mol. Cell. Biol.*, 5:3864); and the like (Liu et al., 1995, *Genes Dev.*, 9:1766).

In some embodiments, vectors may include regulatory oligonucleotides having transcriptional or translational regulatory activity. Such an oligonucleotide can be used in a variety of gene expression configurations for regulating control of expression. A transcriptional regulatory oligonucleotide, can increase (enhance) or decrease (silence) the level of expression of a recombinant expression construct. Regulatory oligonucleotides may selectively regulate expression in a context specific manner, including, for example, for conferring tissue specific, developmental stage specific, or the like expression of the polynucleotide, including constitutive or inducible expression. A regulatory oligonucleotide of the disclosure also can be a component of an expression vector or of a recombinant nucleic acid molecule comprising the regulatory oligonucleotide operatively linked to an expressible polynucleotide. A regulatory element can be of various lengths from a few nucleotides to several hundred nucleotides.

Elements directing the efficient termination and polyadenylation of the heterologous nucleic acid transcripts increases heterologous gene expression. Transcription termination signals are generally found downstream of the polyadenylation signal. In some embodiments, vectors comprise a polyadenylation sequence 3' of a polynucleotide encoding a polypeptide to be expressed. The term "poly A site" or "poly A sequence" as used herein denotes a DNA sequence which directs both the termination and polyadenylation of the nascent RNA transcript by RNA polymerase II. Polyadenylation sequences may promote mRNA stability by addition of a poly A tail to the 3' end of the coding sequence and thus, contribute to increased translational efficiency. Efficient polyadenylation of the recombinant transcript is desirable as transcripts lacking a poly A tail are unstable and are rapidly degraded. Illustrative examples of poly A signals that may be used in a vector of the disclosure, includes an ideal poly A sequence (e.g., AATAAA, ATTAAA, AGTAAA), a bovine growth hormone poly A sequence (BGHpA), a rabbit β-globin poly A sequence (rβgpA), or another suitable heterologous or endogenous poly A sequence known in the art.

In one embodiment described herein, the vectors described herein comprise a promoter operably linked to a polynucleotide encoding an engineered DN TGF-β Receptor and encoding a TCR or CAR polypeptide. In one embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 11 encoding the polypeptide expressing the extracellular domain having at least 75% sequence identity to (such as, at least 75%, at least 80%, at least 90%, at least 95%, or 100% identity; e e.g., 85-90%, 85-95%, 85-100%, 90-95%, 90-100%, or 95-100%) SEQ ID NO: 3 and the transmembrane domain having at least 75% sequence identity to (such as, at least 75%, at least 80%, at least 90%, at least 95%, or 100% identity; e e.g., 85-90%, 85-95%, 85-100%, 90-95%, 90-100%, or 95-100%) SEQ ID NO: 4.

```
                                         (SEQ ID NO: 11)
TTACAGTGCTTCTGCCATTTATGCACCAAGGACAACTTCACTTGTGTCAC

CGATGGTTTATGCTTCGTGAGCGTGACCGAGACCACCGACAAGGTGATCC

ACAACAGCATGTGCATCGCCGAGATCGATTTAATCCCTCGTGACAGACCC
```

```
                    -continued
TTCGTGTGCGCCCCTAGCAGCAAGACCGGCAGCGTGACCACCACCTACTG

CTGCAACCAAGATCACTGCAACAAGATCGAGCTGCCCACCACCGTGAAGA

GCAGCCCCGGTTTAGGACCCGTTGAACTGGCTGCCGTGATTGCCGGCCCC

GTGTGCTTTGTGTGCATCTCTTTAATGCTGATGGTGTACATT
```

In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 11 operably linked to a nucleic acid sequence encoding an engineered TCR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 11 operably linked to a nucleic acid sequence encoding an engineered CAR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 11 under control of the same promoter as the nucleic acid sequence encoding an engineered TCR or an engineered CAR.

In another embodiment described herein, the expression vector comprises the nucleic acid sequence as shown having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 48 encoding the polypeptide expressing the extracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 15, and the transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 16.

```
                                         (SEQ ID NO: 48)
ATGGGCAGGGGCCTGCTGAGGGGCCTGTGGCCCCTGCACATCGIGCTGTG

GACCAGGATCGCCAGCACCATCCCCCCCCACGTGCAGAAGAGCGTGAACA

ACGACATGATCGTGACCGACAACAACGGCGCCGTGAAGTTCCCCCAGCTG

TGCAAGTTGGCGACGTGAGGTTCAGCACCTGCGACAACCAGAAGAGCTGC

ATGAGCAACTGCAGCATCACCAGCATCTGCGAGAAGCCCCAGGAGGTGTG

CGTGGCCGTGTGGAGGAAGAACGACGAGAACATCACCCTGGAGACCGTGT

GCCACGACCCCAAGCTGCCCTACCACGACTTCATCCTGGAGGACGCCGCC

AGCCCCAAGTGCATCATGAAGGAGAAGAAGAAGCCCGGCGAGACCTTCTT

CATGTGCAGCTGCAGCAGCGACGAGTGCAACGACAACATCATCTTCAGCG

AGGAGTACAACACCAGCAACCCCGACCTGCTGCTGGTGATCTICCAGGIG
```

-continued
ACCGGCATCAGCCTGCTGCCCCCCTGGGCGTGGCCATCAGCGTGATCAT

CATCTTCTACTGCTACAGGGTGAACAGGCAG.

In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 48 operably linked to a nucleic acid sequence encoding an engineered TCR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 48 operably linked to a nucleic acid sequence encoding an engineered CAR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 48 under control of the same promoter as the nucleic acid sequence encoding an engineered TCR or an engineered CAR.

In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 35 encoding polypeptide expressing the extracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 15, and the transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 18.

(SEQ ID NO: 35)
ATGCTGCTGCTGGTGACCAGCCTGCTGCTGTGCGAGCTGCCCCACCCCGC

CTTCCTGCTGATCCCCGAGCAGAAGCTGATCAGCGAGGAGGACCTGACCA

TCCCCCCCCACGTGCAGAAGAGCGTGAACAACGACATGATCGTGACCGAC

AACAACGGCGCCGTGAAGTTCCCCCAGCTGTGCAAGTTCTGCGACGTGAG

GTTCAGCACCTGCGACAACCAGAAGAGCTGCATGAGCAACTGCAGCATCA

CCAGCATCTGCGAGAAGCCCCAGGAGGTGTGCGTGGCCGTGTGGAGGAAG

AACGACGAGAACATCACCCTGGAGACCGTGTGCCACGACCCCAAGCTGCC

CTACCACGACTTCATCCTGGAGGACGCCGCCAGCCCCAAGTGCATCATGA

AGGAGAAGAAGAAGCCCGGCGAGACCTTCTTCATGTGCAGCTGCAGCAGC

GACGAGTGCAACGACAACATCATCTTCAGCGAGGAGTACAACACCAGCAA

CCCCGACCCCAGCCCCATCCTGCTGACCATCAGCATCCTGAGCTTCTTCA

GCGTGGCCCTGCTGGTGATCCTG.

In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 35 operably linked to a nucleic acid sequence encoding an engineered TCR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 35 operably linked to a nucleic acid sequence encoding an engineered CAR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 35 under control of the same promoter as the nucleic acid sequence encoding an engineered TCR or an engineered CAR.

In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 36 encoding polypeptide expressing the extracellular domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 15 and the transmembrane domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 20.

(SEQ ID NO: 36)
ATGCTGCTGCTGGTGACCAGCCTGCTGCTGTGCGAGCTGCCCCACCCCGC

CTTCCTGCTGATCCCCGAGCAGAAGCTGATCAGCGAGGAGGACCTGACCA

TCCCCCCCCACGTGCAGAAGAGCGTGAACAACGACATGATCGTGACCGAC

AACAACGGCGCCGTGAAGTTCCCCCAGCTGTGCAAGTTCTGCGACGTGAG

GTTCAGCACCTGCGACAACCAGAAGAGCTGCATGAGCAACTGCAGCATCA

CCAGCATCTGCGAGAAGCCCCAGGAGGTGTGCGTGGCCGTGTGGAGGAAG

AACGACGAGAACATCACCCTGGAGACCGTGTGCCACGACCCCAAGCTGCC

CTACCACGACTTCATCCTGGAGGACGCCGCCAGCCCCAAGTGCATCATGA

AGGAGAAGAAGAAGCCCGGCGAGACCTTCTTCATGTGCAGCTGCAGCAGC

GACGAGTGCAACGACAACATCATCTTCAGCGAGGAGTACAACACCAGCAA

CCCCGACCCCAGCGGCATCCTGCTGACCTGCCCCACCATCAGCATCCTGA

GCTTCTTCAGCGTGGCCCTGCTGGTGATCCTG.

In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 49 encoding polypeptide expressing a CAR construct targeting GPC3 (A "GPC3-CAR"):

(SEQ ID NO: 49)
GAGCAGAAGCTGATCAGCGAGGAGGACCTCGATATCGTGATGACCCAGAG

CCCCGACTCTTTAGCTGTGTCTTTAGGAGAGAGGGCCACAATCAACTGCA

-continued
AGAGCAGCCAGAGCCTCCTCTACAGCAGCAACCAGAAGAACTATTTAGCT

TGGTACCAGCAAAAGCCCGGCCAGCCCCCCAAGCTGCTGATCTACTGGGC

CAGCAGCAGAGAGAGCGGCGTGCCCGATAGATTCAGCGGAAGCGGCTCCG

GCACAGATTTCACCCTCACCATTAGCTCTTTACAAGCTGAGGACGTGGCC

GTGTACTACTGCCAGCAGTACTACAACTACCCTTTAACCTTCGGCCAAGG

TACCAAGCTGGAGATCAAGGGCTCCACATCCGGATCCGGCAAGCCCGGTA

GCGGAGAAGGCAGCACAAAGGGAGAGGTGCAGCTGGTGGAGAGCGGAGGC

GGACTGGTCCAGCCCGGTGGATCTTTAAGGCTGTCTTGTGCCGCCAGCGG

CTTTACCTTTAACAAGAACGCTATGAACTGGGTGAGGCAAGCTCCCGGTA

AGGGTTTAGAGTGGGTGGGTCGTATTCGTAATAAGACCAACAACTACGCC

ACCTACTATGCCGACTCCGTGAAGGCTCGTTTCACCATCTCTCGTGACGA

CAGCAAGAACAGCCTCTATTTACAGATGAACTCTTTAAAGACCGAGGACA

CCGCCGTGTACTATTGCGTGGCTGGCAACTCCTTCGCCTACTGGGGCCAA

GGCACTTTAGTGACCGTGAGCTCCgggtccACCACGACGCCAGCGCCGCG

ACCACCAACACCGGCGCCCACCATCGCGTCGCAGCCCCTGTCCCTGCGCC

CAGAGGCGTGCCGGCCAgcggcgggggcgcagTGCACACGAGGGGGCTG

GACTTCGCCTGTGATATCTACATCTGGGCGCCCTTGGCCGGGACTTGTGG

GGTCCTTCTCCTGTCACTGGTTATCACCCTTTACTGCAAACGGGGCAGAA

AGAAACTCCTGTATATATTCAAACAACCATTTATGAGACCAGTACAAACT

ACTCAAGAGGAAGATGGCTGTAGCTGCCGATTTCCAGAAGAAGAAGAAGG

AGGATGTGAACTGAGAGTGAAGTTCAGCAGGAGCGCAGACGCCCCCGCGT

ACCAGCAGGGCCAGAACCAGCTCTATAACGAGCTCAATCTAGGACGAAGA

GAGGAGTACGATGTTTTGGACAAGAGgCGTGGCCGGGACCCTGAGATGGG

GGGAAAGCCGAGAAGGAAGAACCCTCAGGAAGGCCTGTACAATGAACTGC

AGAAAGATAAGATGGCGGAGGCCTACAGTGAGATTGGGATGAAAGGCGAG

CGCCGGAGGGGCAAGGGGCACGATGGCCTTTACCAGGGTCTCAGTACAGC

CACCAAGGACACCTACGACGCCCTTCACATGCAGGCCCTGCCCCCTCGC.

In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 49 operably linked to a nucleic acid sequence encoding a DN TGF-β Receptor. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 49 operably linked to a nucleic acid sequence encoding an engineered CAR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 49 under control of the same promoter as the nucleic acid sequence encoding an engineered DN TGF-β Receptor. In one embodiment described herein, the expression vector comprises the nucleic acid sequence of a CAR-DN TGF-β Receptor construct having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 50:

(SEQ ID NO: 50)
GAGCAGAAGCTGATCAGCGAGGAGGACCTCGATATCGTGATGACCCAGAG

CCCCGACTCTTTAGCTGTGTCTTTAGGAGAGAGGGCCACAATCAACTGCA

AGAGCAGCCAGAGCCTCCTCTACAGCAGCAACCAGAAGAACTATTTAGCT

TGGTACCAGCAAAAGCCCGGCCAGCCCCCCAAGCTGCTGATCTACTGGGC

CAGCAGCAGAGAGAGCGGCGTGCCCGATAGATTCAGCGGAAGCGGCTCCG

GCACAGATTTCACCCTCACCATTAGCTCTTTACAAGCTGAGGACGTGGCC

GTGTACTACTGCCAGCAGTACTACAACTACCCTTTAACCTTCGGCCAAGG

TACCAAGCTGGAGATCAAGGGCTCCACATCCGGATCCGGCAAGCCCGGTA

GCGGAGAAGGCAGCACAAAGGGAGAGGTGCAGCTGGTGGAGAGCGGAGGC

GGACTGGTCCAGCCCGGTGGATCTTTAAGGCTGTCTTGTGCCGCCAGCGG

CTTTACCTTTAACAAGAACGCTATGAACTGGGTGAGGCAAGCTCCCGGTA

AGGGTTTAGAGTGGGTGGGTCGTATTCGTAATAAGACCAACAACTACGCC

ACCTACTATGCCGACTCCGTGAAGGCTCGTTTCACCATCTCTCGTGACGA

CAGCAAGAACAGCCTCTATTTACAGATGAACTCTTTAAAGACCGAGGACA

CCGCCGTGTACTATTGCGTGGCTGGCAACTCCTTCGCCTACTGGGGCCAA

GGCACTTTAGTGACCGTGAGCTCCgggtccACCACGACGCCAGCGCCGCG

ACCACCAACACCGGCGCCCACCATCGCGTCGCAGCCCCTGTCCCTGCGCC

CAGAGGCGTGCCGGCCAgcggcgggggcgcagTGCACACGAGGGGGCTG

GACTTCGCCTGTGATATCTACATCTGGGCGCCCTTGGCCGGGACTTGTGG

GGTCCTTCTCCTGTCACTGGTTATCACCCTTTACTGCAAACGGGGCAGAA

AGAAACTCCTGTATATATTCAAACAACCATTTATGAGACCAGTACAAACT

ACTCAAGAGGAAGATGGCTGTAGCTGCCGATTTCCAGAAGAAGAAGAAGG

AGGATGTGAACTGAGAGTGAAGTTCAGCAGGAGCGCAGACGCCCCCGCGT

ACCAGCAGGGCCAGAACCAGCTCTATAACGAGCTCAATCTAGGACGAAGA

GAGGAGTACGATGTTTTGGACAAGAGgCGTGGCCGGGACCCTGAGATGGG

GGGAAAGCCGAGAAGGAAGAACCCTCAGGAAGGCCTGTACAATGAACTGC

AGAAAGATAAGATGGCGGAGGCCTACAGTGAGATTGGGATGAAAGGCGAG

CGCCGGAGGGGCAAGGGGCACGATGGCCTTTACCAGGGTCTCAGTACAGC

CACCAAGGACACCTACGACGCCCTTCACATGCAGGCCCTGCCCCCTCGCG

GCTCTggagagggcagaggctctctgctgacctgcggcgacgtggaagag aacccaggccccATGGGAAGAGGTTTACTGAGAGGACTGTGGCCTTTACA

CATCGTGCTGTGGACTCGTATCGCCAGCACCATCCCCCCCCATGTGCAGA

AGAGCGTGAACAACGACATGATCGTGACCGACAACAATGGCGCCGTGAAG

TTCCCCCAGCTGTGCAAGTTCTGCGACGTGAGGTTCAGCACTTGTGACAA

CCAGAAGAGCTGCATGAGCAACTGCAGCATCACCTCCATCTGCGAGAAGC

CCCAAGAAGTGTGCGTGGCCGTGTGGAGGAAGAACGACGAGAACATCACT

TTAGAGACAGTGTGCCACGACCCCAAGCTGCCCTACCACGACTTCATTTT

```
AGAAGATGCCGCCAGCCCCAAGTGCATCATGAAGGAGAAGAAGAAGCCCG

GCGAGACCTTCTTCATGTGCAGCTGCAGCTCCGACGAGTGCAACGATAAC

ATCATCTTCAGCGAGGAGTACAACACCAGCAACCCCGATTTACTGCTGGT

GATCTTCCAAGTTACCGGCATTTCTTTACTGCCTCCTTTAGGCGTGGCTA

TCAGCGTGATCATCATCTTCTACTGCTATAGGGTGAACAGACAG.
```

Also described herein are "codon-optimized" nucleic acids. A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells) by replacing at least one, more than one, or a significant number, of codons of the native sequence with codons that are more frequently or most frequently used in the genes of that species. Codon optimization does not alter the amino acid sequence of the encoded protein.

The codon-optimized nucleotide sequences presented in the instant disclosure can present improved properties related to expression efficacy. In some embodiments, the DNA sequence to be transcribed may be optimized to facilitate more efficient transcription and/or translation. In some embodiments, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, mRNA secondary structure, stable free energy of mRNA, repetitive sequences, RNA instability motif, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding.

In another embodiment described herein, the expression vector comprises the codon-optimized nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 51 encoding polypeptide expressing a GPC3-CAR construct ("CAR 1"):

```
                                          (SEQ ID NO: 51)
GATATCGTGATGACCCAGAGCCCCGACTCTTTAGCTGTGAGCCTTGGAGA

GAGGGCCACAATCAACTGCAAGAGCAGCCAGAGCCTCCTCTACAGCAGCA

ACCAGAAGAACTATTTAGCTTGGTACCAGCAAAAGCCCGGCCAGCCCCCC

AAGCTGCTGATCTACTGGGCCAGCAGCAGAGAGAGCGGCGTGCCCGATAG

ATTCAGCGGAAGCGGCTCCGGCACAGATTTCACCCTCACCATTAGCTCTT

TACAAGCTGAGGACGTGGCCGTGTACTACTGCCAGCAGTACTACAACTAC

CCTTTAACCTTCGGCCAAGGAACAAAGCTGGAGATCAAGGGCTCCACATC

CGGATCCGGCAAGCCCGGTAGCGGAGAAGGCAGCACAAAGGGAGAGGTGC

AGCTGGTGGAGAGCGGAGGCGGACTGGTCCAGCCCGGTGGATCTTTAAGG

CTGTCTTGTGCCGCCAGCGGCTTTACCTTTAACAAGAACGCTATGAACTG

GGTCCGACAAGCTCCCGGAAAAGGTTTAGAGTGGGTGGGTCGTATTCGTA

ATAAGACCAACAACTACGCCACCTACTATGCCGACTCCGTGAAGGCTCGT

TTCACCATCTCTCGTGACGACAGCAAGAACAGCCTCTATTTACAAATGAA

CTCTTTAAAGACCGAGGACACCGCCGTGTACTATTGCGTGGCTGGCAACT

CCTTCGCCTACTGGGGCCAAGGCACTTTAGTGACCGTGAGCTCCgggtcc

ACCACGACGCCAGCGCCGCGACCACCAACACCGGCGCCCACCATCGCGTC

GCAaCCCCTGTCCCTGCGCCCcGAGGCGTGCCGGCCAgcggcggggggcg cagTGCACACGAGGGGCTGGACTTCGCCTGTGATATCTACATCTGGGCG

CCCTTGGCCGGGACTTGTGGGGTCCTTCTCCTGTCACTGGTTATCACCCT

TTAtTGCAAACGGGGCAGAAAGAAACTCCTGTATATATTCAAACAACCAT

TTATGAGACCAGTACAAACTACTCAAGAGGAAGATGGCTGTAGCTGCCGA

TTTCCAGAAGAAGAAGAAGGAGGATGTGAAttgAGAGTGAAGTTCAGCAG

GAGCGCAGACGCCCCCGCcTAtCAGCAaGGCCAGAACCAGCTCTATAACG

AGCTCAATtTAGGgCGAAGAGAGGAGTACGATGTTTTGGACAAGAGgCGT

GGCCGGACCCcGAaATGGGGGGAAAGCCGAGAAGGAAGAACCCTCAGGA

AGGCtTGTACAATGAAtTGCAGAAgGATAAGATGGCGGAGGCaTACAGTG

AGATTGGGATGAAAGGCGAGCGCCGGAGGGGCAAGGGGCACGATGGCCTT

TAtCAGGGTCTCAGTACAGCCACCAAGGACACCTACGACGCCCTTCACAT

GCAaGCCCTGCCCCCTCGC.
```

In another embodiment described herein, the expression vector comprises the codon-optimized nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 51 operably linked to a nucleic acid sequence encoding a DN TGF-β Receptor as described herein. In another embodiment described herein, the expression vector comprises codon-optimized nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 51 operably linked to a nucleic acid sequence encoding an engineered CAR. In another embodiment described herein, the expression vector comprises the codon-optimized nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 51 under control of the same promoter as the nucleic acid sequence encoding an engineered DN TGF-β Receptor. In one embodiment described herein, the expression vector comprises the codon-optimized nucleic acid sequence of a CAR-DN TGF-β Receptor construct having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 52 ("CAR DNR A"):

(SEQ ID NO: 52)
GATATCGTGATGACCCAGAGCCCCGACTCTTTAGCTGTGAGCCTTGGAGA

GAGGGCCACAATCAACTGCAAGAGCAGCCAGAGCCTCCTCTACAGCAGCA

ACCAGAAGAACTATTTAGCTTGGTACCAGCAAAAGCCCGGCCAGCCCCCC

AAGCTGCTGATCTACTGGGCCAGCAGCAGAGAGAGCGGCGTGCCCGATAG

ATTCAGCGGAAGCGGCTCCGGCACAGATTTCACCCTCACCATTAGCTCTT

TACAAGCTGAGGACGTGGCCGTGTACTACTGCCAGCAGTACTACAACTAC

CCTTTAACCTTCGGCCAAGGAACAAAGCTGGAGATCAAGGGCTCCACATC

CGGATCCGGCAAGCCCGGTAGCGGAGAAGGCAGCACAAAGGGAGAGGTGC

AGCTGGTGGAGAGCGGAGGCGGACTGGTCCAGCCCGGTGGATCTTTAAGG

CTGTCTTGTGCCGCCAGCGGCTTTACCTTTAACAAGAACGCTATGAACTG

GGTCCGACAAGCTCCCGGAAAAGGTTTAGAGTGGGTGGGTCGTATTCGTA

ATAAGACCAACAACTACGCCACCTACTATGCCGACTCCGTGAAGGCTCGT

TTCACCATCTCTCGTGACGACAGCAAGAACAGCCTCTATTTACAAATGAA

CTCTTTAAAGACCGAGGACACCGCCGTGTACTATTGCGTGGCTGGCAACT

CCTTCGCCTACTGGGGCCAAGGCACTTTAGTGACCGTGAGCTCCgggtcc

ACCACGACGCCAGCGCCGCGACCACCAACACCGGCGCCCACCATCGCGTC

GCAaCCCCTGTCCCTGCGCCCcGAGGCGTGCCGGCCAgcggcgggggcg cagTGCACACGAGGGGGCTGGACTTCGCCTGTGATATCTACATCTGGGCG

CCCTTGGCCGGGACTTGTGGGGTCCTTCTCCTGTCACTGGTTATCACCCT

TTAttGCAAACGGGGCAGAAAGAAACTCCTGTATATATTCAAACAACCAT

TTATGAGACCAGTACAAACTACTCAAGAGGAAGATGGCTGTAGCTGCCGA

TTTCCAGAAGAAGAAGAAGGAGGATGTGAAttgAGAGTGAAGTTCAGCAG

GAGCGCAGACGCCCCCGCcTAtCAGCAaGGCCAGAACCAGCTCTATAACG

AGCTCAATtTAGGgCGAAGAGAGGAGTACGATGTTTTGGACAAGAGgCGT

GGCCGGGACCCcGAaATGGGGGGAAAGCCGAGAAGGAAGAACCCTCAGGA

AGGCtTGTACAATGAAtTGCAGAAgGATAAGATGGCGGAGGCaTACAGTG

AGATTGGGATGAAAGGCGAGCGCCGGAGGGGCAAGGGGCACGATGGCCTT

TAtCAGGGTCTCAGTACAGCCACCAAGGACACCTACGACGCCCTTCACAT

GCAaGCCCTGCCCCCTCGCgGCTCTggagagggcagaggctctctgctga cctgcggcgacgtggaagagaacccaggccccATGGGAAGAGGTTTACTG

AGAGGACTGTGGCCTTTACACATCGTGCTGTGGACTCGTATCGCCAGCAC

CATCCCCCCCCATGTcCAaAAGAGCGTGAACAACGACATGATCGTGACCG

ACAACAATGGCGCCGTGAAGTTCCCCCAGCTGTGCAAGTTCTGCGACGTG

AGGTTCAGCACTTGTGACAACCAGAAGAGCTGCATGAGCAACTGCAGCAT

CACCTCCATCTGCGAGAAGCCCCAAGAAGTGTGCGTGGCCGTGTGGAGGA

AGAACGACGAGAACATCACTTTAGAGACAGTGTGCCACGACCCCAAGCTG

CCCTACCACGACTTCATTTTAGAAGATGCCGCCAGCCCCAAGTGCATCAT

GAAGGAGAAGAAGAAGCCCGGCGAGACCTTCTTCATGTGTTCTTGTTCGT

CTGATGAGTGCAACGATAACATCATCTTCAGCGAGGAGTACAACACCAGC

AACCCCGATTTACTGCTGGTGATCTTCCAAGTTACCGGCATTTCTTTACT

-continued
GCCTCCgTTgGGCGTGGCTATCAGCGTGATCATCATCTTCTACTGCTATC

GTGTTAATCGTCAA.

The vectors may have one or more LTRs, wherein any LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi (Ψ) packaging signal, RRE), and/or other elements that increase therapeutic gene expression (e.g., poly (A) sequences), and may optionally comprise a WPRE or HPRE. The skilled artisan would appreciate that many other different embodiments may be fashioned from the existing embodiments of the disclosure.

A "host cell" includes cells transfected, infected, or transduced in vivo, ex vivo, or in vitro with a recombinant vector or a polynucleotide of the disclosure. Host cells may include packaging cells, producer cells, and cells infected with viral vectors. In some embodiments, host cells infected with viral vector of the disclosure are administered to a subject in need of therapy. In certain embodiments, the term "target cell" is used interchangeably with host cell and refers to transfected, infected, or transduced cells of a desired cell type. In some embodiments, the target cell is a T cell.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A retroviral/lentiviral transfer vector of the present disclosure may be introduced into a packaging cell line, via transfection, transduction or infection, to generate a producer cell or cell line. The packaging vectors of the present disclosure may be introduced into human cells or cell lines by common methods including, e.g., calcium phosphate transfection, lipofection or electroporation. In some embodiments, the packaging vectors are introduced into the cells together with a dominant selectable marker, such as neomycin, hygromycin, puromycin, blastocidin, zeocin, thymidine kinase, DHFR, Gln synthetase or ADA, followed by selection in the presence of the appropriate drug and isolation of clones. A selectable marker gene may be linked physically to genes encoding by the packaging vector, e.g., by IRES or self-cleaving viral peptides.

Viral envelope proteins (env) determine the range of host cells which may ultimately be infected and transformed by recombinant retroviruses generated from the cell lines. In the case of lentiviruses, such as HIV-1, HIV-2, SIV, FIV and EIV, the env proteins include gp41 and gp120. In some embodiments, the viral env proteins expressed by packaging cells of the disclosure are encoded on a separate vector from the viral gag and pol genes, as has been previously described.

Illustrative examples of retroviral-derived env genes which may be employed in the embodiments described herein include, but are not limited to: MLV envelopes, 10A1 envelope, BAEV, FeLV-B, RDI 14, SSAV, Ebola, Sendai, FPV (Fowl plague virus), and influenza virus envelopes. Similarly, genes encoding envelopes from RNA viruses (e.g., RNA virus families of Picomaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Bimaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BL V, EBV, CAEV, SNV, ChTL V, STLV, MPMV SMRV, RAV, FuSV, MH2, AEV, AMV, CTIO, and EIAV.

In other embodiments, envelope proteins for pseudotyping a virus of present disclosure include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpes viruses such as Herpes simplex virus types 1 and 2, varicella zoster, cytomegalovirus, Epstein-Barr virus (EBV), human herpesviruses (HHV), human herpesvirus type 6 and 8, Human immunodeficiency virus (HIV), papilloma virus, murine gamma herpes virus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-Co V), West Nile virus, or any encephaliltis causing virus.

The terms “pseudotype” or “pseudotyping” as used herein, refer to a virus whose viral envelope proteins have been substituted with those of another virus possessing other characteristics. For example, HIV may be pseudotyped with vesicular stomatitis virus G-protein (VSV-G) envelope proteins, which allows HIV to infect a wider range of cells because HIV envelope proteins (encoded by the env gene) normally target the virus to $CD4^+$ presenting cells.

As used herein, the term “packaging cell lines” is used in reference to cell lines that do not contain a packaging signal, but do stably or transiently express viral structural proteins and replication enzymes (e.g., gag, pol and env) which are necessary for the correct packaging of viral particles. Any suitable cell line may be employed to prepare packaging cells of the disclosure. Generally, the cells are mammalian cells. In another embodiment, the cells used to produce the packaging cell line are human cells. Suitable cell lines which may be used to produce the packaging cell line include, for example, CHO cells, BHK cells, MDCK cells, C3H 10T1/2 cells, FLY cells, Psi-2 cells, BOSC 23 cells, P A317 cells, WEHI cells, COS cells, BSC 1 cells, BSC 40 cells, BMT 10 cells, VERO cells, W138 cells, MRCS cells, A549 cells, HTI080 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells.

As used herein, the term “producer cell line” refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J Virol.* 66:5110-5113. Infectious virus particles may be collected from the packaging cells using conventional techniques. For example, the infectious particles may be collected by cell lysis, or collection of the supernatant of the cell culture, as is known in the art. Optionally, the collected virus particles may be purified if desired. Suitable purification techniques are well known to those skilled in the art.

The delivery of a gene(s) or other polynucleotide sequence using a retroviral or lentiviral vector by means of viral infection rather than by transfection is referred to as “transduction.” In one embodiment, retroviral vectors are transduced into a cell through infection and provirus integration. In certain embodiments, a target cell, e.g., a T cell, is “transduced” if it comprises a gene or other polynucleotide sequence delivered to the cell by infection using a viral or retroviral vector. In some embodiments, a transduced cell comprises one or more genes or other polynucleotide sequences delivered by a retroviral or lentiviral vector in its cellular genome. In one embodiment described herein, a T cell is transduced with an expression vector comprising the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 11.

In some embodiments, host cells co-expressing a DN TGF-β Receptor construct of the disclosure with an engineered TCR and/or a CAR are provided. The host cells may be transduced with one or more viral vectors comprising nucleic acid sequences encoding one or more polypeptides expressing a DN TGF-β receptor construct of the disclosure and an engineered TCR and/or a CAR. The host cells may be administered to a subject to treat and/or prevent T cell malignancies. Other methods relating to the use of viral vectors in gene therapy, which may be utilized according to certain embodiments of the present disclosure, may be found in, e.g., Kay, M. A. (1997) *Chest* 111(6 Supp.): 138S-142S; Ferry, N. and Heard, J. M. (1998) *Hum. Gene Ther.* 9:1975-81; Shiratory, Y. et al., (1999) *Liver* 19:265-74; Oka, K. et al., (2000) *Curr. Opin. Lipidol.* 11:179-86; Thule, P. M. and Liu, J. M. (2000) *Gene Ther.* 7:1744-52; Yang, N. S. (1992) *Crit. Rev. Biotechnol.* 12:335-56; Alt, M. (1995) *J Hepatol.* 23:746-58; Brody, S. L. and Crystal, R. G. (1994) *Ann. NY Acad. Sci.* 716:90-101; Strayer, D. S. (1999) *Expert Opin. Investig. Drugs* 8:2159-2172; Smith-Arica, J. R. and Bartlett, J. S. (2001) *Curr. Cardiol. Rep.* 3:43-49; and Lee, H. C. et al., (2000) *Nature* 408:483-8.

The compositions described herein may comprise one or more polynucleotides, polypeptides, vectors comprising same, and T cell compositions, as contemplated herein. One embodiment described herein is a composition comprising a modified T cell that co-expresses one or more engineered DN TGF-β Receptors described herein with an engineered TCR and/or CAR. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the present disclosure may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In one embodiment described herein, compositions of the present disclosure comprise an amount of modified T cells contemplated herein. It may generally be stated that a pharmaceutical composition comprising the T cells contemplated herein may be administered at a dosage of $10^2$ to $10^{10}$ cells/kg body weight, $10^5$ to $10^9$ cells/kg body weight, $10^5$ to $10^8$ cells/kg body weight, $10^5$ to $10^7$ cells/kg body weight, $10^7$ to $10^9$ cells/kg body weight, or $10^7$ to $10^8$ cells/kg body weight, including all integer values within those ranges. The number of cells will depend upon the ultimate use for which the composition is intended as will the type of cells included therein. T cells modified to express an engineered TCR or CAR may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-7, IL-15, IL-12, TNF-alpha, IL-18, and TNF-beta, GM-CSF, IL-4, IL-13, Flt3-L, RANTES, MIP1α, etc.) as described herein to enhance engraftment and function of infused T cells.

Generally, compositions comprising the cells activated and expanded as described herein may be utilized in the treatment and prevention of diseases that arise in individuals who are immunocompromised or immunosuppressed. In some, compositions comprising the modified T cells contemplated herein are used in the treatment of cancers. The modified T cells described herein may be administered either alone, or as a pharmaceutical composition in combination with carriers, diluents, excipients, and/or with other components such as IL-2, IL-7, and/or IL-15 or other cytokines or cell populations. In some embodiments, pharmaceutical compositions contemplated herein comprise an amount of genetically modified T cells, in combination with one or more pharmaceutically or physiologically acceptable carriers, diluents or excipients.

Pharmaceutical compositions comprising modified T cells contemplated herein may further comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for parenteral administration, e.g., intravascular (intravenous or intraarterial), intraperitoneal or intramuscular administration.

The liquid pharmaceutical compositions, whether they be solutions, suspensions or other like form, may include one or more of the following: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Sterile injectable pharmaceutical composition are also included.

In some embodiments, compositions contemplated herein comprise an effective amount of an expanded modified T cell composition, alone or in combination with one or more therapeutic agents. Thus, the T cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics and anti-viral agents. Such therapeutic agents may be accepted in the art as a treatment for a disease state as described herein, such as a cancer. In one embodiment the compositions contemplated herein may also be administered with inhibitors of TGF-β, for example the small molecule inhibitor LY55299. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising T cells contemplated herein may be administered in conjunction with any number of chemotherapeutic agents. Illustrative examples of chemotherapeutic agents include but are not limited to alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE® Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RPS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions described herein. In one embodiment, the composition comprising T cells is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

In some embodiments, NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol or proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®) adalimumab (HUIMIRA®) and infliximab (REMICADE®), chemokine inhibitors and adhesion molecule inhibitors. The biological response modifiers include monoclonal antibodies as well as recombinant forms of molecules. Exemplary disease-modifying anti-rheumatic drugs (DMARDs) include azathioprine, cyclophosphamide, cyclosporine, methotrexate, penicillamine, leflunomide, sulfasalazine, hydroxychloroquine, Gold (oral (auranofin) and intramuscular) and minocycline.

In other embodiments, the therapeutic antibodies suitable for combination with the CAR modified T cells contemplated herein, include but are not limited to, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, namatumab, naptumomab, necitumumab, nimotuzumab, nofetumomab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8.

In some embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, chemokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-15, a tumor necrosis factor such as TNF-α or TNF-β; and other polypeptide factors including LIF and kit ligand (KL). As used herein, the term cytokine includes proteins from natural sources or from recombinant cell culture, and biologically active equivalents of the native sequence cytokines.

The present disclosure contemplates, in part, genetically modified T cell redirected to a target cell, e.g., a tumor or cancer cell, and that comprises the engineered DN TGF-β Receptors described herein and an engineered TCR or CAR having a binding domain that binds to target antigens on the cells, including the CAR-DN TGF-β Receptor constructs described herein. Cancer cells may also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In one embodiment, the target cell expresses an antigen, e.g., target antigen. In one embodiment, the target cell is a pancreatic parenchymal cell, pancreatic duct cell, hepatic cell, cardiac muscle cell, skeletal muscle cell, osteoblast, skeletal myoblast, neuron, vascular endothelial cell, pigment cell, smooth muscle cell, glial cell, fat cell, bone cell, chondrocyte, pancreatic islet cell, CNS cell, PNS cell, liver cell, adipose cell, hepatic cell, renal cell, lung cell, skin cell, ovary cell, follicular cell, epithelial cell, immune cell, or an endothelial cell.

In certain embodiments, the target cell is part of a pancreatic tissue, neural tissue, cardiac tissue, bone marrow, muscle tissue, bone tissue, skin tissue, liver tissue, hair follicles, vascular tissue, adipose tissue, lung tissue, and kidney tissue.

In a one embodiment, the target cell is a tumor cell. In another embodiment, the target cell is a cancer cell, such as a cell in a patient with cancer. Exemplary cells that may be killed with the disclosed methods include cells of the following tumors: a liquid tumor such as a leukemia, including acute leukemia (such as acute lymphocytic leukemia, acute myelocytic leukemia, and myeloblastic, promyelocytic, myelomonocytic, monocytic and erythroleukemia), chronic leukemias (such as chronic myelocytic (granulocytic) leukemia and chronic lymphocytic leukemia), polycythemia vera, lymphoma, Hodgkin's disease, non-Hodgkin's lymphoma, multiple myeloma, Waldenstrom's macroglobulinemia, heavy chain disease).

In another embodiment, the cell is a solid tumor cell, such as sarcomas and carcinomas, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinoma, lung cancer, colorectal cancer, squamous cell carcinoma, basal cell carcinoma, adenocarcinoma (for example adenocarcinoma of the pancreas, colon, ovary, lung, breast, stomach, prostate, cervix, or esophagus), sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors (such as a glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma).

In one embodiment, the cancer may comprise Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

In one embodiment, the target cell is a malignant cell of the liver, pancreas, lung, breast, bladder, brain, bone, thyroid, kidney, skin, and hematopoietic system. In another embodiment, the target cell is a cell in a liver cancer, pancreatic cancer, lung cancer, breast cancer, bladder cancer, brain cancer, bone cancer, thyroid cancer, kidney cancer, skin cancer, or hematological cancer. In another embodiment, the target cell is a cell, e.g., a cancer cell infected by a virus, including but not limited to CMV, HPV, and EBV.

In one embodiment, the target antigen is directed to or is an epitope of HPV oncoproteins, including HPV-16 E6 and HPV-16 E7, alpha folate receptor, 5T4, $α_vβ_6$ integrin, BCMA, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, F AP, fetal AchR, FRa, GD2, GD3, Glypican-3 (GPC3), HLA-A1+MAGEI, HLA-A2+MAGE1, HLAA3+ MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Mud, Muc16, NCAM, NKG2D Ligands, NYE-S0-1, PRAME, PSCA, PSMA, RORI, SSX, Survivin, TAG72, TEMs, and VEGFRII.

The modified T cells contemplated herein provide improved adoptive immunotherapy for use in the treatment of various conditions including, without limitation, cancer, infectious disease, autoimmune disease, inflammatory disease, and immunodeficiency. In some embodiments, the specificity of a primary T cell is redirected to tumor or cancer cells by genetically modifying the primary T cell engineered to co-express a TCR or CAR contemplated herein with an engineered DN TGF-β Receptor. For example, with the CAR-DN TGF-β Receptor constructs described herein, the antigen binding domain of the scFv of the CAR directs the T cell to the cells expressing the tumor antigen, and the TGF-β Receptor constructs described herein protect the population of such T cells by inhibiting the suppressive effect of TGF-β.

In one embodiment of the present disclosure includes a type of cellular therapy where T cells are modified to co-express an engineered DN TGF-β Receptor with an engineered TCR or CAR, including the CAR-DN TGF-β Receptor constructs described herein, that target cancer cells expressing a target antigen, and the modified T cell is infused to a recipient in need thereof. The infused cell is thus able to kill tumor cells in the recipient with minimal impact from TGF-β suppression.

Any cell may be used as a host cell for the polynucleotides, the vectors, or the polypeptides of the present disclosure. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli*; *Enterobacter*; *Envinia*; *Klebsiella*; *Proteus*; *Salmonella*, e.g., *Salmonella typhimurium*; *Serratia*, e.g., *Serratia marcescans*, and *Shigella*; Bacilli such as *B. subtilis* and *B. licheniformis*; *Pseudomonas* such as *P. aeruginosa*; and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In certain embodiments, the T cell is a tumor-infiltrating lymphocyte (TIL), autologous T cell, engineered autologous T cell (eACT™), an allogeneic T cell, a heterologous T cell, or any combination thereof. Unlike antibody therapies or stand-alone TCR or CAR modified T cells, T cells (or any cells as described above) modified to co-express the engineered DN TGF-β Receptors described herein with an engineered TCR or CAR are able to not only replicate in vivo, and thus contribute to long-term persistence that may lead to sustained cancer therapy, but have the added advantage of avoiding the suppressive impact of TGF-β. Thus, in one embodiment described herein is a method of inhibiting the activity of TGF-β comprising administering to a subject in need thereof a therapeutically effective amount of the modified T cell co-expressing the DN TGF-β Receptors described herein and a TCR or CAR as described herein.

Without being bound by any theory, it is understood that administration of the modified T cells described herein results in the DN TGF-β Receptors inhibiting the phosphorylation cascade that initiates intracellular pSMAD signaling despite binding of the TGF-β ligand to the TGF-dimer-DN TGF-βRII dimer complex, while still allowing the T cell to retain specificity of the target antigen. In another embodiment, the method of inhibiting the activity of TGF-β comprises a reduction in the levels of pSMAD2 and pSMAD3 as compared to the levels of pSMAD2 and pSMAD3 in non-transduced T cells.

In one embodiment described herein, administration of the modified T cells described herein results in reduction in levels of pSMAD2 and pSMAD3 between about 10% to about 100%, between about 20% to about 90%, between about 30% to about 80%, between about 40% to about 70%, or between about 50% to about 60%. In another embodiment described herein the reduction in pSMAD2 may be about 1%, about 5%, about 10%, about 20%, about 30%, about 40%, about 50%, about 60%, about 70%, about 80%, about 90% or about 100%. In another embodiment described herein the reduction in pSMAD3 may be about 1%, about 5%, about 10%, about 20%, about 30%, about 40%, about 50%, about 60%, about 70%, about 80%, about 90% or about 100%.

In another embodiment described herein, administration of the modified T cells described herein results in an increase in cytokine secretion in the presence of TGF-β1 of between 10% to about 100%, between about 20% to about 90%, between about 30% to about 80%, between about 40% to about 70%, or between about 50% to about 60%. In another embodiment described herein, administration of the modified T cells described herein results in an increase in cytokine secretion in the presence of TGF-β1 of about 1%, about 5%, about 10%, about 20%, about 30%, about 40%, about 50%, about 60%, about 70%, about 80%, about 90% or about 100%.

In another embodiment, T cells co-expressing the DN TGF-β Receptors with an engineered TCR or CAR as described herein may undergo T cell expansion such that a population of therapeutic T cells may remain or persist for an extended period. Thus, another embodiment described herein is a method of expanding a population of T cells comprising administering to a subject in need thereof a therapeutically effective amount of the T cells described herein.

In one embodiment described herein, the population of T cells remains between at between about 50% to about 100% after 7 days, at between about 60% to about 90% after 7 days, or at between about 70% to about 80% after 7 days. In another embodiment described herein, the population of T cells remains at about 50% after 7 days, at about 60% after 7 days, at about 70% after 7 days, at about 80% after 7 days, at about 90% after 7 days or at about 100% after 7 days.

In another embodiment described herein, administration of the modified T cells described herein results in an expansion of transduced T cells in the presence of TGF-β1 by about 10% to about 100%, about 20% to about 90%, or about 30% to about 80%. In another embodiment described herein, administration of the modified T cells described herein results in an expansion of transduced T cells in the presence of TGF-β1 by about 1%, about 5%, about 10%, about 20%, about 30%, about 40%, about 50%, 50%, about 55%, about 60%, about 65%, about 70%, about 75%, about 80%, about 85%, about 90%, about 95%, or about 100%.

In one embodiment described herein, administration of a modified T cell from a codon-optimized sequence as described herein results in an increase in expression efficiency by about 50%, about 55%, about 60%, about 65%, about 70%, about 75%, about 80%, about 85%, about 90%, about 95%, or about 100%. In another embodiment described herein, administration of a modified T cell from a codon-optimized sequence as described herein results in an increase in transduction efficiency by about 50%, about 55%, about 60%, about 65%, about 70%, about 75%, about 80%, about 85%, about 90%, about 95%, or about 100%.

Without being bound by any theory, it is believed that despite the promising use of CAR T cell therapy, constitutive tonic signaling in the absence of tumor antigen can result in reduced efficacy, poor CAR T cell survival and toxicity (Ajina et al., *Mol Cancer Ther.*, 17(9):1795-1815(2018)).

Thus, a CART cell therapy with reduced tonic signaling results superior performance. In one embodiment described herein, administration of a modified T cell from a codon-optimized sequence as described herein in the absence of tumor antigen results in a reduction of cytokine release by about 10%, about 20%, about 30%, about 40%, about 50%, 50%, about 55%, about 60%, about 65%, about 70%, about 75%, about 80%, about 85%, about 90%, about 95%, or about 100%. In one embodiment described herein, administration of a modified T cell from a codon-optimized sequence in the absence of tumor antigen results in a reduction of cytokine release by about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In another embodiment, administration of the modified T cell from a codon-optimized sequence as described herein results in a reduction in tumor volume of between about 50% to about 10% to about 100%, about 20% to about 90%, or about 30% to about 80%. In another embodiment the reduction in tumor volume is about 10%, about 20%, about 30%, about 40%, about 50%, 50%, about 55%, about 60%, about 65%, about 70%, about 75%, about 80%, about 85%, about 90%, about 95%, or about 100%.

Another embodiment described herein is a method of treating a cancer in a subject in need thereof comprising administering an effective amount, e.g., therapeutically effective amount of a composition comprising T cells co-expressing the DN TGF-β Receptors and a TCR or CAR as described herein. The quantity and frequency of administration will be determined by such factors as the condition of the patient, and the type and severity of the patient's disease, although appropriate dosages may be determined by clinical trials.

Another embodiment described herein is a method of treating a hepatic cancer in a subject in need thereof comprising administering an effective amount, e.g., therapeutically effective amount of a composition comprising T cells co-expressing the DN TGF-β Receptors and a TCR or CAR as described herein, including the CAR-DN TGF-β Receptor constructs described herein. The quantity and frequency of administration will be determined by such factors as the condition of the patient, and the type and severity of the patient's disease, although appropriate dosages may be determined by clinical trials.

In other embodiments, compositions comprising T cell genetically modified with a vector comprising a promoter operably linked to a polynucleotide encoding a DN TGF-β Receptor and a polynucleotide encoding a TCR or CAR, including the CAR-DN TGF-β Receptor constructs described herein, are used in the treatment of solid tumors or cancers including, without limitation, liver cancer, pancreatic cancer, lung cancer, breast cancer, bladder cancer, brain cancer, bone cancer, thyroid cancer, kidney cancer, skin cancer or virus induced cancers.

In some embodiments, compositions comprising T cell genetically modified with a vector comprising a promoter operably linked to a polynucleotide encoding a DN TGF-β Receptor and a polynucleotide encoding a TCR or CAR, including the CAR-DN TGF-β Receptor constructs described herein, comprises an antigen-specific binding domain that binds an epitope of BCMA, CD19, CD20, CD28, CD137 (4-1BB), CLL-1, GPC3, PCMA or PSMA are used in the treatment of various cancers.

In other embodiments, methods comprising administering a therapeutically effective amount of modified T cells contemplated herein or a composition comprising the same, to a patient in need thereof, alone or in combination with one or more therapeutic agents, are provided. In certain embodiments, the cells of the disclosure are used in the treatment of patients at risk for developing a cancer. Thus, the present disclosure provides methods for the treatment or prevention of a cancer comprising administering to a subject in need thereof, a therapeutically effective amount of the modified T cells of the disclosure.

One of ordinary skill in the art would recognize that multiple administrations of the compositions of the disclosure may be required to effect the desired therapy. For example a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom according to the present disclosure, and reinfuse the patient with these activated and expanded T cells. This process may be carried out multiple times every few weeks. In certain embodiments, T cells may be activated from blood draws of from 10 cc to 400 cc. Not to be bound by theory, using this multiple blood draw/multiple reinfusion protocol may serve to select out certain populations of T cells.

The administration of the compositions contemplated herein may be carried out in any convenient manner, including by aerosol inhalation, injection, ingestion, transfusion, implantation or transplantation. In some embodiments, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

In one embodiment, a subject in need thereof is administered an effective amount of a composition to increase a cellular immune response to a cancer in the subject. The immune response may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present disclosure, which are well described in the art; e.g., *Current Protocols in Immunology*, Edited by: John E. Coligan, Ada M. Kruisbeek, David H. Margulies, Ethan M. Shevach, Warren Strober (2001) John Wiley & Sons, NY, N.Y.

In the case of T cell-mediated killing, CAR-ligand binding initiates CAR signaling to the T cell, resulting in activation of a variety of T cell signaling pathways that induce the T cell to produce or release proteins capable of inducing target cell apoptosis by various mechanisms. These T cell-mediated mechanisms include (but are not limited to) the transfer of intracellular cytotoxic granules from the T cell into the target cell, T cell secretion of proinflammatory cytokines that may induce target cell killing directly (or indirectly via recruitment of other killer effector cells), and up regulation of death receptor ligands (e.g. FasL) on the T cell surface that induce target cell apoptosis following binding to their cognate death receptor (e.g. Fas) on the target cell.

One embodiment described herein is a method of treating a subject diagnosed with a cancer, comprising removing T cells from the subject, genetically modifying said T cells with a vector comprising a nucleic acid encoding an engineered DN TGF-β Receptor and a TCR or CAR as contemplated herein, including the CAR-DN TGF-β Receptor constructs described herein, thereby producing a population of modified T cells, and administering the population of modified T cells to the same subject.

In certain embodiments, the present disclosure also provides methods for stimulating an effector cell mediated immune modulator response to a target cell population in a subject comprising the steps of administering to the subject an immune effector cell population expressing a nucleic acid construct encoding an engineered DN TGF-β Receptor and a TCR or CAR molecule, including the CAR-DN TGF-β Receptor constructs described herein.

The methods for administering the cell compositions described herein includes any method which is effective to result in reintroduction of ex vivo genetically modified immune effector cells that either directly express an engineered TCR or CAR in the subject or on reintroduction of the genetically modified progenitors of immune effector cells that on introduction into a subject differentiate into mature immune effector cells that express the engineered TCR or CAR. One method comprises transducing peripheral blood T cells ex vivo with a nucleic acid construct in accordance with the present disclosure and returning the transduced cells into the subject.

Although the foregoing disclosure has been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those skilled in the art will readily recognize a variety of noncritical parameters that could be changed or modified to yield essentially similar results.

EXAMPLES

Example 1

An engineered, dominant-negative TGF-β receptor Type 1 (DN TGF-βRI) construct was designed and synthesized according to the sequence of SEQ ID NO: 10. This construct is 152 amino acids in length and includes a signal peptide domain from amino acid 1-33 of wild-type TGF-βRI; an extracellular domain from amino acid 34-126 of wild-type TGF-βRI; a transmembrane domain from amino acid 127-147 of wild-type TGF-βRI; and an intracellular domain from amino acid 148-152 of TGFβ-RII. The construct is designed to omit the key phosphorylation sites for intracellular pSMAD signaling. The intracellular domain is specifically derived from TGFβ-RII and comprises five amino acids.

In addition, an engineered, truncated, dominant-negative TGF-β receptor Type 2 (DN TGF-βRII) was also designed and synthesized according to the sequence of SEQ ID NO: 14.

(SEQ ID NO: 14)
MGRGLLRGLWPLHIVLWTRIASTIPPHVQKSVNNDMIVTDNNGAVKFPQL

CKFCDVRFSTCDNQKSCMSNCSITSICEKPQEVCVAVWRKNDENITLETV

CHDPKLPYHDFILEDAASPKCIMKEKKKPGETFFMCScSSDECNDNIIFS

EEYNTSNPDLLLVIFQVTGISLLPPLGVAISVIIIFYCYRVNRQ.

TCR and CAR constructs used in the following examples were designed and made using common techniques known in the art. Two different CAR constructs with two different co-stimulatory domains (CD28 and 4-1BB) are shown as follows:
  a. CD19: (FMC63 scFv+CD28 intracellular domain+ CD3ζ intracellular domain)
  b. PSMA: (a PSMA scFv+4-1BB intracellular domain+ CD3ζ intracellular domain).

A lentivirus vector was used for all T cell transductions. An EF1A promoter was used with all constructs made and tested.

CD3+ cells obtained from STEMCELL™ Technologies (Vancouver, Canada) were isolated from peripheral blood mononuclear cells obtained from healthy donors and frozen down in CryoStor® cell cryopreservation media (Sigma) Aldrich®. Before lentivirus transduction, CD3 pan T cells were thawed, activated with CD3/CD28 Dynabeads®, (ThermoFisher Scientific) according to manufacturer recommendations and rested overnight. The following day cells were transduced with lentivirus containing myc tagged CAR constructs with and without dominant-negative receptors (DNRs) as described herein. Cells were grown for 14 days in TC Media (X-VIVO™ with 5% human serum, supplemented three times per week for 100 International Units/ml of Interleukin-2 (IL-2). After the 14-day cell culture, cells in all trials were approximately 50-80% positive for the transgene as measured by flow cytometry.

All flow cytometry data was collected on LSR-Fortessa (BD LSR Fortessa™) with BD FACSDiva™ software and data was analyzed using FlowJo (all from BD Sciences). All antibody staining was performed at 4° C. in PBS containing 1% BSA. Cells were evaluated for viability, CD3+, CD4+, CD8+ and anti-myc activity using reagents from BioLegend and Cell Signaling Technology to determine % CAR positivity using common techniques. For the expansion assay, CAR cells were enumerated with counting beads from ThermoFisher Scientific.

Equal number of T cells were cultured in X-VIVO™ media without serum for two hours before 30 minute stimulation with 1 or 5 ng/mL of soluble recombinant TGF-β1 that was reconstituted in acid as recommended by the manufacturer (R&D Systems). Cells were then collected by centrifugation and lysed with RIPA buffer+protease and phosphatase inhibitors (ThermoFisher Scientific) before LUMINEX® analysis for pSMAD2 and pSMAD3.

In order to investigate whether expressing a truncated form of the TGF-βRI (DN TGF-13R1) could rescue T cells from the suppressive effects of TGF-β, a construct was designed to encode the DN TGF-βRI of SEQ ID NO: 10 with a CAR with scFvs specific to CD19 and PSMA, followed by a T2A self-cleaving peptide. The DN TGF-βRII of SEQ ID NO: 14 served as the positive control.

By eliminating the intracellular portion of the TGF-βRI molecule that transmits the suppressive pSMAD signaling, the results suggest that the truncated form of TGF-βRI (DN TGF-βRI) out-competes endogenous, wild-type TGF-βRI binding to TGF-βRII, thereby blocking signal transduction, and limiting the inhibitory pSMAD signaling induced by TGF-β1 and thus rescuing CAR cell function. TGF-β mediates suppressive signaling in T cells via pSMAD signaling pathways. To determine if truncated, dominant-negative receptor described herein could limit pSMAD induction, $CD3^+$ cells were isolated from primary human peripheral blood mononuclear cells (PBMCs) and transduced with constructs comprising CD19 CAR only (FMC63 scFv+CD28 intracellular domain+CD3ζ intracellular domain), CD19 CAR+DN TGF-βRI or CD19 CAR+DN TGF-βRII. Next, total T cells were stimulated with TGF-β1 at 1 ng/mL, for 30 minutes, prepared whole cell lysates, and pSMAD2 and pSMAD3 were quantified. The results are described in Table 4a.

TABLE 4a

CD19 CAR + Dominant-Negative TGF-βRI Receptors inhibit TGF-β1 induced pSMAD signaling

| Trial Group | pSMAD2 (MFI) | | | pSMAD3 (MFI) | | |
|---|---|---|---|---|---|---|
| No TGF-β | | | | | | |
| CD19 CAR | 33 | 25 | 32 | 18.3 | 13.3 | 15.3 |
| CD19 CAR + DN TGF-βRI | 23 | 17 | 15 | 6.8 | 6.3 | 6.3 |
| CD19 CAR + DN TGF-βRII | 12 | 21.5 | 23 | 4.3 | 5.8 | 1.3 |
| CD19 CAR + SMI (LY57299, 1 μM) | 35 | 19 | 28.5 | 7.3 | 7.3 | 8.3 |
| TGF-β1 | | | | | | |
| CD19 CAR | 10,287 | 9,188 | 9,477 | 2,570.8 | 2,477.2 | 2,533.2 |
| CD19 CAR + DN TGF-βRI | 3,176 | 2,354 | 3,654 | 1,091.3 | 929.3 | 1,272.8 |
| CD19 CAR + DN TGF-βRII | 3,021.5 | 584 | 2,552 | 1,034.3 | 940.3 | 872.3 |
| CD19 CAR + SMI (LY57299, 1 μM) | 3,076 | 3,195 | 2,634.5 | 1,265.3 | 1,191.3 | 1,084.3 |

Background levels of pSMAD2 and pSMAD3 levels in all engineered T are shown in Table 4a. TGF-β1 stimulated T cells expressing only CD19 CAR induced pSMAD2 and pSMAD3 by 10,000-fold and 2,500-fold respectively whereas TGFβ1 stimulated cells transduced with CD19 CAR+DN TGF-βRI or CD19 CAR+DN TGF-βRII had less pSMAD2 and pSMAD3 induction (roughly 4-fold less induction of pSMAD2 and 2-fold less induction of pSMAD3, p-value <0.01). Further, the level of pSMAD2 and pSMAD3 induction in TGFβ1 treated T cells transduced with CD19 CAR+DN TGF-βM or CD19 CAR+DN TGF-βRII was equivalent to pSMAD2 and pSMAD3 levels in control transduced T cells co-treated with TGFβ1 and a small molecule inhibitor of TGF-βRI LY57299. This data confirms that DN TGF-βRI and DN TGF-βRII limit the suppressive pSMAD signaling in T cells that is induced by TGF-β1.

A second construct was made expressing PSMA CAR (a PSMA scFv+4-1BB intracellular domain+CD3ζ intracellular domain) followed by DN TGF-βRI or DN TGF-βRII. To determine if the truncated, dominant-negative receptor could limit pSMAD induction in this CAR context, $CD3^+$ cells were isolated from primary human peripheral blood mononuclear cells (PBMCs) and transduced with a construct containing PSMA CAR only, PSMA CAR+DN TGF-βM, or PSMA CAR+DN TGF-βRII. Total T cells were stimulated with TGF-β1 (5 ng/mL, 30 minutes), prepared whole cell lysates, and quantified pSMAD2 and pSMAD3 by LUMINEX®. The results are described in Table 4b.

TABLE 4b

PSMA CAR + Dominant-Negative TGF-βRI Receptors inhibit TGF-β1 induced pSMAD signaling

| Trial Group | pSMAD2 (MFI) | | pSMAD3 (MFI) | |
|---|---|---|---|---|
| No TGF-β | | | | |
| PSMA CAR | 170.7 | 86.1 | 101.3 | 32 |
| PSMA CAR + DN TGF-βRI | 208.9 | 227.9 | 9.5 | 60 |
| PSMA CAR + DN TGF-βRII | 96.6 | 168.4 | 47.7 | 116 |
| TGF-β1 | | | | |
| PSMA CAR | 8,089.6 | 9,107.6 | 2,336.5 | 2,258.9 |
| PSMA CAR + DN TGF-βRI | 4,122.9 | 4,627.2 | 953.2 | 1,100 |
| PSMA CAR + DN TGF-βRII | 1,889.4 | 2,100.5 | 1,038.6 | 870 |

TGF-β1 stimulated T cells expressing only PSMA CAR induced pSMAD2 and pSMAD3 by 8,500-fold and 2,200-fold respectively whereas TGF-β1 stimulated cells transduced with PSMA CAR+DN TGF-βRI or PSMA CAR+DN TGF-βRII had less pSMAD2 and pSMAD3 induction (roughly 2-fold less induction, p-value <0.05). Thus, the data of Tables 4a and 4b confirm that DN TGF-βRI and DN TGF-βRII limit the TGF-β1 mediated pSMAD signaling in CAR T cells expressing two different scFvs and in combination with both CD28 and 4-1BB co-stimulation.

Example 2

CD19 CAR positive T cells were co-cultured with mitomycin (Sigma Aldrich), treated Nalm6 target cells from American Type Culture Company (ATCC, Manassas, VA) at a 1:1 ratio for seven days. Target cells were added every other day at a 1:1 ratio based on the number of CAR' T cells as measured by counting beads and flow cytometry. For TGFβ1 treated groups, acid activated TGFβ1 (5 ng/mL) was added to co-culture media (RPMI+10% FBS) every other day.

Although in vivo CAR T cell efficacy in murine tumor models is generally considered the gold standard for predicating clinical efficacy, it has been determined that repeat stimulation with targets in a long-term in vitro killing assay often correlates with in vivo results. Therefore, a serial stimulation assay was used to measure CD19 CAR T cell expansion and tested whether DN TGF-βRI and DN TGF-βRII could limit the suppressive effects of TGF-β1 in this assay.

To determine the consequence of TGF-β1 on CD19 CART cell function, CD19 CAR T cells were stimulated three times in one week with CD19⁺ Nalm6 target cells, and target mediated CAR T cell expansion was measured. The results are described in Table 5.

TABLE 5

CD19 CAR + Dominant-Negative TGF-βRI Receptors T cell Expansion Assay

| Trial Group | CAR Expansion Day 7 | |
| --- | --- | --- |
| | Control | TGF-β1 |
| CD19 CAR | 7.3 | 0.9 |
| CD19 CAR + DN TGF-βRI | 10.2 | 11.1 |
| CD19 CAR + DN TGF-βRII | 5.9 | 8.8 |

The results indicate TGF-β1 suppresses CD19 CAR T cell expansion by approximately 7-fold in the assay as compared to vehicle treatment alone. To determine if DN TGF-βRI or DN TGF-βRII could rescue CD19 CAR T cell function in this repeat stimulation assay with TGF-β1, T cells were transduced with CD19 CAR+TGF-βRI or CD19 CAR+TGF-βRII and their expansion was measured after seven days with serial target stimulation in the presence and absence of TGF-β1. The results indicate that TGF-βRI rescues the suppressive effects of TGF-131 on CD19 CAR T cell expansion.

Example 3

CAR positive T cells were co-cultured with K562 target cells obtained from American Type Culture Company (ATCC, Manassas, VA) engineered to express prostate specific membrane antigen (PSMA). Co-culturing for 96 hours, cells were spun down and supernatants were collected. Supernatants were analyzed for interferon gamma (IFNγ) in LUMINEX® multiplex assays and analyzed on the LUMINEX® system (ThermoFisher Scientific). For some groups acid activated TGF-β1 was added at 5 ng/mL to the culture media at the start of the trial. CAR T cells mediate their cytolytic effect on tumor cells by secretion of cytotoxic molecules including IFNγ. The effect of exogenous TGF-β1 was tested on IFNγ production from PSMA CAR T cells in culture with PSMA⁺ target cells. The results are described in Table 6.

TABLE 6

PSMA CAR + Dominant-Negative TGF-β Receptors IFNγ production

| Trial Group | IFNγ (pg/ml) | |
| --- | --- | --- |
| No TGF-β | | |
| PSMA CAR | 9,938.2 | 13,320.6 |
| PSMA CAR + DN TGF-βRI | 16,145.3 | 14,368.6 |
| PSMA CAR + DN TGF-βRII | 13,477.9 | 12,470.8 |
| TGF-β1 | | |
| PSMA CAR | 2,297.53 | 4,041.2 |
| PSMA CAR +DN TGF-βRI | 10,959.1 | 15,490.0 |
| PSMA CAR +DN TGF-βRII | 14,898.6 | 12,495.7 |

It was found that exogenous TGF-β1 at 5 ng/mL given every two days reduced CAR T cell production of IFNγ over 96 hours by more than three-fold. Further, it was found that TGF-β treated T cells transduced with PSMA CAR+DN TGF-βRI or PSMA CAR+DN TGF-βRII had no reduction in IFNγ production in response to PSMA⁺ target cells and produced more IFNγ than PSMA CAR T cells treated with TGF-β1 and co-cultured with PSMA⁺ target cells. This data suggests that DN TGF-β Receptors restore the functional properties of both CD19 CAR T cells and PSMA CAR T cells challenged by TGF-β1 suppression.

Example 4

Further trials were conducted using the DN TGF-βRI of SEQ ID NO: 10 and the DN TGF-βRII of SEQ ID NO: 14 each with the CAR construct shown below:
 a. GPC3: (a GPC3 scFV+CD28 intracellular domain+ CD3ζ intracellular domain); and
 b. GPC3: (a GPC3 scFV+4-1BB intracellular domain+ CD3ζ intracellular domain) of SEQ ID NO: 45. Similar to the previous trials, CD3⁺ cells were isolated from primary human peripheral blood mononuclear cells (PBMCs) and transduced with the GPC3 constructs above. Background levels of pSMAD2 and pSMAD3 levels in all engineered T cells are shown in Table 7. TGF-β1 stimulated T cells expressing only GPC3 CAR induced pSMAD2 and pSMAD3 by 10,000-fold and 700-fold respectively whereas TGF-β1 stimulated cells transduced with GPC3 CAR+DN TGF-βRII (as shown in SEQ ID NO: 47) had significantly less pSMAD2 and pSMAD3 induction (roughly 20-fold less induction of pSMAD2 and 4-fold less induction of pSMAD3, p-value <0.01). GPC3 CAR+DN TGF-βRI did limit pSMAD2 and pSMAD3 induction (roughly 3-fold less induction of pSMAD2 with 4-1BB co-stimulation and 1.3-fold less induction of pSMAD3 with 4-1BB co-stimulation). The results are described in Table 7.

TABLE 7

GPC3 CAR + Dominant-Negative TGF-β Receptors inhibit TGF-β induced pSMAD signaling

| Trial Group | pSMAD2 (MFI) | | pSMAD3 (MFI) | |
|---|---|---|---|---|
| No TTGF-β1 | | | | |
| Untransduced cells | 5.9 | 0.9 | 5.1 | 2.4 |
| GPC3/CD28 CAR | 12.4 | 12.2 | 10.9 | 7.3 |
| GPC3/CD28 CAR + DN TGF-βRI | 12.8 | 2.6 | 8.0 | 1.1 |
| GPC3/CD28 CAR +DN TGF-βRII | 3.6 | 1.7 | 6.3 | 3.2 |
| GPC3/4-1BB CAR | 3.7 | 6.4 | 4.6 | 4.5 |
| GPC3/4-1BB CAR + DN TGF-βRI | 9.2 | 7.7 | 6.1 | 8.7 |
| GPC3/4-1BB CAR + DN TGF-βRII | 6.0 | 8.2 | 4.7 | 3.5 |
| TGF-β1 | | | | |
| Untransduced cells | 1064.2 | 1123.3 | 521.3 | 628.3 |
| GPC3/CD28 CAR | 1161.8 | 1347.3 | 742.9 | 798.9 |
| GPC3/CD28 CAR + DN TGF-βRI | 1079.5 | 901.5 | 641.8 | 706.7 |
| GPC3/CD28 CAR + DN TGF-βRII | 121.8 | 77.4 | 220.1 | 276.6 |
| GPC3/4-1BB CAR | 989.1 | 965.7 | 701.1 | 722.0 |
| GPC3/4-1BB CAR + DN TGF-βRI | 179.1 | 500.9 | 331.3 | 740.9 |
| GPC3/4-1BB CAR + DN TGF-βRII | 19.7 | 50.8 | 113.1 | 143.1 |

In addition, GPC3 CAR positive T cells were co-cultured with Hep3B target cells from American Type Culture Company (ATCC, Manassas, VA). Target cells were added two-times per week every three to four days and the number of CAR⁺ T cells was measured by counting beads and flow cytometry. For TGF-β1 treated groups, acid activated TGF-β1 (5 ng/mL) was added to co-culture media (RPMI+10% FBS) two-times per week every three to four days. The results are described in Table 8.

TABLE 8

GPC3 CAR + Dominant-Negative TGF-β Receptors in T cell expansion assay

| Cell population | GPC3 CAR⁺ Cell number | | |
|---|---|---|---|
| No TGF-β1 | | | |
| Untransduced cells | 2,090 | 702 | 1,090 |
| GPC3/CD28 CAR | 1,800,000 | 1,520,000 | 1,310,000 |
| GPC3/CD28 CAR + DN TGF-βRI | 2,260,000 | 2,600,000 | 2270000 |
| GPC3/CD28 CAR + DN TGF-βRII | 3,080,000 | 2,860,000 | 2,660,000 |
| GPC3/4-1BB CAR | 871,000 | 1,040,000 | 1,870,000 |
| GPC3/4-1BB CAR + DN TGF-βRI | 1,520,000 | 1,480,000 | 2,150,000 |
| GPC3/4-1BB CAR + DN TGF-βRII | 3,430,000 | 3,120,000 | 3,110,000 |
| TGF-β1 | | | |
| Untransduced cells | 786 | 476 | 786 |
| GPC3/CD28 CAR | 178,000 | 131,000 | 72,500 |
| GPC3/CD28 CAR + DN TGF-βRI | 305,000 | 300,000 | 277,000 |
| GPC3/CD28 CAR + DN TGF-βRII | 824,000 | 955,000 | 1,050,000 |
| GPC3/4-1BB CAR | 115,000 | 157,000 | 366,000 |
| GPC3/4-1BB CAR + DN TGF-βRI | 331,000 | 339,000 | 642,000 |
| GPC3/4-1BB CAR + DN TGF-βRII | 2,890,000 | 2,380,000 | 2,120,000 |

Example 5

In addition to the experiments above, the activity of DN TGF-βRI with DN TGF-βRII in the CD19, PSMA and GPC3 constructs described herein are evaluated in in vivo animal models. The study evaluates the receptor in pSMAD reduction, CAR cell expansion and cytokine production as described herein.

Example 6

An engineered, dominant-negative TGF-β receptor Type 2 (DN TGF-βRII) construct was made according to the sequence of SEQ ID NO: 33. This construct is 394 amino acids in length and includes a signal peptide domain from amino acid 1-22; a tag sequence from amino acid 23-32; an extracellular domain from amino acid 33-169 of wild-type TGF-βRII; a linker sequence from amino acid 170-171, a transmembrane domain from IL-7Rα from amino acid 172-194 of SEQ ID NO: 20 having a "CPT" insertion; and an intracellular domain from amino acid 195-394 from IL-7Rα.

CD3⁺ cells isolated from human PBMCs were transduced with constructs comprising the amino acid sequence of SEQ ID NO: 33. T cells were cultured in X-VIVO™ media without serum for two hours before 30 minutes of stimulation with 1 ng/mL of soluble recombinant TGF-β1 that was reconstituted in acid as recommended by the manufacturer (R&D Systems). Cells were then collected by centrifugation and lysed with RIPA buffer+protease and phosphatase inhibitors (ThermoFisher Scientific) before LUMINEX® analysis for pSMAD2, pSMAD3, pERK, and pSTAT5. Background levels of pSMAD2 and pSMAD3 levels in all engineered T cells were very low. TGF-β1 stimulated T cells induced pSMAD2 and pSMAD3 by 4,000-fold and 1,500-fold respectively whereas TGF-β1 stimulated cells transduced with the DN TGF-βRII construct had significantly less pSMAD2 and pSMAD3 induction (roughly 25-fold less induction of pSMAD2 and 11-fold less induction of pSMAD3, p-value <0.01) while pERK and pSTAT5 signaling was elevated in chimeric transduced T cells (28-fold higher for pERK and almost 80-fold higher pSTAT5). Increased pERK and pSTAT signaling were not dependent upon exposure to TGF-β1 and were elevated with and without exposure due to IL-7Rα mediated constitutive signaling. The results are described in Table 9.

TABLE 9

Chimeric Receptor for Dominant-Negative TGF-βRII Receptor inhibits TGF-β1 induced pSMAD signaling and enhances pERK and pSTAT5 signaling

| Trial Group | pSMAD2 (MFI) | | pSMAD3 (MFI) | | pERK (MFI) | | pSTAT5 (MFI) |
|---|---|---|---|---|---|---|---|
| No TGF-β | | | | | | | |
| Untransduced cells | 7.5 | 14.5 | 6.3 | 7.8 | 3.3 | 7.3 | 1543 |
| DN TGF-βII | 21.5 | 26 | 15.8 | −0.25 | 102.3 | 141.3 | 135,184 |
| TGF-β1 | | | | | | | |
| Untransduced cells | 4544 3822 | 3529 1745 | 1266 | 1181 | 2.3 5.3 | 6.3 | 1485 |
| DN TGF-βRII | 114.5 160.5 | 178.5 163.8 | 98.8 | 110.8 135.3 | 126.3 | 125.8 | 106,591 |

Example 7

The codon-optimized sequence of the GPC3 targeting CAR construct of SEQ ID NO: 51 (CAR 1) was compared with two additional GPC3 targeting CAR constructs. The trials were conducted by generating the CAR constructs as shown below:
  a. Construct CAR 1: (a GPC3 scFv+4-1BB intracellular domain+CD3ζ intracellular domain) as shown in the codon-optimized sequence of SEQ ID NO: 51.
  b. Construct CAR 2: (a GPC3 scFv+4-1BB intracellular domain+CD3ζ intracellular domain as described in Li, Gastroenterology, 2020 and WO2019094482A1) having the nucleotide sequence as shown in SEQ ID NO: 53.

(SEQ ID NO: 53)
ATGCTTCTCCTGGTGACAAGCCTTCTGCTCTGTGAGTTACCACACCCAGC

ATTCCTCCTGATCCCACATATGGAGGTGCAGCTTGTTGAGTCTGGTGGAG

GATTGGTGCAGCCTGGAGGGTCATTGAGACTCTCATGTGCAGCCTCTGGA

TTCACCTTCAATAAGAATGCCATGAATTGGGTCCGCCAGGCTCCAGGAAA

GGGTTTGGAATGGGTTGGCCGCATAAGAAATAAAACTAATAATTATGCAA

CATATTATGCCGATTCAGTGAAAGCCAGGTTTACCATCTCCAGAGATGAT

TCAAAGAACTCACTCTATCTGCAAATGAACAGCTTGAAAACCGAGGACAC

AGCCGTGTACTATTGTGTGGCTGGTAACTCGTTTGCTTACTGGGGCCAAG

GGACTCTGGTCACTGTCTCTGCAGGCGGAGGCGGATCAGGTGGTGGCGGA

TCTGGAGGTGGCGGAAGCGACATTGTGATGACCCAGTCTCCAGACTCCCT

AGCTGTGTCACTGGGAGAGAGGGCCACTATCAACTGCAAGTCCAGTCAGA

GCCTTTTATATAGCAGCAATCAAAAGAACTACTTGGCCTGGTACCAACAG

AAACCAGGGCAGCCTCCTAAACTGCTGATTTACTGGGCATCCAGTAGGGA

ATCTGGGGTCCCTGATCGCTTCAGTGGCAGTGGATCTGGGACAGATTTCA

CTCTCACCATCAGCAGTCTGCAGGCTGAAGACGTGGCAGTTTATTACTGT

CAGCAATATTATAACTATCCGCTCACGTTCGGTCAGGGGACCAAGTTGGA

GATCAAAACTAGTACCACGACGCCAGCGCCGCGACCACCAACACCGGCGC

CCACCATCGCGTCGCAGCCCCTGTCCCTGCGCCCAGAGGCGTGCCGGCCA

GCGGCGGGGGGCGCAGTGCACACGAGGGGGCTGGACTTCGCCTGTGACAT

CTACATCTGGGCGCCCTTGGCCGGGACTTGTGGGGTCCTTCTCCTGTCAC

TGGTTATCACCAAACGGGGCAGAAAGAAACTCCTGTATATATTCAAACAA

CCATTTATGAGACCAGTACAAACTACTCAAGAGGAAGATGGCTGTAGCTG

CCGATTTCCAGAAGAAGAAGGAGGATGTGAACTGAGAGTGAAGTTCA

GCAGGAGCGCAGACGCCCCCGCGTACCAGCAGGGCCAGAACCAGCTCTAT

AACGAGCTCAATCTAGGACGAAGAGAGGAGTACGATGTTTTGGACAAGAG

ACGTGGCCGGGACCCTGAGATGGGGGGAAAGCCGAGAAGGAAGAACCCTC

AGGAAGGCCTGTACAATGAACTGCAGAAAGATAAGATGGCGGAGGCCTAC

AGTGAGATTGGGATGAAAGGCGAGCGCCGGAGGGGCAAGGGGCACGATGG

CCTTTACCAGGGTCTCAGTACAGCCACCAAGGACACCTACGACGCCCTTC

ACATGCAGGCCCTGCCCCCTCGCTGA.

c. Construct CAR 3: (a construct with a transgene having the same amino acid sequence as CAR 2, but where the nucleotide sequence has been optimized to minimize splicing and repeats) as shown in SEQ ID NO: 54.

(SEQ ID NO: 54)
ATGCTTCTCCTGGTGACAAGCCTTCTGCTCTGCGAATTACCACACCCAGC

ATTCCTCCTGATCCCACATATGGAGGTGCAGCTTGTTGAGTCTGGTGGAG

GATTGGTGCAGCCTGGAGGGTCATTGAGACTCTCATGTGCAGCCTCTGGA

TTCACCTTCAATAAGAATGCCATGAATTGGGTCCGCCAGGCTCCAGGAAA

GGGTTTGGAATGGGTTGGCCGCATAAGAAATAAAACTAATAATTATGCAA

CATATTATGCCGATTCAGTGAAAGCCAGGTTTACCATCTCCAGAGATGAT

TCAAAGAACTCACTCTATCTGCAAATGAACAGCTTGAAAACCGAGGACAC

AGCCGTGTACTATTGTGTGGCTGGAAACTCGTTTGCTTACTGGGGCCAAG

GGACTCTGGTCACTGTCAGCGCTGGAGGAGGCGGATCAGGTGGTGGCGGA

TCTGGAGGTGGCGGAAGCGACATTGTGATGACCCAGTCTCCAGACTCCCT

AGCTGTGTCACTGGGAGAGAGGGCCACTATCAACTGCAAGTCCAGTCAGA

GCCTTTTATATAGCAGCAATCAAAAGAACTACTTGGCCTGGTACCAGCAA

AAGCCAGGGCAGCCTCCTAAACTGCTGATTTACTGGGCATCCAGTAGGGA

ATCTGGGGTCCCTGATCGCTTCAGTGGCAGTGGATCTGGGACAGATTTCA

CTCTCACCATCAGCAGTCTGCAGGCTGAAGACGTGGCAGTTTATTACTGT

-continued
```
CAGCAATATTATAACTATCCGCTCACGTTCGGTCAGGGGACCAAGTTGGA

GATCAAAACTAGTACCACGACGCCAGCGCCGCGACCACCAACACCGGCGC

CCACCATCGCGAGTCAACCACTGTCCCTGAGGCCTGAAGCGTGCCGGCCA

GCGGCGGGGGCGCAGTGCACACGAGGGGGCTGGACTTCGCCTGTGACAT

CTACATCTGGGCGCCCTTGGCCGGGACTTGTGGGGTCCTTCTCCTGTCAC

TGGTTATCACCAAACGGGGCAGAAAGAAACTCCTGTATATATTCAAACAA

CCATTTATGAGACCAGTACAAACTACTCAAGAGGAAGATGGCTGTAGCTG

CCGATTTCCAGAAGAAGAAGAAGGAGGATGTGAACTGAGAGTGAAGTTCA

GCAGGAGCGCAGACGCCCCCGCGTACCAGCAAGGGCAGAACCAGCTCTAT

AACGAGCTCAATCTAGGACGAAGAGAGGAGTACGATGTTTTGGACAAGAG

GCGTGGCCGGGACCCTGAGATGGGGGAAAGCCGAGAAGGAAGAACCCTC

AGGAAGGCCTGTACAATGAACTGCAGAAAGATAAGATGGCGGAGGCCTAC

AGTGAGATTGGGATGAAAGGCGAGCGCCGGAGGGGCAAGGGCACGATGG

CCTTTACCAGGGTCTCAGTACAGCCACCAAGGACACCTACGACGCCCTTC

ACATGCAAGCTCTGCCCCTCGCTGA.
```

TABLE 10

CAR 1 enhanced transduction and expression efficiency

| | Untransduced | CAR 1 | CAR 2 | CAR 3 |
|---|---|---|---|---|
| % CAR + | 0.35 | 93.4 | 64.4 | 67.5 |
| MFI CAR + | NA | 21,098 | 2710 | 2770 |
| VCN % | 0 | 2.1 | 1.3 | 1.3 |

Example 8

CAR+ T cells ($5 \times 10^4$) manufactured, frozen, rested and stained as described previously were co-cultured with HCC target cells ($5 \times 10^4$) for 48 hours to induce cytokine release and supernatants were frozen at −80° C. Interferon gamma (IFNγ) concentrations were measured using Millipore MIL-LIPLEX® Map Human High Sensitivity T cell Panel (Cat #HSTCMAG-28PMX13BK) after diluting the supernatant 500 fold in PBS. The data in Table 11 illustrates that construct CAR 1 secretes less IFNγ than constructs CAR 2 and CAR 3 in the presence of GPC3− cell lines Hep3B GPC3 KO and Sk-Hep1. This data suggests that the CAR 1 construct induces less tonic activation than CAR 2 and CAR 3 constructs.

TABLE 11

CAR 1 decreased cytokine release in GPC3-target cells

| | Hep3B (pg/mL) | | | Hep3B GPC3 KO (pg/mL) | | | SK-HEP-1 (pg/mL) | | |
|---|---|---|---|---|---|---|---|---|---|
| CAR 1 | 56,292 | 63,609 | 85,286 | 332 | 332 | 880 | 2,449 | 1,080 | 701 |
| CAR 2 | 101,180 | 112,149 | 102,012 | 69,597 | 37,883 | 71,005 | 52,998 | 52,910 | 49,380 |
| CAR 3 | 71,840 | 62,824 | 65,578 | 62,458 | 55,749 | 68,293 | 53,349 | 50,821 | 59,334 |
| Un-transduced | 305* | 305* | 305* | 305* | 305* | 305* | 305* | 305* | 305* |

Similar to the previous trials, CD3+ cells were isolated from primary human peripheral blood mononuclear cells (PBMCs) and transduced with the GPC3 CAR constructs above in the presence of polybrene and at a multiplicity of infection of two, based on expression titer in Jurkat cells. At the end of manufacturing, cells were frozen down in Cryostor® CS5 and stored in liquid nitrogen until thawing. Upon thawing, cells were rested in T cell culture medium overnight with 100 UI/mL IL-2, washed, and stained with Live/Dead™ Violet diluted at 1:1000, recombinant human GPC3 (rhGPC3) fluorescently conjugated to DyLight™ 650 diluted at 1:200, and anti-CD3 BV650 at 1:100 in PBS for 30 min at 4° C. The DNA of a pellet of $1 \times 10^5$ cells was extracted in QuickExtract™ Buffer, frozen, and used to measure average vector copy number (VCN) by droplet digital PCR quantifying frequency of integrated virus per cell. Percentage CAR+ cells are defined as percentage of cells staining with rhGPC3 amongst Live/Dead™ negative, CD3+ positive cells, and Mean Fluorescence Intensity (MFI) of CAR+, and Vector copy number (VCN) are given in the example. As seen in Table 10, the higher VCN, % CAR+ construct CAR 1 suggests that its transduction efficiency is higher than that of constructs CAR 2 and CAR 3. Construct CAR 1 also has higher MFI of CAR+ cells, which could indicate more efficient expression or higher affinity of the CAR to rhGPC3.

Example 9

T cells transduced with constructs CAR 1, CAR 2, and CAR 3, or untransduced (UT) were manufactured as described above and tested in vivo in a Hep3B xenograft model in NSG mice. Cells at $2 \times 10^6$ Hep3B 2.1-7 cells were implanted into NSG mice on the first day of the experiment. Every three to four days thereafter, tumor volume was measured using calipers. On day 14, when tumors reached mean size 149 mm³, animals were divided into groups and treated with either a PBS vehicle, non-transduced T cells, GPC3 CAR T cells made by constructs CAR 1, CAR 2, or CAR 3 at either $6 \times 10^6$ CAR+ cells or $2 \times 10^6$ CAR+ cells via intravenous injection. Tumor volumes throughout the study are described in Tables 12-19 below. The CAR T cells made with construct CAR 1 were more potent at $6 \times 10^6$ and $2 \times 10^6$ doses than constructs CAR 2 and CAR 3 as evidenced by control of tumor growth.

TABLE 12

PBS Vehicle treatment of Hep3B Tumor Cells

| Days Post Tumor Implant | Tumor volume (mm³) | | | |
|---|---|---|---|---|
| 14 | 175 | 167 | 116 | 106 |
| 15 | 195 | 196 | 118 | 137 |
| 17 | 302 | 334 | 199 | 138 |
| 20 | 548 | 389 | 358 | 171 |

TABLE 12-continued

PBS Vehicle treatment of Hep3B Tumor Cells

| Days Post Tumor Implant | Tumor volume (mm³) | | | |
|---|---|---|---|---|
| 22 | 882 | 818 | 488 | 252 |
| 24 | 1,018 | 1,061 | 603 | 412 |
| 27 | 1,064 | 1,181 | 1,078 | 772 |
| 29 | 1,098 | 1,389 | 1,305 | 1,059 |
| 31 | 1,237 | 1,240 | 1,533 | 1,156 |
| 34 | 2,601 | | 2,158 | 1,630 |
| 36 | | | | 1,849 |
| 38 | | | | 2,440 |

TABLE 13

Non-Transduced T Cell treatment of Hep3B Tumor Cells

| Days Post Tumor Implant | Tumor volume (mm³) | | | | | | | | | |
|---|---|---|---|---|---|---|---|---|---|---|
| 14 | 111 | 178 | 174 | 125 | 101 | 144 | 139 | 116 | 110 | 152 |
| 15 | 150 | 191 | 176 | 229 | 118 | 188 | 165 | 136 | 125 | 193 |
| 17 | 157 | 265 | 184 | 240 | 153 | 221 | 185 | 156 | 132 | 201 |
| 20 | 170 | 417 | 185 | 388 | 215 | 513 | 237 | 203 | 178 | 342 |
| 22 | 251 | 656 | 281 | 691 | 356 | 612 | 340 | 349 | 304 | 570 |
| 24 | 307 | 907 | 381 | 696 | 544 | 840 | 500 | 466 | 330 | 586 |
| 27 | 630 | 1,111 | 679 | 1,186 | 893 | 1,157 | 964 | 895 | 728 | 1,191 |
| 29 | 690 | 1,240 | 752 | 1,267 | 1,022 | 1,426 | 1,072 | 1,175 | 945 | 1,219 |
| 31 | 723 | 1,269 | 771 | 1,296 | 1,055 | 1,004 | 1,152 | 1,294 | 955 | 1,171 |
| 34 | 1,183 | 1,929 | 1,504 | 1,645 | 1,548 | | 1,730 | 1,522 | 1,385 | 1,775 |
| 36 | 1,314 | 2,167 | 1,577 | 2,056 | 1,958 | | 1,808 | 1,705 | 1,471 | 1,865 |
| 38 | 1,865 | | 1,886 | | 3,036 | | 2,851 | 3,103 | 2,079 | 2,310 |
| 41 | 2,241 | | 3,443 | | | | | | | |

TABLE 14

Treatment with 6 × 10⁶ CAR 1 T cells

| Days Post Tumor Implant | Tumor volume (mm³) | | | | | | | | | |
|---|---|---|---|---|---|---|---|---|---|---|
| 14 | 164 | 189 | 136 | 148 | 153 | 170 | 174 | 102 | 112 | 100 |
| 15 | 193 | 256 | 172 | 153 | 186 | 183 | 212 | 126 | 128 | 130 |
| 17 | 207 | 277 | 173 | 194 | 222 | 197 | 214 | 130 | 133 | 149 |
| 20 | 282 | 429 | 191 | 238 | 292 | 212 | 215 | 163 | 144 | 166 |
| 22 | 377 | 509 | 257 | 329 | 377 | 383 | 289 | 213 | 149 | 216 |
| 24 | 102 | 479 | 144 | 224 | 352 | 294 | 254 | 215 | 127 | 155 |
| 27 | 0 | 172 | 64 | 132 | 124 | 97 | 97 | 0 | 75 | 74 |
| 29 | 0 | 149 | 0 | 122 | 79 | 79 | 79 | 0 | 0 | 0 |
| 31 | 0 | 0 | 0 | 64 | 0 | 0 | 0 | 0 | 0 | 0 |
| 34 | 0 | 0 | 0 | 100 | 0 | 0 | 0 | 0 | 0 | 0 |
| 36 | 0 | 0 | 0 | 89 | 0 | 0 | 0 | 0 | 0 | 0 |
| 38 | 0 | 0 | 0 | 68 | 0 | 0 | 0 | 0 | 0 | 0 |
| 41 | 0 | 0 | 0 | 66 | 0 | 0 | 0 | 0 | 0 | 0 |
| 43 | 0 | 0 | 0 | 0 | 0 | 0 | 0 | 0 | 0 | 0 |
| 45 | 117 | 96 | 81 | 102 | 247 | 236 | 0 | 0 | 0 | 0 |
| 48 | 139 | 118 | 90 | 120 | 275 | 274 | 0 | 0 | 0 | 75 |
| 50 | 163 | 125 | 112 | 121 | 296 | 280 | 83 | 0 | 0 | 98 |

TABLE 15

Treatment with 2 × 10⁶ CAR 1 T cells

| Days Post Tumor Implant | Tumor volume (mm³) | | | | | | | | | |
|---|---|---|---|---|---|---|---|---|---|---|
| 14 | 101 | 118 | 190 | 145 | 176 | 155 | 192 | 104 | 196 | 106 |
| 15 | 121 | 166 | 212 | 166 | 205 | 194 | 231 | 161 | 307 | 117 |
| 17 | 122 | 195 | 224 | 178 | 228 | 218 | 265 | 162 | 353 | 122 |
| 20 | 122 | 208 | 266 | 181 | 279 | 279 | 427 | 179 | 534 | 123 |
| 22 | 133 | 266 | 434 | 282 | 373 | 574 | 719 | 212 | 884 | 190 |
| 24 | 135 | 304 | 459 | 310 | 651 | 644 | 813 | 240 | 927 | 197 |
| 27 | 115 | 256 | 229 | 509 | 857 | 652 | 661 | 314 | 904 | 102 |
| 29 | 0 | 141 | 189 | 779 | 926 | 651 | 872 | 332 | 895 | 0 |
| 31 | 0 | 0 | 170 | 866 | 873 | 651 | 678 | 214 | 653 | 0 |
| 34 | 0 | 0 | 311 | 1153 | | 723 | 1,173 | 214 | 896 | 0 |
| 36 | 0 | 0 | 360 | 1268 | | 777 | 1,278 | 0 | 1,083 | 0 |
| 38 | 0 | 0 | 351 | 2214 | | 1,126 | 1,326 | 0 | 1,501 | 0 |
| 41 | 0 | 0 | 330 | | | 1,341 | 1,110 | 0 | 1,787 | 0 |
| 43 | 0 | 0 | 371 | | | 1,415 | 993 | 0 | 2,456 | 0 |
| 45 | 0 | 0 | 453 | | | 1,425 | | 0 | | 0 |
| 48 | 0 | 0 | 487 | | | 1,449 | | 0 | | 0 |
| 50 | 0 | 0 | 501 | | | 1,485 | | 0 | | 0 |

TABLE 16

Treatment with 6 × 10⁶ CAR 2 T cells

| Days Post Tumor Implant | Tumor volume (mm³) | | | | | | | | | |
|---|---|---|---|---|---|---|---|---|---|---|
| 14 | 160 | 152 | 196 | 189 | 137 | 158 | 147 | 122 | 196 | 113 |
| 15 | 164 | 167 | 227 | 211 | 137 | 162 | 151 | 133 | 202 | 114 |
| 17 | 168 | 184 | 242 | 232 | 135 | 187 | 154 | 147 | 215 | 117 |
| 20 | 245 | 255 | 262 | 330 | 145 | 210 | 223 | 156 | 248 | 121 |
| 22 | 289 | 318 | 348 | 457 | 222 | 283 | 265 | 211 | 278 | 132 |
| 24 | 277 | 359 | 360 | 501 | 258 | 287 | 299 | 204 | 284 | 133 |
| 27 | 141 | 438 | 423 | 544 | 306 | 216 | 215 | 70 | 315 | 0 |
| 29 | 115 | 470 | 342 | 821 | 426 | 406 | 294 | 64 | 423 | 0 |
| 31 | 124 | 584 | 428 | 821 | 472 | 545 | 333 | 0 | 457 | 0 |
| 34 | 148 | 988 | 509 | | 651 | 582 | 392 | 0 | 706 | 0 |
| 36 | 159 | 1,074 | 592 | | 698 | 676 | 412 | 0 | 765 | 0 |

TABLE 16-continued

Treatment with 6 × 10⁶ CAR 2 T cells

| Days Post Tumor Implant | Tumor volume (mm³) | | | | | | | | | |
|---|---|---|---|---|---|---|---|---|---|---|
| 38 | 98 | 1,610 | 1,134 | | 934 | 1,579 | 677 | 0 | 1,251 | 0 |
| 41 | 87 | 1,790 | 1,178 | | 1,102 | 1,948 | 841 | 0 | 1,522 | 0 |
| 43 | 82 | 2,073 | 1,593 | | 1,352 | 2,511 | 1,480 | 0 | 2,264 | 0 |
| 45 | 109 | | 1,635 | | 1,360 | | 1,546 | 0 | | 0 |
| 48 | 148 | | 1,689 | | 1,434 | | 1,605 | 0 | | 0 |
| 50 | 190 | | 1,878 | | 1,445 | | 1,689 | 0 | | 0 |

TABLE 17

Treatment with 2 × 10⁶ CAR 2 T cells

| Days Post Tumor Implant | Tumor volume (mm³) | | | | | | | | | |
|---|---|---|---|---|---|---|---|---|---|---|
| 14 | 107 | 160 | 164 | 116 | 187 | 185 | 147 | 117 | 182 | 180 |
| 15 | 117 | 179 | 172 | 116 | 197 | 191 | 161 | 121 | 191 | 194 |
| 17 | 129 | 198 | 206 | 123 | 206 | 202 | 169 | 127 | 216 | 210 |
| 20 | 265 | 301 | 337 | 123 | 251 | 284 | 353 | 167 | 404 | 268 |
| 22 | 269 | 330 | 372 | 129 | 267 | 343 | 399 | 213 | 515 | 283 |
| 24 | 374 | 424 | 511 | 170 | 351 | 478 | 502 | 377 | 504 | 390 |
| 27 | 417 | 369 | 836 | 179 | 410 | 715 | 753 | 374 | 926 | 433 |
| 29 | 437 | 465 | 997 | 187 | 580 | 912 | 926 | 507 | 1,330 | 572 |
| 31 | 469 | 517 | 1,069 | 210 | 626 | 933 | 1,009 | 549 | 1,354 | 611 |
| 34 | 708 | 657 | | 241 | 705 | 1,676 | 1,452 | 809 | 1,534 | 882 |
| 36 | 759 | 736 | | 274 | 771 | 1,777 | 1,564 | 927 | 1,758 | 935 |
| 38 | 1,030 | 1,373 | | 289 | 1,281 | 2,568 | 2,029 | 1,624 | 3,104 | 1,876 |
| 41 | 611 | 1,465 | | 254 | 1,405 | | | 1,819 | | 2,007 |
| 43 | 481 | 1,597 | | 256 | 1,423 | | | 1,939 | | |
| 45 | 518 | 1,616 | | 278 | 1,440 | | | 2,018 | | |
| 48 | 522 | 1,639 | | 284 | 1,473 | | | | | |
| 50 | 526 | 1,657 | | 286 | 1,509 | | | | | |

TABLE 18

Treatment with 6 × 10⁶ CAR 3 T cells

| Days Post Tumor Implant | Tumor volume (mm³) | | | | | | | | | |
|---|---|---|---|---|---|---|---|---|---|---|
| 14 | 131 | 197 | 161 | 143 | 185 | 180 | 200 | 105 | 106 | 155 |
| 15 | 134 | 207 | 163 | 167 | 199 | 185 | 238 | 112 | 125 | 160 |
| 17 | 135 | 229 | 178 | 174 | 262 | 194 | 258 | 130 | 129 | 175 |
| 20 | 141 | 254 | 187 | 187 | 390 | 229 | 337 | 161 | 164 | 271 |
| 22 | 145 | 270 | 217 | 251 | 391 | 239 | 387 | 179 | 178 | 427 |
| 24 | 89 | 153 | 150 | 182 | 385 | 254 | 317 | 135 | 182 | 431 |
| 27 | 69 | 126 | 97 | 155 | 165 | 316 | 225 | 0 | 158 | 415 |
| 29 | 0 | 118 | 96 | 125 | 160 | 496 | 221 | 0 | 154 | 602 |
| 31 | 0 | 129 | 147 | 142 | 169 | 561 | 236 | 0 | 190 | 707 |
| 34 | 0 | 137 | 254 | 236 | 208 | 713 | 368 | 0 | 212 | 1,271 |
| 36 | 0 | 91 | 206 | 257 | 157 | 854 | 285 | 0 | 284 | 1,414 |
| 38 | 0 | 77 | 146 | 108 | 90 | 1,308 | 129 | 0 | 293 | 1,729 |
| 41 | 0 | 72 | 143 | 94 | 76 | 1,676 | 125 | 0 | 275 | 2,103 |
| 43 | 0 | 69 | 137 | 94 | 0 | 2,489 | 123 | 0 | 269 | |
| 45 | 0 | 97 | 163 | 132 | 0 | | 133 | 0 | 296 | |
| 48 | 0 | 106 | 186 | 139 | 0 | | 155 | 0 | 313 | |
| 50 | 0 | 120 | 202 | 149 | 0 | | 173 | 0 | 350 | |

TABLE 19

Treatment with 2 × 10⁶ CAR 3 T cells

| Days Post Tumor Implant | Tumor volume (mm³) | | | | | | | | | |
|---|---|---|---|---|---|---|---|---|---|---|
| 14 | 186 | 194 | 105 | 135 | 130 | 196 | 120 | 147 | 183 | 167 |
| 15 | 190 | 233 | 142 | 139 | 136 | 228 | 124 | 149 | 205 | 179 |
| 17 | 217 | 240 | 162 | 141 | 138 | 268 | 130 | 154 | 255 | 188 |
| 20 | 372 | 276 | 277 | 145 | 134 | 436 | 133 | 197 | 446 | 191 |
| 22 | 446 | 432 | 320 | 232 | 151 | 552 | 168 | 273 | 584 | 209 |
| 24 | 577 | 456 | 334 | 246 | 155 | 505 | 146 | 205 | 773 | 147 |
| 27 | 668 | 605 | 458 | 284 | 186 | 537 | 150 | 212 | 883 | 155 |
| 29 | 901 | 877 | 638 | 408 | 184 | 777 | 140 | 215 | 1,162 | 177 |
| 31 | 1,070 | 918 | 693 | 462 | 203 | 891 | 153 | 251 | 1,167 | 235 |
| 34 | 1,319 | 1,112 | 845 | 643 | 222 | 924 | 231 | 296 | 1,401 | 253 |
| 36 | 1,522 | 1,156 | 921 | 719 | 279 | 1,092 | 282 | 365 | 1,414 | 314 |
| 38 | | 1,893 | 1,765 | 1,487 | 317 | 1,871 | 279 | 436 | 1,744 | 636 |
| 41 | | 2,070 | 2,211 | 1,617 | 408 | 2,238 | 332 | 491 | 1,787 | 636 |
| 43 | | | | 2,134 | 537 | | 417 | 495 | | 703 |
| 45 | | | | | 556 | | 461 | 514 | | 723 |
| 48 | | | | | 580 | | 514 | 521 | | 737 |
| 50 | | | | | 600 | | 530 | 535 | | 825 |

Example 10

A GPC3 CAR-DN TGF-βRII construct was made as shown in SEQ ID NO: 47, and tested on Hep3B tumor cells. 2×10⁶ Hep3B 2.1-7 cells were implanted into NOD-SCID IL-2R gamma$^{null}$ (NSG) mice on the first day of the experiment. Every three to four days thereafter, tumor volume was measured using calipers. On day 14, when tumors reached mean size 150 mm³, animals were divided into groups and treated with either a PBS vehicle, non-transduced T cells, GPC3 CAR T cells or GPC3 CAR+DN TGF-βRII T cells at either 1×10⁶ CAR⁺ cells or 4×10⁶ CAR⁺ cells via intravenous injection. Animals exceeding the study endpoint of tumor volume of 2000 mm³ were removed from the study. Tumor volumes throughout the study are described in Tables 20-25 below. The addition of DN TGF-βRII improved potency of the GPC3 scFv, with improvement in tumor control at 1×10⁶ CAR⁺ cell dose or higher.

TABLE 20

PBS Vehicle treatment of Hep3B Tumor Cells

| Days Post Tumor Implant | Tumor volume (mm³) | | | |
|---|---|---|---|---|
| 14 | 172 | 108 | 196 | 144 |
| 16 | 221 | 172 | 288 | 221 |
| 19 | 405 | 256 | 666 | 550 |
| 21 | 600 | 365 | 936 | 600 |
| 23 | 726 | 500 | 1,008 | 787 |
| 26 | 847 | 666 | 1,183 | 847 |
| 28 | 1,352 | 936 | 1,470 | 1,152 |
| 30 | 1,913 | 1,099 | 1,800 | 1,352 |
| 33 | 2,304 | 1,800 | 2,176 | 1,764 |
| 35 | — | 2,048 | — | 2,025 |

TABLE 21

Non-Transduced T Cell treatment of Hep3B Tumor Cells

| Days Post Tumor Implant | Tumor volume (mm³) | | | | | | | |
|---|---|---|---|---|---|---|---|---|
| 14 | 196 | 172 | 126 | 196 | 172 | 162 | 196 | 126 |
| 16 | 288 | 256 | 196 | 365 | 256 | 320 | 365 | 172 |
| 19 | 405 | 365 | 288 | 666 | 446 | 446 | 500 | 245 |
| 21 | 666 | 666 | 405 | 726 | 527 | 650 | 666 | 320 |
| 23 | 726 | 787 | 550 | 726 | 787 | 787 | 936 | 405 |
| 26 | 787 | 1,008 | 726 | 936 | 936 | 1,008 | 1,008 | 600 |
| 28 | 1,008 | 1,183 | 936 | — | 1,008 | 1,268 | 1,183 | 847 |
| 30 | 1,268 | 1,470 | 1,372 | — | 1,268 | 1,800 | 1,470 | 1,080 |
| 33 | 1,666 | 2,176 | — | — | 1,764 | 2,304 | 2,048 | 1,568 |
| 35 | 2,025 | — | — | — | 2,025 | — | — | 2,048 |

TABLE 22

GPC3 scFv1-BBz 4 × 10⁶ cell treatment of Hep3B Tumor Cells

| Days Post Tumor Implant | Tumor volume (mm³) | | | | | | | |
|---|---|---|---|---|---|---|---|---|
| 14 | 196 | 172 | 126 | 108 | 172 | 144 | 196 | 144 |
| 16 | 405 | 288 | 144 | 126 | 320 | 196 | 256 | 196 |
| 19 | 500 | 288 | 144 | 256 | 405 | 196 | 365 | 196 |
| 21 | 666 | 500 | 221 | 405 | 500 | 221 | 550 | 288 |
| 23 | 666 | 405 | 172 | 365 | 405 | 221 | 446 | 288 |
| 26 | 196 | 196 | 75 | 75 | 126 | 63 | 108 | 108 |
| 28 | 108 | 75 | 0 | 0 | 0 | 0 | 0 | 0 |
| 30 | 75 | 0 | 0 | 0 | 0 | 0 | 0 | 0 |
| 33 | 63 | 0 | 0 | 0 | 0 | 0 | 0 | 0 |
| 35 | 63 | 0 | 0 | 0 | 0 | 0 | 0 | 0 |
| 37 | 126 | 0 | 0 | 0 | 0 | 0 | 0 | 0 |
| 40 | 126 | 108 | 0 | 0 | 0 | 0 | 75 | 0 |
| 42 | 256 | 172 | 0 | 75 | 108 | 0 | 108 | 63 |
| 44 | 365 | 196 | 0 | 126 | 108 | 0 | 126 | 75 |
| 47 | 500 | 288 | 0 | 196 | 172 | 0 | 172 | 126 |
| 49 | 726 | 405 | 0 | 365 | 288 | 0 | 288 | 126 |
| 51 | 936 | 550 | 63 | 405 | 500 | 0 | 405 | 196 |
| 54 | 1,183 | 936 | 126 | 726 | 726 | 63 | 500 | 288 |
| 56 | 1,268 | 1,099 | 144 | 787 | 864 | 75 | 787 | 288 |

TABLE 23

GPC3 scFv1-BBz 1 × 10⁶ cell treatment of Hep3B Tumor Cells

| Days Post Tumor Implant | Tumor volume (mm³) | | | | | | | |
|---|---|---|---|---|---|---|---|---|
| 14 | 196 | 196 | 126 | 108 | 144 | 172 | 196 | 144 |
| 16 | 288 | 320 | 144 | 126 | 221 | 288 | 288 | 196 |
| 19 | 405 | 550 | 196 | 172 | 352 | 405 | 288 | 221 |
| 21 | 550 | 864 | 221 | 256 | 486 | 550 | 500 | 320 |
| 23 | 600 | 936 | 405 | 288 | 650 | 726 | 726 | 446 |
| 26 | 600 | 936 | 221 | 126 | 288 | 500 | 446 | 405 |
| 28 | 550 | 936 | 126 | 63 | 320 | 666 | 446 | 446 |
| 30 | 666 | 1,183 | 126 | 0 | 405 | 864 | 600 | 600 |
| 33 | 864 | 1,800 | 75 | 0 | 500 | 1,372 | 787 | 650 |
| 35 | 1,183 | 2,176 | 75 | 0 | 550 | 1,800 | 1,008 | 700 |
| 37 | 1,268 | — | 0 | 0 | 600 | 2,048 | 1,352 | 700 |
| 40 | 1,688 | — | 0 | 63 | 600 | — | 1,764 | 650 |
| 42 | 1,800 | — | 0 | 108 | 787 | — | 2,138 | 650 |
| 44 | 2,048 | — | 0 | 172 | 1,008 | — | — | 600 |
| 47 | — | — | 0 | 172 | 1,080 | — | — | 405 |
| 49 | — | — | 0 | 256 | 1,352 | — | — | 256 |
| 51 | | | 0 | 405 | 1,568 | | | 196 |
| 54 | | | 0 | 405 | 1,666 | | | 196 |
| 56 | | | 0 | 486 | 2,138 | | | 196 |

TABLE 24

GPC3 scFv1-BBz + DN TGF-βRII 4 × 10⁶ cell treatment of Hep3B Tumor Cells

| Days Post Tumor Implant | Tumor volume (mm³) | | | | | | | |
|---|---|---|---|---|---|---|---|---|
| 14 | 126 | 172 | 172 | 196 | 172 | 126 | 126 | 196 |
| 16 | 196 | 365 | 196 | 288 | 196 | 221 | 172 | 288 |
| 19 | 221 | 405 | 196 | 365 | 256 | 245 | 196 | 405 |
| 21 | 365 | 550 | 256 | 500 | 288 | 405 | 256 | 550 |
| 23 | 365 | 550 | 256 | 288 | 288 | 320 | 256 | 550 |
| 26 | 126 | 126 | 63 | 75 | 75 | 126 | 108 | 196 |
| 28 | 0 | 63 | 0 | 0 | 0 | 0 | 0 | 108 |
| 30 | 0 | 0 | 0 | 0 | 0 | 0 | 0 | 0 |
| 33 | 0 | 0 | 0 | 0 | 0 | 0 | 0 | 0 |
| 35 | 0 | 0 | 0 | 0 | 0 | 0 | 0 | 0 |
| 37 | 0 | 0 | 0 | 0 | 0 | 0 | 0 | 0 |
| 40 | 0 | 0 | 0 | 0 | 0 | 0 | 0 | 0 |
| 42 | 0 | 63 | 0 | 0 | 0 | 0 | 0 | 0 |
| 44 | 0 | 63 | 0 | 0 | 0 | 0 | 0 | 0 |
| 47 | 0 | 63 | 0 | 63 | 0 | 0 | 0 | 0 |
| 49 | 0 | 108 | 0 | 108 | 0 | 0 | 0 | 63 |
| 51 | 0 | 108 | 0 | 108 | 0 | 0 | 0 | 75 |
| 54 | 0 | 196 | 0 | 126 | 0 | 0 | 63 | 108 |
| 56 | 0 | 256 | 0 | 172 | 0 | 63 | 63 | 126 |

TABLE 25

GPC3 scFv1-BBz + DN TGF-βRII 1 × 10⁶ cell treatment of Hep3B Tumor Cells

| Days Post Tumor Implant | Tumor volume (mm³) | | | | | | | |
|---|---|---|---|---|---|---|---|---|
| 14 | 196 | 196 | 196 | 172 | 108 | 196 | 108 | 172 |
| 16 | 365 | 288 | 288 | 196 | 126 | 256 | 144 | 288 |
| 19 | 550 | 365 | 405 | 288 | 172 | 405 | 221 | 288 |
| 21 | 726 | 550 | 550 | 550 | 196 | 500 | 320 | 405 |
| 23 | 726 | 726 | 726 | 650 | 288 | 666 | 405 | 600 |
| 26 | 196 | 196 | 288 | 196 | 108 | 196 | 172 | 144 |
| 28 | 108 | 108 | 172 | 108 | 0 | 126 | 75 | 108 |
| 30 | 0 | 63 | 108 | 0 | 0 | 75 | 0 | 63 |
| 33 | 0 | 0 | 63 | 0 | 0 | 0 | 0 | 0 |
| 35 | 0 | 0 | 63 | 0 | 0 | 0 | 0 | 0 |
| 37 | 0 | 0 | 63 | 0 | 0 | 0 | 0 | 0 |
| 40 | 63 | 0 | 108 | 0 | 0 | 0 | 0 | 63 |
| 42 | 108 | 108 | 172 | 0 | 0 | 108 | 0 | 126 |
| 44 | 108 | 126 | 256 | 75 | 0 | 172 | 0 | 172 |

TABLE 25-continued

GPC3 scFv1-BBz + DN TGF-βRII
1 × 10⁶ cell treatment of Hep3B Tumor Cells

| Days Post Tumor Implant | Tumor volume (mm³) | | | | | | | |
|---|---|---|---|---|---|---|---|---|
| 47 | 172 | 144 | 288 | 108 | 0 | 256 | 63 | 256 |
| 49 | 196 | 256 | 405 | 172 | 0 | 288 | 108 | 288 |
| 51 | 256 | 320 | 500 | 172 | 0 | 365 | 108 | 288 |
| 54 | 288 | 446 | 726 | 256 | 0 | 550 | 126 | 405 |
| 56 | 288 | 600 | 864 | 288 | 0 | 666 | 196 | 550 |

Example 11

Using the construct of Example 10, on the last day that all cohorts were intact (Day 33), the significance in anti-tumor efficacy was assessed by One-way ANOVA with Tukey's multiple comparisons test and is included in Table 26. Long-term efficacy and tumor growth delay was determined by progression towards survival to a tumor volume endpoint (FIG. 1, Table 27) set at four-fold the initial volume, with statistical significance determined by the Log-rank (Mantel-Cox) test (Table 28).

TABLE 26

Statistical Significance of Anti-tumor Activity at Day 33

| Tukey's multiple comparisons test | Mean Diff | 95.00% CI of diff. | Significance |
|---|---|---|---|
| Vehicle vs. UT | 90 | −494.6 to 674.6 | ns |
| Vehicle vs. GPC3 CAR 4 × 10⁶ | 2,003 | 1,449 to 2,558 | Yes |
| Vehicle vs. GPC3 CAR 1 × 10⁶ | 1,255 | 700.4 to 1,810 | Yes |
| Vehicle vs. GPC3 CAR + DN TGF-βRII 4 × 10⁶ | 2,011 | 1,456 to 2,566 | Yes |
| Vehicle vs. GPC3 CAR + DN TGF-βRII 1 × 10⁶ | 2,003 | 1,449 to 2,558 | Yes |
| UT vs. GPC3 CAR 4 × 10⁶ | 1,913 | 1,424 to 2,402 | Yes |
| UT vs. GPC3 CAR 1 × 10⁶ | 1,165 | 675.9 to 1,654 | Yes |
| UT vs. GPC3 CAR + DN TGF-βRII 4 × 10⁶ | 1,921 | 1,432 to 2,410 | Yes |
| UT vs. GPC3 CAR + DN TGF-βRII 1 × 10⁶ | 1,913 | 1,424 to 2,402 | Yes |
| GPC3 CAR 4 × 10⁶ vs. GPC3 CAR 1 × 10⁶ | −748.1 | −1,201 to −295.3 | Yes |
| GPC CAR 4 × 10⁶ vs. GPC3 CAR + TGF-βRII 4 × 10⁶ | 7.875 | −444.9 to 460.7 | ns |
| GPC3 CAR 4 × 10⁶ vs. GPC3 CAR + DN TGF-βRII 1 × 10⁶ | 0 | −452.8 to 452.8 | Yes |
| GPC3 CAR 1 × 10⁶ vs. GPC3 CAR + DN TGF-βRII 4 × 10⁶ | 756 | 303.2 to 1,209 | Yes |
| GPC3 CAR 1 × 10⁶ vs. GPC3 CAR + DN TGF-βRII 1 × 10⁶ | 748.1 | 295.3 to 1,201 | Yes |
| GPC3 CAR + DN TGF-βRII 4 × 10⁶ vs. GPC3 CAR + DN TGF-βRII 1 × 10⁶ | −7.875 | −460.7 to 444.9 | ns |

Day 33 tumor volume data from Tables 10-15 was assessed for statistical significance across all groups using analysis of variance with Tukey's post-test crosswise between all groups. Significance (p < 0.05) between comparisons is noted by Yes, with ns noting non-significant comparisons.

TABLE 27

Time for each animal to reach 4-fold the initial tumor volume from start of study. Values reflect day of the study. NR = Not Reached.

| Vehicle | UT | GPC3 CAR 1 × 10⁶ | GPC3 CAR + DN TGF-βRII 1 × 10⁶ | GPC3 CAR 4 × 10⁶ | GPC3 CAR + DN TGF-βRII 4 × 10⁶ |
|---|---|---|---|---|---|
| 23 | 26 | 33 | NR | 51 | NR |
| 23 | 23 | 21 | NR | 54 | NR |
| 21 | 23 | NR | 56 | NR | NR |
| 21 | 26 | 56 | NR | 54 | NR |
| 23 | 37 | NR | 54 | NR | |
| 21 | 30 | NR | NR | NR | |
| 23 | 35 | NR | 56 | NR | |
| 26 | 30 | NR | NR | NR | |

Statistical survival to a tumor endpoint set at 4-fold the initial volume is represented by each animal and the day of study this occurs. Long-term efficacy, defined by failure to reach this endpoint, is depicted by NR (Not Reached).

TABLE 28

Significance of Tumor Growth Delay and Long Term Efficacy

| Log-rank (Mantle-Cox) test | Significance |
|---|---|
| Vehicle vs. UT | ns |
| Vehicle vs. GPC3 CAR 4 × 10⁶ | Yes |
| Vehicle vs. GPC3 CAR 1 × 10⁶ | Yes |
| Vehicle vs. GPC3 CAR + DN TGF-βRII 4 × 10⁶ | Yes |
| Vehicle vs. GPC3 CAR + DN TGF-βRII 1 × 10⁶ | Yes |
| UT vs. GPC3 CAR 4 × 10⁶ | Yes |
| UT vs. GPC3 CAR 1 × 10⁶ | Yes |
| UT vs. GPC3 CAR + DN TGF-βRII 4 × 10⁶ | Yes |
| UT vs. GPC3 CAR + DN TGF-βRII 1 × 10⁶ | Yes |
| GPC3 CAR 4 × 10⁶ vs. GPC3 CAR 1 × 10⁶ | Yes |

TABLE 28-continued

Significance of Tumor Growth Delay and Long Term Efficacy

| Log-rank (Mantle-Cox) test | Significance |
|---|---|
| GPC3 CAR 4 × 10⁶ vs. GPC3 CAR + DN TGF-βRII 4 × 10⁶ | Yes |
| GPC3 CAR 4 × 10⁶ vs. GPC3 CAR + DN TGF-βRII 1 × 10⁶ | Yes |
| GPC3 CAR 1 × 10⁶ vs. GPC3 CAR + DN TGF-βRII 4 × 10⁶ | Yes |
| GPC3 CAR 1 × 10⁶ vs. GPC3 CAR + DN TGF-βRII 1 × 10⁶ | Yes |
| GPC3 CAR + DN TGF-βRII 4 × 10⁶ vs. GPC3 CAR + DN TGF-βRII 1 × 10⁶ | ns |

Survival data from Table 16 was assessed for statistical significance using a Log-rank (Mantle-Cox) pairwise comparison.
Significance (p < 0.05) between comparisons is noted by Yes, with ns noting non-significant comparisons.

At Day 33, GPC3 CARs were effective at controlling tumor volume, with a dose-dependent effect in efficacy as shown in Table 26. At 1×10⁶ CAR, addition of the DN TGF-βRII had a significant impact in tumor efficacy. This effect was not seen at Day 33 with 4×10⁶ dose given the greater efficacy observed with the CAR at this higher dose. However, assessing tumor growth delay to 4-fold the initial tumor volume (Table 27 and Table 28), the addition of the DN TGF-βRII had significant effect in long-term efficacy at both the 1×10⁶ and 4×10⁶ CAR dose.

Example 12

Further experiments were conducted to compare a CAR-DN TGF-βRII construct generated from a codon-optimized sequence with a similar construct generated from a non-codon-optimized sequence. The following CAR-DN TGF-βRII constructs were generated:
  a. Construct CAR DNR A: (a GPC3 scFv+4-1BB intracellular domain+CD3ζ intracellular domain, a T2A self-cleaving motif, and the DN TGF-βRII) as shown in SEQ ID NO: 52.
  b. Construct CAR DNR B: (a GPC3 scFv+4-1BB intracellular domain+CD3ζ intracellular domain as described in Li, *Gastroenterology*, 2020+ WO2019094482A1, a T2A and the DN TGF-βRII) of SEQ ID NO: 55.

```
                                        (SEQ ID NO: 55)
ATGCTTCTCCTGGTGACAAGCCTTCTGCTCTGTGAGTTACCACACCCAGC

ATTCCTCCTGATCCCACATATGGAGGTGCAGCTTGTTGAGTCTGGTGGAG

GATTGGTGCAGCCTGGAGGGTCATTGAGACTCTCATGTGCAGCCTCTGGA

TTCACCTTCAATAAGAATGCCATGAATTGGGTCCGCCAGGCTCCAGGAAA

GGGTTTGGAATGGGTTGGCCGCATAAGAAATAAAACTAATAATTATGCAA

CATATTATGCCGATTCAGTGAAAGCCAGGTTTACCATCTCCAGAGATGAT

TCAAAGAACTCACTCTATCTGCAAATGAACAGCTTGAAAACCGAGGACAC

AGCCGTGTACTATTGTGTGGCTGGTAACTCGTTTGCTTACTGGGGCCAAG

GGACTCTGGTCACTGTCTCTGCAGGCGGAGGCGGATCAGGTGGTGGCGGA

TCTGGAGGTGGCGGAAGCGACATTGTGATGACCCAGTCTCCAGACTCCCT

AGCTGTGTCACTGGGAGAGAGGGCCACTATCAACTGCAAGTCCAGTCAGA

GCCTTTTATATAGCAGCAATCAAAAGAACTACTTGGCCTGGTACCAACAG

AAACCAGGGCAGCCTCCTAAACTGCTGATTTACTGGGCATCCAGTAGGGA

ATCTGGGGTCCCTGATCGCTTCAGTGGCAGTGGATCTGGGACAGATTTCA

CTCTCACCATCAGCAGTCTGCAGGCTGAAGACGTGGCAGTTTATTACTGT

CAGCAATATTATAACTATCCGCTCACGTTCGGTCAGGGGACCAAGTTGGA

GATCAAAACTAGTACCACGACGCCAGCGCCGCGACCACCAACACCGGCGC

CCACCATCGCGTCGCAGCCCCTGTCCCTGCGCCCAGAGGCGTGCCGGCCA

GCGGCGGGGGCGCAGTGCACACGAGGGGGCTGGACTTCGCCTGTGACAT

CTACATCTGGGCGCCCTTGGCCGGGACTTGTGGGGTCCTTCTCCTGTCAC

TGGTTATCACCAAACGGGGCAGAAAGAAACTCCTGTATATATTCAAACAA

CCATTTATGAGACCAGTACAAACTACTCAAGAGGAAGATGGCTGTAGCTG

CCGATTTCCAGAAGAAGAAGAAGGAGGATGTGAACTGAGAGTGAAGTTCA

GCAGGAGCGCAGACGCCCCCGCGTACCAGCAGGGCCAGAACCAGCTCTAT

AACGAGCTCAATCTAGGACGAAGAGAGGAGTACGATGTTTTGGACAAGAG

ACGTGGCCGGGACCCTGAGATGGGGGGAAAGCCGAGAAGGAAGAACCCTC

AGGAAGGCCTGTACAATGAACTGCAGAAAGATAAGATGGCGGAGGCCTAC

AGTGAGATTGGGATGAAAGGCGAGCGCCGGAGGGGCAAGGGGCACGATGG

CCTTTACCAGGGTCTCAGTACAGCCACCAAGGACACCTACGACGCCCTTC

ACATGCAGGCCCTGCCCCCTCGCGAGGGCAGAGGCTCTCTGCTGACCTGC

GGCGACGTGGAAGAGAACCCAGGCCCCATGGGAAGAGGTTTACTGAGAGG

ACTGTGGCCTTTACACATCGTGCTGTGGACTCGTATCGCCAGCACCATCC

CCCCCCATGTCCAAAAGAGCGTGAACAACGACATGATCGTGACCGACAAC

AATGGCGCCGTGAAGTTCCCCCAGCTGTGCAAGTTCTGCGACGTGAGGTT

CAGCACTTGTGACAACCAGAAGAGCTGCATGAGCAACTGCAGCATCACCT

CCATCTGCGAGAAGCCCCAAGAAGTGTGCGTGGCCGTGTGGAGGAAGAAC

GACGAGAACATCACTTTAGAGACAGTGTGCCACGACCCCAAGCTGCCCTA

CCACGACTTCATTTTAGAAGATGCCGCCAGCCCCAAGTGCATCATGAAGG

AGAAGAAGAAGCCCGGCGAGACCTTCTTCATGTGTTCTTGTTCGTCTGAT

GAGTGCAACGATAACATCATCTTCAGCGAGGAGTACAACACCAGCAACCC

CGATTTACTGCTGGTGATCTTCCAAGTTACCGGCATTTCTTTACTGCCTC

CGTTGGGCGTGGCTATCAGCGTGATCATCATCTTCTACTGCTATCGTGTT

AATCGTCAATGA.
```

Similar to the previous experiments, CD3⁺ cells were isolated from primary human peripheral blood mononuclear cells (PBMCs) and transduced with the GPC3 CAR constructs above in the presence of polybrene and at a multiplicity of infection of two based on expression titer in Jurkat cells. At the end of manufacturing, cells were frozen down in Cryostor® CS5 and stored in liquid nitrogen until thawing. Upon thawing, cells were rested in T cell culture medium overnight with 100 UI/mL IL-2, washed, and stained with Live/Dead™ Violet diluted at 1:1000, recombinant human GPC3 (rhGPC3) fluorescently conjugated to DyLight™ 650 diluted at 1:200, anti-TGF-βRII-PE at and anti-CD3 BV650 at 1:100 in PBS for 30 min at 4° C. The DNA pellet of 1×10⁵ cells is extracted in QuickExtract™ Buffer, frozen, and used to measure average vector copy number (VCN) by droplet digital PCR quantifying frequency of integrated virus per cell. Percentage CAR+ cells are defined as percentage of cells staining with rhGPC3 amongst Live/Dead™ negative, CD3+ cells, and Mean Fluorescence Intensity (MFI) of CAR+, and Vector copy number (VCN) are given in the example. Construct CAR DNR A has a higher MFI of CAR+ cells which could indicate more efficient expression or higher affinity of the CAR to rhGPC3.

TABLE 29

CAR DNR A enhanced transduction and expression efficiency

| | Untransduced | CAR DNR A | CAR DNR B |
|---|---|---|---|
| % CAR + (% rhGPC # +) | 0.5 | 86.1 | 61.4 |
| MFI CAR + | 6,178 | 15,857 | 1,407 |
| % TGFβRII + | 6.8 | 57.4 | 46.9 |
| VCN | 1.18 | 0.79 | 0 |

Example 13

CAR+ T cells ($5 \times 10^4$) manufactured, frozen, rested and stained as described previously were co-cultured with HCC target cells ($5 \times 10^4$) for 48 hours to induce cytokine release and supernatants were frozen at −80° C. Interferon gamma (IFNγ) concentrations were measured using Milliplex® Map Human High Sensitivity T cell Panel (Cat #HSTCMAG-28PMX13BK) after diluting the supernatant 500 fold in PBS. The data in Table 30 illustrates that construct CAR DNR A secretes less IFNγ than construct CAR DNR B in the presence of GPC3− cell lines Hep3B GPC3 KO and Sk-Hep1. This data suggests that CAR DNR A has less tonic activation mediated by the CAR than CAR DNR B.

TABLE 30

CAR DNR A decreased cytokine release in GPC3− target cells

| | Hep3B (pg/mL) | | | Hep3B GPC3 KO (pg/mL) | | | SK-HEP-1 (pg/mL) | | |
|---|---|---|---|---|---|---|---|---|---|
| CAR DNR A | 67,053 | 51,967 | 57,358 | 180 | 295 | 133 | 340 | 272 | 272 |
| CAR DNR B | 188,270 | 247,689 | 224,843 | 129,793 | 122,655 | 98,067 | 70,013 | 69,941 | 60,165 |
| Un-transduced | 37 | 86 | 305 | 86 | 37 | 305 | 37 | 11 | 305 |

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A recombinant polypeptide consisting of an extracellular domain (ECD) from a Transforming Growth Factor-beta (TGF-β) receptor, a transmembrane domain (TMD), and an intracellular domain (ICD) consisting of an amino acid sequence having at least 90% sequence identity to SEQ ID NO: 6, wherein the recombinant polypeptide binds to TGF-β1 and functions as a dominant negative inhibitor of TGF-β receptor.

2. The recombinant polypeptide according to claim 1, wherein the ECD is selected from TGF-βRI or TGF-βRII.

3. The recombinant polypeptide according to claim 1, wherein the TMD is selected from the group consisting of Transforming Growth Factor-beta receptor I (TGF-βRI), Transforming Growth Factor-beta receptor II (TGF-βRII), Platelet-derived growth factor receptor (PDGFR), Cluster of differentiation 4 (CD4), Cluster of differentiation 8 (CD8), Cluster of differentiation 28 (CD28), Cluster of differentiation 127 CD127), Cluster of differentiation 132 (CD132), Cluster of differentiation 3-zeta (CD3ζ), Tumor necrosis factor ligand superfamily 9 (4-IBB), Tumor necrosis factor ligand superfamily 4 (OX40), Inducible T-cell costimulatory (ICOS), Cytotoxic T-lymphocyte associated protein 4 (CTLA-4), Programmed cell death protein 1 (PD-1), Lymphocyte activation gene 3 (LAG-3), Natural Killer cell receptor 2B4 (2B4), Interleukin-5 (IL-5), Interleukin-7 (IL-7), Interleukin-7 subunit alpha (IL-7Ra), B- and T-lymphocyte attenuator (BTLA) and mutants thereof.

4. The recombinant polypeptide according to claim 1, wherein the intracellular domain (ICD) lacks amino acid residues responsible for signaling and phosphorylation present in wild-type TGF-β receptor.

5. The recombinant polypeptide according claim 1, wherein the ECD comprises the amino acid sequence having at least 75% sequence identity to SEQ ID NO: 15 and the TMD comprises the amino acid sequence having at least 75% sequence identity to SEQ ID NO: 16.

6. The recombinant polypeptide according to claim 1, wherein the polypeptide consists of the amino acid sequence having at least 75% sequence identity to SEQ ID NO: 14.

7. An expression vector comprising a nucleic acid encoding the polypeptide according to claim 1.

8. The expression vector according to claim 7, further comprising a nucleic acid sequence encoding a chimeric antigen receptor (CAR).

9. The expression vector according to claim 8, wherein the CAR binds to a tumor antigen comprising Cluster of differentiation 19 (CD19), Cluster of differentiation 20 (CD20), Prostate-specific membrane antigen (PSMA), Prostrate-cancer membrane antigen (PCMA), C-type lectin-like molecule 1 (CLL-1), or Glypican 3 (GPC3).

10. The expression vector according to claim 9, wherein the CAR binds to a tumor antigen comprising GPC3.

11. A T cell transduced with the expression vector according to claim 7.

* * * * *

SEQUENCE LISTING

<160> NUMBER OF SEQ ID NOS: 58

<210> SEQ ID NO 1
<211> LENGTH: 1509
<212> TYPE: DNA
<213> ORGANISM: Homo sapiens

<400> SEQUENCE: 1

```
atggaggcgg cggtcgctgc tccgcgtccc cggctgctcc tcctcgtgct ggcggcggcg      60
gcggcggcgg cggcggcgct gctcccgggg gcgacggcgt tacagtgttt ctgccacctc     120
tgtacaaaag acaattttac ttgtgtgaca gatgggctct gctttgtctc tgtcacagag     180
accacagaca aagttataca caacagcatg tgtatagctg aaattgactt aattcctcga     240
gataggccgt ttgtatgtgc accctcttca aaaactgggt ctgtgactac aacatattgc     300
tgcaatcagg accattgcaa taaaatagaa cttccaacta ctgtaaagtc atcacctggc     360
cttggtcctg tggaactggc agctgtcatt gctggaccag tgtgcttcgt ctgcatctca     420
ctcatgttga tggtctatat ctgccacaac cgcactgtca ttcaccatcg agtgccaaat     480
gaagaggacc cttcattaga tcgccctttt atttcagagg tactacgtt  gaaagactta     540 atttatgata tgacaacgtc aggttctggc tcaggtttac cattgcttgt tcagagaaca     600
attgcgagaa ctattgtgtt acaagaaagc attggcaaag gtcgatttgg agaagtttgg     660
```

-continued

```
agaggaaagt ggcggggaga agaagttgct gttaagatat tctcctctag agaagaacgt    720
tcgtggttcc gtgaggcaga gatttatcaa actgtaatgt tacgtcatga aaacatcctg    780
ggatttatag cagcagacaa taaagacaat ggtacttgga ctcagctctg gttggtgtca    840
gattatcatg agcatggatc ccttttgat  tacttaaaca gatacacagt tactgtggaa    900
ggaatgataa aacttgctct gtccacggcg agcggtcttg cccatcttca catggagatt    960
gttggtaccc aaggaaagcc agccattgct catagagatt tgaaatcaaa gaatatcttg   1020
gtaaagaaga atggaacttg ctgtattgca gacttaggac tggcagtaag acatgattca   1080
gccacagata ccattgatat tgctccaaac cacagagtgg aacaaaaag  gtacatggcc   1140 cctgaagttc tcgatgattc cataaatatg aaacattttg aatccttcaa acgtgctgac   1200
atctatgcaa tgggcttagt attctgggaa attgctcgac gatgttccat tggtggaatt   1260
catgaagatt accaactgcc ttattatgat cttgtacctt ctgacccatc agttgaagaa   1320
atgagaaaag ttgtttgtga acagaagtta aggccaaata tcccaaacag atggcagagc   1380
tgtgaagcct tgagagtaat ggctaaaatt atgagagaat gttggtatgc caatggagca   1440
gctaggctta cagcattgcg gattaagaaa acattatcgc aactcagtca acaggaaggc   1500
atcaaaatg                                                           1509
```

<210> SEQ ID NO 2
<211> LENGTH: 503
<212> TYPE: PRT
<213> ORGANISM: Homo sapiens

<400> SEQUENCE: 2

```
Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
    210                 215                 220
```

```
Arg Gly Glu Glu Val Ala Val Lys Ile Phe Ser Ser Arg Glu Arg
225                 230                 235                 240

Ser Trp Phe Arg Glu Ala Glu Ile Tyr Gln Thr Val Met Leu Arg His
            245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
            275                 280                 285

Phe Asp Tyr Leu Asn Arg Tyr Thr Val Thr Val Glu Gly Met Ile Lys
            290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
            325                 330                 335

Lys Asn Ile Leu Val Lys Lys Asn Gly Thr Cys Cys Ile Ala Asp Leu
            340                 345                 350

Gly Leu Ala Val Arg His Asp Ser Ala Thr Asp Thr Ile Asp Ile Ala
            355                 360                 365

Pro Asn His Arg Val Gly Thr Lys Arg Tyr Met Ala Pro Glu Val Leu
            370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
            405                 410                 415

Ile Gly Gly Ile His Glu Asp Tyr Gln Leu Pro Tyr Tyr Asp Leu Val
            420                 425                 430

Pro Ser Asp Pro Ser Val Glu Glu Met Arg Lys Val Val Cys Glu Gln
            435                 440                 445

Lys Leu Arg Pro Asn Ile Pro Asn Arg Trp Gln Ser Cys Glu Ala Leu
            450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
            485                 490                 495

Gln Gln Glu Gly Ile Lys Met
            500

<210> SEQ ID NO 3
<211> LENGTH: 93
<212> TYPE: PRT
<213> ORGANISM: Artificial Sequence
<220> FEATURE:
<223> OTHER INFORMATION: Extracellular Domain

<400> SEQUENCE: 3

Leu Gln Cys Phe Cys His Leu Cys Thr Lys Asp Asn Phe Thr Cys Val
1               5                   10                  15

Thr Asp Gly Leu Cys Phe Val Ser Val Thr Glu Thr Thr Asp Lys Val
            20                  25                  30

Ile His Asn Ser Met Cys Ile Ala Glu Ile Asp Leu Ile Pro Arg Asp
            35                  40                  45

Arg Pro Phe Val Cys Ala Pro Ser Ser Lys Thr Gly Ser Val Thr Thr
            50                  55                  60

Thr Tyr Cys Cys Asn Gln Asp His Cys Asn Lys Ile Glu Leu Pro Thr
65                  70                  75                  80
```

Thr Val Lys Ser Ser Pro Gly Leu Gly Pro Val Glu Leu
            85                  90

<210> SEQ ID NO 4
<211> LENGTH: 21
<212> TYPE: PRT
<213> ORGANISM: Artificial Sequence
<220> FEATURE:
<223> OTHER INFORMATION: Transmembrane Domain

<400> SEQUENCE: 4

Ala Ala Val Ile Ala Gly Pro Val Cys Phe Val Cys Ile Ser Leu Met
1               5                   10                  15

Leu Met Val Tyr Ile
            20

<210> SEQ ID NO 5
<211> LENGTH: 114
<212> TYPE: PRT
<213> ORGANISM: Artificial Sequence
<220> FEATURE:
<223> OTHER INFORMATION: Extracellular Domain + Transmembrane Domain

<400> SEQUENCE: 5

Leu Gln Cys Phe Cys His Leu Cys Thr Lys Asp Asn Phe Thr Cys Val
1               5                   10                  15

Thr Asp Gly Leu Cys Phe Val Ser Val Thr Glu Thr Thr Asp Lys Val
            20                  25                  30

Ile His Asn Ser Met Cys Ile Ala Glu Ile Asp Leu Ile Pro Arg Asp
        35                  40                  45

Arg Pro Phe Val Cys Ala Pro Ser Ser Lys Thr Gly Ser Val Thr Thr
    50                  55                  60

Thr Tyr Cys Cys Asn Gln Asp His Cys Asn Lys Ile Glu Leu Pro Thr
65                  70                  75                  80

Thr Val Lys Ser Ser Pro Gly Leu Gly Pro Val Glu Leu Ala Ala Val
                85                  90                  95

Ile Ala Gly Pro Val Cys Phe Val Cys Ile Ser Leu Met Leu Met Val
            100                 105                 110

Tyr Ile

<210> SEQ ID NO 6
<211> LENGTH: 5
<212> TYPE: PRT
<213> ORGANISM: Artificial Sequence
<220> FEATURE:
<223> OTHER INFORMATION: Intracellular Domain

<400> SEQUENCE: 6

Arg Val Asn Arg Gln
1               5

<210> SEQ ID NO 7
<211> LENGTH: 119
<212> TYPE: PRT
<213> ORGANISM: Artificial Sequence
<220> FEATURE:
<223> OTHER INFORMATION: Extracellular Domain + Transmembrane Domain +
      Intracellular Domain

<400> SEQUENCE: 7

Leu Gln Cys Phe Cys His Leu Cys Thr Lys Asp Asn Phe Thr Cys Val
1               5                   10                  15

```
Thr Asp Gly Leu Cys Phe Val Ser Val Thr Glu Thr Thr Asp Lys Val
            20                  25                  30

Ile His Asn Ser Met Cys Ile Ala Glu Ile Asp Leu Ile Pro Arg Asp
        35                  40                  45

Arg Pro Phe Val Cys Ala Pro Ser Ser Lys Thr Gly Ser Val Thr Thr
    50                  55                  60

Thr Tyr Cys Cys Asn Gln Asp His Cys Asn Lys Ile Glu Leu Pro Thr
65                  70                  75                  80

Thr Val Lys Ser Ser Pro Gly Leu Gly Pro Val Glu Leu Ala Ala Val
                85                  90                  95

Ile Ala Gly Pro Val Cys Phe Val Cys Ile Ser Leu Met Leu Met Val
                100                 105                 110

Tyr Ile Arg Val Asn Arg Gln
            115

<210> SEQ ID NO 8
<211> LENGTH: 33
<212> TYPE: PRT
<213> ORGANISM: Artificial Sequence
<220> FEATURE:
<223> OTHER INFORMATION: Signal

<400> SEQUENCE: 8

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala

<210> SEQ ID NO 9
<211> LENGTH: 126
<212> TYPE: PRT
<213> ORGANISM: Artificial Sequence
<220> FEATURE:
<223> OTHER INFORMATION: Signal + Extracellular Domain

<400> SEQUENCE: 9

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
                100                 105                 110

Thr Thr Val Lys Ser Ser Pro Gly Leu Gly Pro Val Glu Leu
            115                 120                 125

<210> SEQ ID NO 10
<211> LENGTH: 152
<212> TYPE: PRT
<213> ORGANISM: Artificial Sequence
```

```
<220> FEATURE:
<223> OTHER INFORMATION: Signal + Extracellular Domain + Transmembrane
      Domain + Intracellular Domain

<400> SEQUENCE: 10

Met Glu Ala Ala Val Ala Ala Pro Arg Pro Arg Leu Leu Leu Val
1               5                   10                  15

Leu Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
            115                 120                 125

Val Ile Ala Gly Pro Val Cys Phe Val Cys Ile Ser Leu Met Leu Met
130                 135                 140

Val Tyr Ile Arg Val Asn Arg Gln
145                 150

<210> SEQ ID NO 11
<211> LENGTH: 342
<212> TYPE: DNA
<213> ORGANISM: Artificial Sequence
<220> FEATURE:
<223> OTHER INFORMATION: Extracellular Domain + Transmembrane Domain

<400> SEQUENCE: 11
ttacagtgct tctgccattt atgcaccaag acaacttca cttgtgtcac cgatggttta      60
tgcttcgtga gcgtgaccga gaccaccgac aaggtgatcc acaacagcat gtgcatcgcc    120
gagatcgatt taatccctcg tgacagaccc ttcgtgtgcg cccctagcag caagaccggc    180
agcgtgacca ccacctactg ctgcaaccaa gatcactgca acaagatcga gctgcccacc    240
accgtgaaga gcagccccgg tttaggaccc gttgaactgg ctgccgtgat tgccggcccc    300
gtgtgctttg tgtgcatctc tttaatgctg atggtgtaca tt                      342

<210> SEQ ID NO 12
<211> LENGTH: 1701
<212> TYPE: DNA
<213> ORGANISM: Homo sapiens

<400> SEQUENCE: 12
atgggcaggg gcctgctgag gggcctgtgg ccctgcaca tcgtgctgtg gaccaggatc      60
gccagcacca tcccccccca cgtgcagaag agcgtgaaca acgacatgat cgtgaccgac    120
aacaacggcg ccgtgaagtt ccccagctg tgcaagttct gcgacgtgag gttcagcacc    180
tgcgacaacc agaagagctg catgagcaac tgcagcatca ccagcatctg cgagaagccc    240
caggaggtgt gcgtggccgt gtggaggaag aacgacgaga acatcaccct ggagaccgtg    300
tgccacgacc ccaagctgcc ctaccacgac ttcatcctgg aggacgccgc cagccccaag    360
tgcatcatga aggagaagaa gaagcccggc gagaccttct tcatgtgcag ctgcagcagc    420
```

```
gacgagtgca acgacaacat catcttcagc gaggagtaca acaccagcaa ccccgacctg    480
ctgctggtga tcttccaggt gaccggcatc agcctgctgc ccccctggg cgtggccatc     540
agcgtgatca tcatcttcta ctgctacagg gtgaacaggc agcagaagct gagcagcacc    600
tgggagaccg gcaagaccag gaagctgatg gagttcagcg agcactgcgc catcatcctg    660
gaggacgaca ggagcgacat cagcagcacc tgcgccaaca acatcaacca caacaccgag    720
ctgctgccca tcgagctgga caccctggtg gcaagggca ggttcgccga ggtgtacaag     780
gccaagctga agcagaacac cagcgagcag ttcgagaccg tggccgtgaa gatcttcccc    840
tacgaggagt acgccagctg gaagaccgag aaggacatct tcagcgacat caacctgaag    900
cacgagaaca tcctgcagtt cctgaccgcc gaggagagga gaccgagct gggcaagcag     960
tactggctga tcaccgcctt ccacgccaag ggcaacctgc aggagtacct gaccaggcac   1020
gtgatcagct gggaggacct gaggaagctg ggcagcagcc tggccagggg catcgcccac   1080
ctgcacagcg accacacccc ctgcggcagg cccaagatgc ccatcgtgca cagggacctg   1140
aagagcagca acatcctggt gaagaacgac ctgacctgct gcctgtgcga cttcggcctg   1200
agcctgaggc tggaccccac cctgagcgtg acgacctgg ccaacagcgg ccaggtgggc    1260
accgccaggt acatggcccc cgaggtgctg gagagcagga tgaacctgga gaacgtggag   1320
agcttcaagc agaccgacgt gtacagcatg gccctggtgc tgtgggagat gaccagcagg   1380
tgcaacgccg tgggcgaggt gaaggactac gagccccccct tcggcagcaa ggtgagggag   1440
caccccctgcg tggagagcat gaaggacaac gtgctgaggg acaggggcag gcccgagatc   1500
cccagcttct ggctgaacca ccagggcatc cagatggtgt gcgagaccct gaccgagtgc   1560
tgggaccacg accccgaggc caggctgacc gcccagtgcg tggccgagag gttcagcgag   1620
ctggagcacc tggacaggct gagcggcagg agctgcagcg aggagaagat ccccgaggac   1680
ggcagcctga acaccaccaa g                                              1701

<210> SEQ ID NO 13
<211> LENGTH: 567
<212> TYPE: PRT
<213> ORGANISM: Homo sapiens

<400> SEQUENCE: 13

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys
        115                 120                 125

Pro Gly Glu Thr Phe Phe Met Cys Ser Cys Ser Ser Asp Glu Cys Asn
    130                 135                 140
```

```
Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Phe Tyr Cys Tyr Arg Val Asn
            180                 185                 190

Arg Gln Gln Lys Leu Ser Ser Thr Trp Glu Thr Gly Lys Thr Arg Lys
                195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
                355                 360                 365

Gly Arg Pro Lys Met Pro Ile Val His Arg Asp Leu Lys Ser Ser Asn
370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
                420                 425                 430

Arg Met Asn Leu Glu Asn Val Glu Ser Phe Lys Gln Thr Asp Val Tyr
        435                 440                 445

Ser Met Ala Leu Val Leu Trp Glu Met Thr Ser Arg Cys Asn Ala Val
    450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu Glu His Leu
    530                 535                 540

Asp Arg Leu Ser Gly Arg Ser Cys Ser Glu Glu Lys Ile Pro Glu Asp
545                 550                 555                 560
```

Gly Ser Leu Asn Thr Thr Lys
              565

<210> SEQ ID NO 14
<211> LENGTH: 194
<212> TYPE: PRT
<213> ORGANISM: Artificial Sequence
<220> FEATURE:
<223> OTHER INFORMATION: Truncated TGF beta R2

<400> SEQUENCE: 14

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln

<210> SEQ ID NO 15
<211> LENGTH: 137
<212> TYPE: PRT
<213> ORGANISM: Artificial Sequence
<220> FEATURE:
<223> OTHER INFORMATION: Extracellular Domain

<400> SEQUENCE: 15

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
                20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

```
Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp
    130                 135

<210> SEQ ID NO 16
<211> LENGTH: 30
<212> TYPE: PRT
<213> ORGANISM: Artificial Sequence
<220> FEATURE:
<223> OTHER INFORMATION: Transmembrane Domain

<400> SEQUENCE: 16

Leu Leu Leu Val Ile Phe Gln Val Thr Gly Ile Ser Leu Leu Pro Pro
1               5                   10                  15

Leu Gly Val Ala Ile Ser Val Ile Ile Phe Tyr Cys Tyr
            20                  25                  30

<210> SEQ ID NO 17
<211> LENGTH: 167
<212> TYPE: PRT
<213> ORGANISM: Artificial Sequence
<220> FEATURE:
<223> OTHER INFORMATION: Extracellular Domain + Transmembrane Domain

<400> SEQUENCE: 17

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
        50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Leu Leu Leu Val Ile Phe Gln
    130                 135                 140

Val Thr Gly Ile Ser Leu Leu Pro Pro Leu Gly Val Ala Ile Ser Val
145                 150                 155                 160

Ile Ile Ile Phe Tyr Cys Tyr
                165

<210> SEQ ID NO 18
<211> LENGTH: 20
<212> TYPE: PRT
<213> ORGANISM: Artificial Sequence
<220> FEATURE:
<223> OTHER INFORMATION: IL7Ralpha Transmembrane Domain

<400> SEQUENCE: 18

Pro Ile Leu Leu Thr Ile Ser Ile Leu Ser Phe Phe Ser Val Ala Leu
```

```
Leu Val Ile Leu
            20

<210> SEQ ID NO 19
<211> LENGTH: 159
<212> TYPE: PRT
<213> ORGANISM: Artificial Sequence
<220> FEATURE:
<223> OTHER INFORMATION: Extracellular Domain + IL7Ralpha Transmembrane
      Domain

<400> SEQUENCE: 19

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Ser Gly Pro Ile Leu Leu Thr
    130                 135                 140

Ile Ser Ile Leu Ser Phe Phe Ser Val Ala Leu Leu Val Ile Leu
145                 150                 155

<210> SEQ ID NO 20
<211> LENGTH: 23
<212> TYPE: PRT
<213> ORGANISM: Artificial Sequence
<220> FEATURE:
<223> OTHER INFORMATION: IL7Ralpha "CPT" Transmembrane Domain

<400> SEQUENCE: 20

Pro Ile Leu Leu Thr Cys Pro Thr Ile Ser Ile Leu Ser Phe Phe Ser
1               5                   10                  15

Val Ala Leu Leu Val Ile Leu
            20

<210> SEQ ID NO 21
<211> LENGTH: 162
<212> TYPE: PRT
<213> ORGANISM: Artificial Sequence
<220> FEATURE:
<223> OTHER INFORMATION: Extracellular Domain + IL7Ralpha "CPT"

<400> SEQUENCE: 21

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
```

```
                    35                  40                  45
Cys Ser Ile Thr Ser Ile Cys Glu Lys Pro Gln Glu Val Cys Val Ala
 50                  55                  60

Val Trp Arg Lys Asn Asp Glu Asn Ile Thr Leu Glu Thr Val Cys His
 65                  70                  75                  80

Asp Pro Lys Leu Pro Tyr His Asp Phe Ile Leu Glu Asp Ala Ala Ser
                     85                  90                  95

Pro Lys Cys Ile Met Lys Glu Lys Lys Pro Gly Glu Thr Phe Phe
                100                 105                 110

Met Cys Ser Cys Ser Ser Asp Glu Cys Asn Asp Asn Ile Ile Phe Ser
                115                 120                 125

Glu Glu Tyr Asn Thr Ser Asn Pro Asp Ser Gly Pro Ile Leu Leu Thr
                130                 135                 140

Cys Pro Thr Ile Ser Ile Leu Ser Phe Phe Ser Val Ala Leu Leu Val
145                 150                 155                 160

Ile Leu

<210> SEQ ID NO 22
<211> LENGTH: 200
<212> TYPE: PRT
<213> ORGANISM: Artificial Sequence
<220> FEATURE:
<223> OTHER INFORMATION: IL7Ralpha Intracellular Domain

<400> SEQUENCE: 22

Ala Cys Val Leu Trp Lys Lys Arg Ile Lys Pro Ile Val Trp Pro Ser
 1               5                  10                  15

Leu Pro Asp His Lys Lys Thr Leu Glu His Leu Cys Lys Lys Pro Arg
                20                  25                  30

Lys Asn Leu Asn Val Ser Phe Asn Pro Glu Ser Phe Leu Asp Cys Gln
                35                  40                  45

Ile His Arg Val Asp Asp Ile Gln Ala Arg Asp Glu Val Glu Gly Phe
 50                  55                  60

Leu Gln Asp Thr Phe Pro Gln Gln Leu Glu Glu Ser Glu Lys Gln Arg
 65                  70                  75                  80

Leu Gly Gly Asp Val Gln Ser Pro Asn Cys Pro Ser Glu Asp Val Val
                85                  90                  95

Ile Thr Pro Glu Ser Phe Gly Arg Asp Ser Ser Leu Thr Cys Leu Ala
                100                 105                 110

Gly Asn Val Ser Ala Cys Asp Ala Pro Ile Leu Ser Ser Ser Arg Ser
                115                 120                 125

Leu Asp Cys Arg Glu Ser Gly Lys Asn Gly Pro His Val Tyr Gln Asp
                130                 135                 140

Leu Leu Leu Ser Leu Gly Thr Thr Asn Ser Thr Leu Pro Pro Pro Phe
145                 150                 155                 160

Ser Leu Gln Ser Gly Ile Leu Thr Leu Asn Pro Val Ala Gln Gly Gln
                165                 170                 175

Pro Ile Leu Thr Ser Leu Gly Ser Asn Gln Glu Glu Ala Tyr Val Thr
                180                 185                 190

Met Ser Ser Phe Tyr Gln Asn Gln
                195                 200

<210> SEQ ID NO 23
<211> LENGTH: 359
<212> TYPE: PRT
<213> ORGANISM: Artificial Sequence
```

<220> FEATURE:
<223> OTHER INFORMATION: Extracellular Domain + IL7Ralpha +
      Transmembrane Domain + IL7Ralpha ICD

<400> SEQUENCE: 23

```
Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Ser Gly Pro Ile Leu Leu Thr
    130                 135                 140

Ile Ser Ile Leu Ser Phe Phe Ser Val Ala Leu Leu Val Ile Leu Ala
145                 150                 155                 160

Cys Val Leu Trp Lys Lys Arg Ile Lys Pro Ile Val Trp Pro Ser Leu
                165                 170                 175

Pro Asp His Lys Lys Thr Leu Glu His Leu Cys Lys Lys Pro Arg Lys
            180                 185                 190

Asn Leu Asn Val Ser Phe Asn Pro Glu Ser Phe Leu Asp Cys Gln Ile
        195                 200                 205

His Arg Val Asp Asp Ile Gln Ala Arg Asp Glu Val Glu Gly Phe Leu
    210                 215                 220

Gln Asp Thr Phe Pro Gln Gln Leu Glu Glu Ser Glu Lys Gln Arg Leu
225                 230                 235                 240

Gly Gly Asp Val Gln Ser Pro Asn Cys Pro Ser Glu Asp Val Val Ile
                245                 250                 255

Thr Pro Glu Ser Phe Gly Arg Asp Ser Ser Leu Thr Cys Leu Ala Gly
            260                 265                 270

Asn Val Ser Ala Cys Asp Ala Pro Ile Leu Ser Ser Ser Arg Ser Leu
        275                 280                 285

Asp Cys Arg Glu Ser Gly Lys Asn Gly Pro His Val Tyr Gln Asp Leu
    290                 295                 300

Leu Leu Ser Leu Gly Thr Thr Asn Ser Thr Leu Pro Pro Pro Phe Ser
305                 310                 315                 320

Leu Gln Ser Gly Ile Leu Thr Leu Asn Pro Val Ala Gln Gly Gln Pro
                325                 330                 335

Ile Leu Thr Ser Leu Gly Ser Asn Gln Glu Glu Ala Tyr Val Thr Met
            340                 345                 350

Ser Ser Phe Tyr Gln Asn Gln
                355
```

<210> SEQ ID NO 24
<211> LENGTH: 362
<212> TYPE: PRT

```
<213> ORGANISM: Artificial Sequence
<220> FEATURE:
<223> OTHER INFORMATION: Extracellular Domain + IL7Ralpha "CPT"
      Transmembrane Domain + IL7Ralpha Intracellular Domain

<400> SEQUENCE: 24

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
                20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Ser Gly Pro Ile Leu Leu Thr
130                 135                 140

Cys Pro Thr Ile Ser Ile Leu Ser Phe Phe Ser Val Ala Leu Leu Val
145                 150                 155                 160

Ile Leu Ala Cys Val Leu Trp Lys Lys Arg Ile Lys Pro Ile Val Trp
                165                 170                 175

Pro Ser Leu Pro Asp His Lys Lys Thr Leu Glu His Leu Cys Lys Lys
                180                 185                 190

Pro Arg Lys Asn Leu Asn Val Ser Phe Asn Pro Glu Ser Phe Leu Asp
            195                 200                 205

Cys Gln Ile His Arg Val Asp Asp Ile Gln Ala Arg Asp Glu Val Glu
    210                 215                 220

Gly Phe Leu Gln Asp Thr Phe Pro Gln Gln Leu Glu Glu Ser Glu Lys
225                 230                 235                 240

Gln Arg Leu Gly Gly Asp Val Gln Ser Pro Asn Cys Pro Ser Glu Asp
                245                 250                 255

Val Val Ile Thr Pro Glu Ser Phe Gly Arg Asp Ser Ser Leu Thr Cys
                260                 265                 270

Leu Ala Gly Asn Val Ser Ala Cys Asp Ala Pro Ile Leu Ser Ser Ser
            275                 280                 285

Arg Ser Leu Asp Cys Arg Glu Ser Gly Lys Asn Gly Pro His Val Tyr
    290                 295                 300

Gln Asp Leu Leu Leu Ser Leu Gly Thr Thr Asn Ser Thr Leu Pro Pro
305                 310                 315                 320

Pro Phe Ser Leu Gln Ser Gly Ile Leu Thr Leu Asn Pro Val Ala Gln
                325                 330                 335

Gly Gln Pro Ile Leu Thr Ser Leu Gly Ser Asn Gln Glu Glu Ala Tyr
                340                 345                 350

Val Thr Met Ser Ser Phe Tyr Gln Asn Gln
                355                 360

<210> SEQ ID NO 25
<211> LENGTH: 22
```

```
<212> TYPE: PRT
<213> ORGANISM: Artificial Sequence
<220> FEATURE:
<223> OTHER INFORMATION: TGF beta R2 signal sequence

<400> SEQUENCE: 25

Met Gly Arg Gly Leu Leu Arg Gly Leu Trp Pro Leu His Ile Val Leu
1               5                   10                  15

Trp Thr Arg Ile Ala Ser
            20

<210> SEQ ID NO 26
<211> LENGTH: 22
<212> TYPE: PRT
<213> ORGANISM: Artificial Sequence
<220> FEATURE:
<223> OTHER INFORMATION: CSF2Ralpha signal sequence

<400> SEQUENCE: 26

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 27
<211> LENGTH: 32
<212> TYPE: PRT
<213> ORGANISM: Artificial Sequence
<220> FEATURE:
<223> OTHER INFORMATION: CSF2Ralpha signal + Myc tag

<400> SEQUENCE: 27

Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

<210> SEQ ID NO 28
<211> LENGTH: 159
<212> TYPE: PRT
<213> ORGANISM: Artificial Sequence
<220> FEATURE:
<223> OTHER INFORMATION: CSF2Ralpha signal + Extracellular Domain

<400> SEQUENCE: 28

Met Leu Leu Leu Val Thr Ser Leu Leu Leu Cys Glu Leu Pro His Pro
1               5                   10                  15

Ala Phe Leu Leu Ile Pro Thr Ile Pro Pro His Val Gln Lys Ser Val
            20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
            115                 120                 125
```

Pro Gly Glu Thr Phe Phe Met Cys Ser Cys Ser Ser Asp Glu Cys Asn
            130                 135                 140

Asp Asn Ile Ile Phe Ser Glu Glu Tyr Asn Thr Ser Asn Pro Asp
145                 150                 155

<210> SEQ ID NO 29
<211> LENGTH: 169
<212> TYPE: PRT
<213> ORGANISM: Artificial Sequence
<220> FEATURE:
<223> OTHER INFORMATION: CSF2Ralpha + Myc tag + Extracellular Domain

<400> SEQUENCE: 29

Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

Thr Ile Pro Pro His Val Gln Lys Ser Val Asn Asn Asp Met Ile Val
        35                  40                  45

Thr Asp Asn Asn Gly Ala Val Lys Phe Pro Gln Leu Cys Lys Phe Cys
50                  55                  60

Asp Val Arg Phe Ser Thr Cys Asp Asn Gln Lys Ser Cys Met Ser Asn
65                  70                  75                  80

Cys Ser Ile Thr Ser Ile Cys Glu Lys Pro Gln Glu Val Cys Val Ala
                85                  90                  95

Val Trp Arg Lys Asn Asp Glu Asn Ile Thr Leu Glu Thr Val Cys His
            100                 105                 110

Asp Pro Lys Leu Pro Tyr His Asp Phe Ile Leu Glu Asp Ala Ala Ser
        115                 120                 125

Pro Lys Cys Ile Met Lys Glu Lys Lys Pro Gly Glu Thr Phe Phe
    130                 135                 140

Met Cys Ser Cys Ser Ser Asp Glu Cys Asn Asp Asn Ile Ile Phe Ser
145                 150                 155                 160

Glu Glu Tyr Asn Thr Ser Asn Pro Asp
                165

<210> SEQ ID NO 30
<211> LENGTH: 381
<212> TYPE: PRT
<213> ORGANISM: Artificial Sequence
<220> FEATURE:
<223> OTHER INFORMATION: CSF2Ralpha + Extracellular Domain + IL7Ralpha
      Transmembrane Domain + IL7Ralpha Intracellular Domain

<400> SEQUENCE: 30

Met Leu Leu Leu Val Thr Ser Leu Leu Leu Cys Glu Leu Pro His Pro
1               5                   10                  15

Ala Phe Leu Leu Ile Pro Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile

```
            100                 105                 110
Leu Glu Asp Ala Ala Ser Pro Lys Cys Ile Met Lys Glu Lys Lys
            115                 120                 125

Pro Gly Glu Thr Phe Phe Met Cys Ser Cys Ser Ser Asp Glu Cys Asn
            130                 135                 140

Asp Asn Ile Ile Phe Ser Glu Glu Tyr Asn Thr Ser Asn Pro Asp Ser
145                 150                 155                 160

Gly Pro Ile Leu Leu Thr Ile Ser Ile Leu Ser Phe Phe Ser Val Ala
                165                 170                 175

Leu Leu Val Ile Leu Ala Cys Val Leu Trp Lys Lys Arg Ile Lys Pro
            180                 185                 190

Ile Val Trp Pro Ser Leu Pro Asp His Lys Lys Thr Leu Glu His Leu
            195                 200                 205

Cys Lys Lys Pro Arg Lys Asn Leu Asn Val Ser Phe Asn Pro Glu Ser
            210                 215                 220

Phe Leu Asp Cys Gln Ile His Arg Val Asp Asp Ile Gln Ala Arg Asp
225                 230                 235                 240

Glu Val Glu Gly Phe Leu Gln Asp Thr Phe Pro Gln Gln Leu Glu Glu
                245                 250                 255

Ser Glu Lys Gln Arg Leu Gly Gly Asp Val Gln Ser Pro Asn Cys Pro
            260                 265                 270

Ser Glu Asp Val Val Ile Thr Pro Glu Ser Phe Gly Arg Asp Ser Ser
            275                 280                 285

Leu Thr Cys Leu Ala Gly Asn Val Ser Ala Cys Asp Ala Pro Ile Leu
            290                 295                 300

Ser Ser Ser Arg Ser Leu Asp Cys Arg Glu Ser Gly Lys Asn Gly Pro
305                 310                 315                 320

His Val Tyr Gln Asp Leu Leu Leu Ser Leu Gly Thr Thr Asn Ser Thr
                325                 330                 335

Leu Pro Pro Pro Phe Ser Leu Gln Ser Gly Ile Leu Thr Leu Asn Pro
            340                 345                 350

Val Ala Gln Gly Gln Pro Ile Leu Thr Ser Leu Gly Ser Asn Gln Glu
            355                 360                 365

Glu Ala Tyr Val Thr Met Ser Ser Phe Tyr Gln Asn Gln
            370                 375                 380

<210> SEQ ID NO 31
<211> LENGTH: 391
<212> TYPE: PRT
<213> ORGANISM: Artificial Sequence
<220> FEATURE:
<223> OTHER INFORMATION: CSF2Ralpha signal + Myc tag + Extracellular
      Domain + IL7Ralpha Transmembrane Domain + IL7Ralpha Intracellular
      Domain

<400> SEQUENCE: 31

Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

Thr Ile Pro Pro His Val Gln Lys Ser Val Asn Asn Asp Met Ile Val
            35                  40                  45

Thr Asp Asn Asn Gly Ala Val Lys Phe Pro Gln Leu Cys Lys Phe Cys
50                  55                  60

Asp Val Arg Phe Ser Thr Cys Asp Asn Gln Lys Ser Cys Met Ser Asn
65                  70                  75                  80
```

-continued

```
Cys Ser Ile Thr Ser Ile Cys Glu Lys Pro Gln Val Cys Val Ala
                 85                  90                  95

Val Trp Arg Lys Asn Asp Glu Asn Ile Thr Leu Glu Thr Val Cys His
                100                 105                 110

Asp Pro Lys Leu Pro Tyr His Asp Phe Ile Leu Glu Asp Ala Ala Ser
                115                 120                 125

Pro Lys Cys Ile Met Lys Glu Lys Lys Pro Gly Glu Thr Phe Phe
            130                 135                 140

Met Cys Ser Cys Ser Ser Asp Glu Cys Asn Asp Asn Ile Ile Phe Ser
145                 150                 155                 160

Glu Glu Tyr Asn Thr Ser Asn Pro Asp Ser Gly Pro Ile Leu Leu Thr
                165                 170                 175

Ile Ser Ile Leu Ser Phe Phe Ser Val Ala Leu Leu Val Ile Leu Ala
                180                 185                 190

Cys Val Leu Trp Lys Lys Arg Ile Lys Pro Ile Val Trp Pro Ser Leu
            195                 200                 205

Pro Asp His Lys Lys Thr Leu Glu His Leu Cys Lys Lys Pro Arg Lys
            210                 215                 220

Asn Leu Asn Val Ser Phe Asn Pro Glu Ser Phe Leu Asp Cys Gln Ile
225                 230                 235                 240

His Arg Val Asp Asp Ile Gln Ala Arg Asp Glu Val Glu Gly Phe Leu
                245                 250                 255

Gln Asp Thr Phe Pro Gln Gln Leu Glu Glu Ser Glu Lys Gln Arg Leu
            260                 265                 270

Gly Gly Asp Val Gln Ser Pro Asn Cys Pro Ser Glu Asp Val Val Ile
                275                 280                 285

Thr Pro Glu Ser Phe Gly Arg Asp Ser Ser Leu Thr Cys Leu Ala Gly
            290                 295                 300

Asn Val Ser Ala Cys Asp Ala Pro Ile Leu Ser Ser Ser Arg Ser Leu
305                 310                 315                 320

Asp Cys Arg Glu Ser Gly Lys Asn Gly Pro His Val Tyr Gln Asp Leu
                325                 330                 335

Leu Leu Ser Leu Gly Thr Thr Asn Ser Thr Leu Pro Pro Pro Phe Ser
            340                 345                 350

Leu Gln Ser Gly Ile Leu Thr Leu Asn Pro Val Ala Gln Gly Gln Pro
            355                 360                 365

Ile Leu Thr Ser Leu Gly Ser Asn Gln Glu Glu Ala Tyr Val Thr Met
            370                 375                 380

Ser Ser Phe Tyr Gln Asn Gln
385                 390
```

<210> SEQ ID NO 32
<211> LENGTH: 381
<212> TYPE: PRT
<213> ORGANISM: Artificial Sequence
<220> FEATURE:
<223> OTHER INFORMATION: CSF2Ralpha + Extracellular Domain + IL7Ralpha
      Transmembrane Domain + IL7Ralpha Intracellular Domain

<400> SEQUENCE: 32

```
Met Leu Leu Leu Val Thr Ser Leu Leu Leu Cys Glu Leu Pro His Pro
1               5                   10                  15

Ala Phe Leu Leu Ile Pro Thr Ile Pro Pro His Val Gln Lys Ser Val
                20                  25                  30

Asn Asn Asp Met Ile Val Thr Asp Asn Asn Gly Ala Val Lys Phe Pro
```

```
                35                  40                  45
Gln Leu Cys Lys Phe Cys Asp Val Arg Phe Ser Thr Cys Asp Asn Gln
 50                  55                  60
Lys Ser Cys Met Ser Asn Cys Ser Ile Thr Ser Ile Cys Glu Lys Pro
 65                  70                  75                  80
Gln Glu Val Cys Val Ala Val Trp Arg Lys Asn Asp Glu Asn Ile Thr
                 85                  90                  95
Leu Glu Thr Val Cys His Asp Pro Lys Leu Pro Tyr His Asp Phe Ile
                100                 105                 110
Leu Glu Asp Ala Ala Ser Pro Lys Cys Ile Met Lys Glu Lys Lys
                115                 120                 125
Pro Gly Glu Thr Phe Phe Met Cys Ser Cys Ser Ser Asp Glu Cys Asn
130                 135                 140
Asp Asn Ile Ile Phe Ser Glu Glu Tyr Asn Thr Ser Asn Pro Asp Ser
145                 150                 155                 160
Gly Pro Ile Leu Leu Thr Ile Ser Ile Leu Ser Phe Phe Ser Val Ala
                165                 170                 175
Leu Leu Val Ile Leu Ala Cys Val Leu Trp Lys Lys Arg Ile Lys Pro
                180                 185                 190
Ile Val Trp Pro Ser Leu Pro Asp His Lys Lys Thr Leu Glu His Leu
                195                 200                 205
Cys Lys Lys Pro Arg Lys Asn Leu Asn Val Ser Phe Asn Pro Glu Ser
210                 215                 220
Phe Leu Asp Cys Gln Ile His Arg Val Asp Asp Ile Gln Ala Arg Asp
225                 230                 235                 240
Glu Val Glu Gly Phe Leu Gln Asp Thr Phe Pro Gln Gln Leu Glu Glu
                245                 250                 255
Ser Glu Lys Gln Arg Leu Gly Gly Asp Val Gln Ser Pro Asn Cys Pro
                260                 265                 270
Ser Glu Asp Val Val Ile Thr Pro Glu Ser Phe Gly Arg Asp Ser Ser
                275                 280                 285
Leu Thr Cys Leu Ala Gly Asn Val Ser Ala Cys Asp Ala Pro Ile Leu
                290                 295                 300
Ser Ser Ser Arg Ser Leu Asp Cys Arg Glu Ser Gly Lys Asn Gly Pro
305                 310                 315                 320
His Val Tyr Gln Asp Leu Leu Leu Ser Leu Gly Thr Thr Asn Ser Thr
                325                 330                 335
Leu Pro Pro Pro Phe Ser Leu Gln Ser Gly Ile Leu Thr Leu Asn Pro
                340                 345                 350
Val Ala Gln Gly Gln Pro Ile Leu Thr Ser Leu Gly Ser Asn Gln Glu
                355                 360                 365
Glu Ala Tyr Val Thr Met Ser Ser Phe Tyr Gln Asn Gln
                370                 375                 380

<210> SEQ ID NO 33
<211> LENGTH: 394
<212> TYPE: PRT
<213> ORGANISM: Artificial Sequence
<220> FEATURE:
<223> OTHER INFORMATION: CSF2Ralpha signal + Myc tag + Extracellular
      Domain + IL7Ralpha "CPT" Transmembrane Domain + IL7Ralpha
      Intracellular Domain

<400> SEQUENCE: 33

Met Leu Leu Leu Val Thr Ser Leu Leu Leu Cys Glu Leu Pro His Pro
 1               5                  10                  15
```

Ala Phe Leu Leu Ile Pro Glu Gln Lys Leu Ile Ser Glu Glu Asp Leu
            20                  25                  30

Thr Ile Pro Pro His Val Gln Lys Ser Val Asn Asn Asp Met Ile Val
        35                  40                  45

Thr Asp Asn Asn Gly Ala Val Lys Phe Pro Gln Leu Cys Lys Phe Cys
50                  55                  60

Asp Val Arg Phe Ser Thr Cys Asp Asn Gln Lys Ser Cys Met Ser Asn
65                  70                  75                  80

Cys Ser Ile Thr Ser Ile Cys Glu Lys Pro Gln Glu Val Cys Val Ala
                85                  90                  95

Val Trp Arg Lys Asn Asp Glu Asn Ile Thr Leu Glu Thr Val Cys His
            100                 105                 110

Asp Pro Lys Leu Pro Tyr His Asp Phe Ile Leu Glu Asp Ala Ala Ser
        115                 120                 125

Pro Lys Cys Ile Met Lys Glu Lys Lys Pro Gly Glu Thr Phe Phe
130                 135                 140

Met Cys Ser Cys Ser Ser Asp Glu Cys Asn Asp Asn Ile Ile Phe Ser
145                 150                 155                 160

Glu Glu Tyr Asn Thr Ser Asn Pro Asp Ser Gly Pro Ile Leu Leu Thr
                165                 170                 175

Cys Pro Thr Ile Ser Ile Leu Ser Phe Phe Ser Val Ala Leu Leu Val
            180                 185                 190

Ile Leu Ala Cys Val Leu Trp Lys Lys Arg Ile Lys Pro Ile Val Trp
        195                 200                 205

Pro Ser Leu Pro Asp His Lys Lys Thr Leu Glu His Leu Cys Lys Lys
210                 215                 220

Pro Arg Lys Asn Leu Asn Val Ser Phe Asn Pro Glu Ser Phe Leu Asp
225                 230                 235                 240

Cys Gln Ile His Arg Val Asp Asp Ile Gln Ala Arg Asp Glu Val Glu
                245                 250                 255

Gly Phe Leu Gln Asp Thr Phe Pro Gln Gln Leu Glu Glu Ser Glu Lys
            260                 265                 270

Gln Arg Leu Gly Gly Asp Val Gln Ser Pro Asn Cys Pro Ser Glu Asp
        275                 280                 285

Val Val Ile Thr Pro Glu Ser Phe Gly Arg Asp Ser Ser Leu Thr Cys
290                 295                 300

Leu Ala Gly Asn Val Ser Ala Cys Asp Ala Pro Ile Leu Ser Ser Ser
305                 310                 315                 320

Arg Ser Leu Asp Cys Arg Glu Ser Gly Lys Asn Gly Pro His Val Tyr
                325                 330                 335

Gln Asp Leu Leu Leu Ser Leu Gly Thr Thr Asn Ser Thr Leu Pro Pro
            340                 345                 350

Pro Phe Ser Leu Gln Ser Gly Ile Leu Thr Leu Asn Pro Val Ala Gln
        355                 360                 365

Gly Gln Pro Ile Leu Thr Ser Leu Gly Ser Asn Gln Glu Glu Ala Tyr
370                 375                 380

Val Thr Met Ser Ser Phe Tyr Gln Asn Gln
385                 390

<210> SEQ ID NO 34
<211> LENGTH: 384
<212> TYPE: PRT
<213> ORGANISM: Artificial Sequence
<220> FEATURE:

<223> OTHER INFORMATION: CSF2Ralpha signal + Extracellular Domain + IL7Ralpha "CPT" Transmembrane Domain + IL7Ralpha Intracellular Domain

<400> SEQUENCE: 34

Met Leu Leu Leu Val Thr Ser Leu Leu Cys Glu Leu Pro His Pro
1               5

<210> SEQ ID NO 35
<211> LENGTH: 573
<212> TYPE: DNA
<213> ORGANISM: Artificial Sequence
<220> FEATURE:
<223> OTHER INFORMATION: CSF2Ralpha signal + Myc tag + Extracellular Domain + IL7Ralpha Transmembrane Domain

<400> SEQUENCE: 35

```
atgctgctgc tggtgaccag cctgctgctg tgcgagctgc ccacccgc cttcctgctg      60
atccccgagc agaagctgat cagcgaggag gacctgacca tccccccca cgtgcagaag     120
agcgtgaaca cgacatgat cgtgaccgac aacaacggcg ccgtgaagtt ccccagctg     180
tgcaagttct gcgacgtgag gttcagcacc tgcgacaacc agaagagctg catgagcaac    240
tgcagcatca ccagcatctg cgagaagccc caggaggtgt gcgtggccgt gtggaggaag    300
aacgacgaga acatcaccct ggagaccgtg tgccacgacc ccaagctgcc ctaccacgac    360
ttcatcctgg aggacgccgc cagccccaag tgcatcatga ggagaagaa gaagcccggc    420
gagaccttct tcatgtgcag ctgcagcagc gacgagtgca cgacaacat catcttcagc    480
gaggagtaca caccagcaa ccccgacccc agccccatcc tgctgaccat cagcatcctg    540
agcttcttca gcgtggccct gctggtgatc ctg                                573
```

<210> SEQ ID NO 36
<211> LENGTH: 582
<212> TYPE: DNA
<213> ORGANISM: Artificial Sequence
<220> FEATURE:
<223> OTHER INFORMATION: CSF2Ralpha signal + Myc tag + Extracellular Domain + IL7Ralpha "CPT" Transmembrane Domain

<400> SEQUENCE: 36

```
atgctgctgc tggtgaccag cctgctgctg tgcgagctgc ccacccgc cttcctgctg      60
atccccgagc agaagctgat cagcgaggag gacctgacca tccccccca cgtgcagaag     120
agcgtgaaca cgacatgat cgtgaccgac aacaacggcg ccgtgaagtt ccccagctg     180
tgcaagttct gcgacgtgag gttcagcacc tgcgacaacc agaagagctg catgagcaac    240
tgcagcatca ccagcatctg cgagaagccc caggaggtgt gcgtggccgt gtggaggaag    300
aacgacgaga acatcaccct ggagaccgtg tgccacgacc ccaagctgcc ctaccacgac    360
ttcatcctgg aggacgccgc cagccccaag tgcatcatga ggagaagaa gaagcccggc    420
gagaccttct tcatgtgcag ctgcagcagc gacgagtgca cgacaacat catcttcagc    480
gaggagtaca caccagcaa ccccgacccc agcggcatcc tgctgacctg ccccaccatc    540
agcatcctga gcttcttcag cgtggccctg ctggtgatcc tg                      582
```

<210> SEQ ID NO 37
<211> LENGTH: 473
<212> TYPE: PRT
<213> ORGANISM: Artificial Sequence
<220> FEATURE:
<223> OTHER INFORMATION: Artificial Sequence

<400> SEQUENCE: 37

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45
```

```
Pro Pro Lys Leu Leu Ile Tyr Trp Ala Ser Ser Arg Glu Ser Gly Val
 50                  55                  60
Pro Asp Arg Phe Ser Gly Ser Gly Ser Gly Thr Asp Phe Thr Leu Thr
 65                      70                  75                  80
Ile Ser Ser Leu Gln Ala Glu Asp Val Ala Val Tyr Tyr Cys Gln Gln
                 85                  90                  95
Tyr Tyr Asn Tyr Pro Leu Thr Phe Gly Gln Gly Thr Lys Leu Glu Ile
             100                 105                 110
Lys Gly Ser Thr Ser Gly Ser Gly Lys Pro Gly Ser Gly Glu Gly Ser
             115                 120                 125
Thr Lys Gly Glu Val Gln Leu Val Glu Ser Gly Gly Gly Leu Val Gln
130                 135                 140
Pro Gly Gly Ser Leu Arg Leu Ser Cys Ala Ala Ser Gly Phe Thr Phe
145                 150                 155                 160
Asn Lys Asn Ala Met Asn Trp Val Arg Gln Ala Pro Gly Lys Gly Leu
                 165                 170                 175
Glu Trp Val Gly Arg Ile Arg Asn Lys Thr Asn Asn Tyr Ala Thr Tyr
             180                 185                 190
Tyr Ala Asp Ser Val Lys Ala Arg Phe Thr Ile Ser Arg Asp Asp Ser
             195                 200                 205
Lys Asn Ser Leu Tyr Leu Gln Met Asn Ser Leu Lys Thr Glu Asp Thr
210                 215                 220
Ala Val Tyr Tyr Cys Val Ala Gly Asn Ser Phe Ala Tyr Trp Gly Gln
225                 230                 235                 240
Gly Thr Leu Val Thr Val Ser Ser Gly Ser Thr Thr Thr Pro Ala Pro
                 245                 250                 255
Arg Pro Pro Thr Pro Ala Pro Thr Ile Ala Ser Gln Pro Leu Ser Leu
             260                 265                 270
Arg Pro Glu Ala Cys Arg Pro Ala Ala Gly Gly Ala Val His Thr Arg
             275                 280                 285
Gly Leu Asp Phe Ala Cys Asp Ile Tyr Ile Trp Ala Pro Leu Ala Gly
290                 295                 300
Thr Cys Gly Val Leu Leu Leu Ser Leu Val Ile Thr Leu Tyr Cys Lys
305                 310                 315                 320
Arg Gly Arg Lys Lys Leu Leu Tyr Ile Phe Lys Gln Pro Phe Met Arg
                 325                 330                 335
Pro Val Gln Thr Thr Gln Glu Glu Asp Gly Cys Ser Cys Arg Phe Pro
             340                 345                 350
Glu Glu Glu Glu Gly Gly Cys Glu Leu Arg Val Lys Phe Ser Arg Ser
             355                 360                 365
Ala Asp Ala Pro Ala Tyr Gln Gln Gly Gln Asn Gln Leu Tyr Asn Glu
370                 375                 380
Leu Asn Leu Gly Arg Arg Glu Glu Tyr Asp Val Leu Asp Lys Arg Arg
385                 390                 395                 400
Gly Arg Asp Pro Glu Met Gly Gly Lys Pro Arg Arg Lys Asn Pro Gln
                 405                 410                 415
Glu Gly Leu Tyr Asn Glu Leu Gln Lys Asp Lys Met Ala Glu Ala Tyr
             420                 425                 430
Ser Glu Ile Gly Met Lys Gly Glu Arg Arg Arg Gly Lys Gly His Asp
             435                 440                 445
Gly Leu Tyr Gln Gly Leu Ser Thr Ala Thr Lys Asp Thr Tyr Asp Ala
450                 455                 460
```

```
Leu His Met Gln Ala Leu Pro Pro Arg
465                 470
```

<210> SEQ ID NO 38
<211> LENGTH: 117
<212> TYPE: PRT
<213> ORGANISM: Artificial Sequence
<220> FEATURE:
<223> OTHER INFORMATION: Artificial Sequence

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Lys Asn
            20                  25                  30

Ala Met Asn Trp Val Arg Gln Ala Pro Gly Lys Gly Leu Glu Trp Val
        35                  40                  45

Gly Arg Ile Arg Asn Lys Thr Asn Asn Tyr Ala Thr Tyr Tyr Ala Asp
    50                  55                  60

Ser Val Lys Ala Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Ala Gly Asn Ser Phe Ala Tyr Trp Gly Gln Gly Thr Leu
            100                 105                 110

Val Thr Val Ser Ser
        115
```

<210> SEQ ID NO 39
<211> LENGTH: 113
<212> TYPE: PRT
<213> ORGANISM: Artificial Sequence
<220> FEATURE:
<223> OTHER INFORMATION: Artificial Sequence

<400> SEQUENCE: 39

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Tyr Pro Leu Thr Phe Gly Gln Gly Thr Lys Leu Glu Ile
            100                 105                 110

Lys
```

<210> SEQ ID NO 40
<211> LENGTH: 18
<212> TYPE: PRT
<213> ORGANISM: Artificial Sequence
<220> FEATURE:
<223> OTHER INFORMATION: Artificial Sequence

<400> SEQUENCE: 40

-continued

```
Gly Ser Thr Ser Gly Ser Gly Lys Pro Gly Ser Gly Glu Gly Ser Thr
1               5                   10                  15

Lys Gly

<210> SEQ ID NO 41
<211> LENGTH: 45
<212> TYPE: PRT
<213> ORGANISM: Artificial Sequence
<220> FEATURE:
<223> OTHER INFORMATION: Artificial Sequence

<400> SEQUENCE: 41

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 42
<211> LENGTH: 24
<212> TYPE: PRT
<213> ORGANISM: Artificial Sequence
<220> FEATURE:
<223> OTHER INFORMATION: Artificial Sequence

<400> SEQUENCE: 42

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 43
<211> LENGTH: 113
<212> TYPE: PRT
<213> ORGANISM: Artificial Sequence
<220> FEATURE:
<223> OTHER INFORMATION: Artificial Sequence

<400> SEQUENCE: 43

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
                20                  25                  30

Tyr Asp Val Leu Asp Lys Arg Arg Gly Arg Asp Pro Glu Met Gly Gly
            35                  40                  45

Lys Pro Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 44
<211> LENGTH: 41
<212> TYPE: PRT
<213> ORGANISM: Artificial Sequence
```

```
<220> FEATURE:
<223> OTHER INFORMATION: Artificial Sequence

<400> SEQUENCE: 44

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu
            35                  40

<210> SEQ ID NO 45
<211> LENGTH: 483
<212> TYPE: PRT
<213> ORGANISM: Artificial Sequence
<220> FEATURE:
<223> OTHER INFORMATION: Artificial Sequence

<400> SEQUENCE: 45

Glu Gln Lys Leu Ile Ser Glu Glu Asp Leu Asp Ile Val Met Thr Gln
1               5                   10                  15

Ser Pro Asp Ser Leu Ala Val Ser Leu Gly Glu Arg Ala Thr Ile Asn
            20                  25                  30

Cys Lys Ser Ser Gln Ser Leu Leu Tyr Ser Ser Asn Gln Lys Asn Tyr
        35                  40                  45

Leu Ala Trp Tyr Gln Gln Lys Pro Gly Gln Pro Pro Lys Leu Leu Ile
    50                  55                  60

Tyr Trp Ala Ser Ser Arg Glu Ser Gly Val Pro Asp Arg Phe Ser Gly
65                  70                  75                  80

Ser Gly Ser Gly Thr Asp Phe Thr Leu Thr Ile Ser Ser Leu Gln Ala
                85                  90                  95

Glu Asp Val Ala Val Tyr Tyr Cys Gln Gln Tyr Tyr Asn Tyr Pro Leu
            100                 105                 110

Thr Phe Gly Gln Gly Thr Lys Leu Glu Ile Lys Gly Ser Thr Ser Gly
        115                 120                 125

Ser Gly Lys Pro Gly Ser Gly Glu Gly Ser Thr Lys Gly Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Phe Thr Phe Asn Lys Asn Ala Met Asn
                165                 170                 175

Trp Val Arg Gln Ala Pro Gly Lys Gly Leu Glu Trp Val Gly Arg Ile
            180                 185                 190

Arg Asn Lys Thr Asn Asn Tyr Ala Thr Tyr Tyr Ala Asp Ser Val Lys
        195                 200                 205

Ala Arg Phe Thr Ile Ser Arg Asp Asp Ser Lys Asn Ser Leu Tyr Leu
    210                 215                 220

Gln Met Asn Ser Leu Lys Thr Glu Asp Thr Ala Val Tyr Tyr Cys Val
225                 230                 235                 240

Ala Gly Asn Ser Phe Ala Tyr Trp Gly Gln Gly Thr Leu Val Thr Val
                245                 250                 255

Ser Ser Gly Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
```

```
                290             295             300
Asp Ile Tyr Ile Trp Ala Pro Leu Ala Gly Thr Cys Gly Val Leu Leu
305                 310             315                 320

Leu Ser Leu Val Ile Thr Leu Tyr Cys Lys Arg Gly Arg Lys Lys Leu
                325             330             335

Leu Tyr Ile Phe Lys Gln Pro Phe Met Arg Pro Val Gln Thr Thr Gln
                340             345             350

Glu Glu Asp Gly Cys Ser Cys Arg Phe Pro Glu Glu Glu Glu Gly Gly
                355             360             365

Cys Glu Leu Arg Val Lys Phe Ser Arg Ser Ala Asp Ala Pro Ala Tyr
                370             375             380

Gln Gln Gly Gln Asn Gln Leu Tyr Asn Glu Leu Asn Leu Gly Arg Arg
385                 390             395                 400

Glu Glu Tyr Asp Val Leu Asp Lys Arg Arg Gly Arg Asp Pro Glu Met
                405             410             415

Gly Gly Lys Pro Arg Arg Lys Asn Pro Gln Glu Gly Leu Tyr Asn Glu
                420             425             430

Leu Gln Lys Asp Lys Met Ala Glu Ala Tyr Ser Glu Ile Gly Met Lys
                435             440             445

Gly Glu Arg Arg Arg Gly Lys Gly His Asp Gly Leu Tyr Gln Gly Leu
                450             455             460

Ser Thr Ala Thr Lys Asp Thr Tyr Asp Ala Leu His Met Gln Ala Leu
465                 470             475                 480

Pro Pro Arg

<210> SEQ ID NO 46
<211> LENGTH: 18
<212> TYPE: PRT
<213> ORGANISM: Artificial Sequence
<220> FEATURE:
<223> OTHER INFORMATION: Artificial Sequence

<400> SEQUENCE: 46

Glu Gly Arg Gly Ser Leu Leu Thr Cys Gly Asp Val Glu Glu Asn Pro
1               5                   10                  15

Gly Pro

<210> SEQ ID NO 47
<211> LENGTH: 688
<212> TYPE: PRT
<213> ORGANISM: Artificial Sequence
<220> FEATURE:
<223> OTHER INFORMATION: Artificial Sequence

<400> SEQUENCE: 47

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
                35                  40                  45

Pro Pro Lys Leu Leu Ile Tyr Trp Ala Ser Ser Arg Glu Ser Gly Val
                50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

```
Tyr Tyr Asn Tyr Pro Leu Thr Phe Gly Gln Gly Thr Lys Leu Glu Ile
            100                 105                 110

Lys Gly Ser Thr Ser Gly Ser Gly Lys Pro Gly Ser Gly Glu Gly Ser
            115                 120                 125

Thr Lys Gly Glu Val Gln Leu Val Glu Ser Gly Gly Gly Leu Val Gln
130                 135                 140

Pro Gly Gly Ser Leu Arg Leu Ser Cys Ala Ala Ser Gly Phe Thr Phe
145                 150                 155                 160

Asn Lys Asn Ala Met Asn Trp Val Arg Gln Ala Pro Gly Lys Gly Leu
                165                 170                 175

Glu Trp Val Gly Arg Ile Arg Asn Lys Thr Asn Asn Tyr Ala Thr Tyr
            180                 185                 190

Tyr Ala Asp Ser Val Lys Ala Arg Phe Thr Ile Ser Arg Asp Asp Ser
            195                 200                 205

Lys Asn Ser Leu Tyr Leu Gln Met Asn Ser Leu Lys Thr Glu Asp Thr
            210                 215                 220

Ala Val Tyr Tyr Cys Val Ala Gly Asn Ser Phe Ala Tyr Trp Gly Gln
225                 230                 235                 240

Gly Thr Leu Val Thr Val Ser Ser Gly Ser Thr Thr Thr Pro Ala Pro
                245                 250                 255

Arg Pro Pro Thr Pro Ala Pro Thr Ile Ala Ser Gln Pro Leu Ser Leu
            260                 265                 270

Arg Pro Glu Ala Cys Arg Pro Ala Ala Gly Gly Ala Val His Thr Arg
            275                 280                 285

Gly Leu Asp Phe Ala Cys Asp Ile Tyr Ile Trp Ala Pro Leu Ala Gly
            290                 295                 300

Thr Cys Gly Val Leu Leu Leu Ser Leu Val Ile Thr Leu Tyr Cys Lys
305                 310                 315                 320

Arg Gly Arg Lys Lys Leu Leu Tyr Ile Phe Lys Gln Pro Phe Met Arg
                325                 330                 335

Pro Val Gln Thr Thr Gln Glu Glu Asp Gly Cys Ser Cys Arg Phe Pro
            340                 345                 350

Glu Glu Glu Glu Gly Gly Cys Glu Leu Arg Val Lys Phe Ser Arg Ser
            355                 360                 365

Ala Asp Ala Pro Ala Tyr Gln Gln Gly Gln Asn Gln Leu Tyr Asn Glu
370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
            435                 440                 445

Gly Leu Tyr Gln Gly Leu Ser Thr Ala Thr Lys Asp Thr Tyr Asp Ala
450                 455                 460

Leu His Met Gln Ala Leu Pro Pro Arg Gly Ser Gly Glu Gly Arg Gly
465                 470                 475                 480

Ser Leu Leu Thr Cys Gly Asp Val Glu Glu Asn Pro Gly Pro Met Gly
                485                 490                 495

Arg Gly Leu Leu Arg Gly Leu Trp Pro Leu His Ile Val Leu Trp Thr
            500                 505                 510
```

Arg Ile Ala Ser Thr Ile Pro Pro His Val Gln Lys Ser Val Asn Asn
        515                 520                 525

Asp Met Ile Val Thr Asp Asn Asn Gly Ala Val Lys Phe Pro Gln Leu
    530                 535                 540

Cys Lys Phe Cys Asp Val Arg Phe Ser Thr Cys Asp Asn Gln Lys Ser
545                 550                 555                 560

Cys Met Ser Asn Cys Ser Ile Thr Ser Ile Cys Glu Lys Pro Gln Glu
            565                 570                 575

Val Cys Val Ala Val Trp Arg Lys Asn Asp Glu Asn Ile Thr Leu Glu
        580                 585                 590

Thr Val Cys His Asp Pro Lys Leu Pro Tyr His Asp Phe Ile Leu Glu
    595                 600                 605

Asp Ala Ala Ser Pro Lys Cys Ile Met Lys Glu Lys Lys Pro Gly
610                 615                 620

Glu Thr Phe Phe Met Cys Ser Cys Ser Ser Asp Glu Cys Asn Asp Asn
625                 630                 635                 640

Ile Ile Phe Ser Glu Glu Tyr Asn Thr Ser Asn Pro Asp Leu Leu
            645                 650                 655

Val Ile Phe Gln Val Thr Gly Ile Ser Leu Leu Pro Pro Leu Gly Val
        660                 665                 670

Ala Ile Ser Val Ile Ile Ile Phe Tyr Cys Tyr Arg Val Asn Arg Gln
    675                 680                 685

<210> SEQ ID NO 48
<211> LENGTH: 582
<212> TYPE: DNA
<213> ORGANISM: Artificial Sequence
<220> FEATURE:
<223> OTHER INFORMATION: Artificial Sequence

<400> SEQUENCE: 48
atgggcaggg gcctgctgag gggcctgtgg cccctgcaca tcgtgctgtg gaccaggatc      60
gccagcacca tccccccca cgtgcagaag agcgtgaaca cgacatgat cgtgaccgac       120 aacaacggcg ccgtgaagtt cccccagctg tgcaagttct gcgacgtgag gttcagcacc    180
tgcgacaacc agaagagctg catgagcaac tgcagcatca ccagcatctg cgagaagccc    240
caggaggtgt gcgtggccgt gtggaggaag aacgacgaga acatcaccct ggagaccgtg    300
tgccacgacc ccaagctgcc ctaccacgac ttcatcctgg aggacgccgc cagccccaag    360
tgcatcatga aggagaagaa gaagcccggc gagaccttct tcatgtgcag ctgcagcagc    420
gacgagtgca acgacaacat catcttcagc gaggagtaca acaccagcaa ccccgacctg    480
ctgctggtga tcttccaggt gaccggcatc agcctgctgc cccccctggg cgtggccatc    540
agcgtgatca tcatcttcta ctgctacagg gtgaacaggc ag                       582

<210> SEQ ID NO 49
<211> LENGTH: 1449
<212> TYPE: DNA
<213> ORGANISM: Artificial Sequence
<220> FEATURE:
<223> OTHER INFORMATION: Artificial Sequence

<400> SEQUENCE: 49
gagcagaagc tgatcagcga ggaggacctc gatatcgtga tgacccagag ccccgactct      60
ttagctgtgt ctttaggaga gagggccaca atcaactgca gagcagcca gagcctcctc     120 tacagcagca accagaagaa ctatttagct tggtaccagc aaaagcccgg ccagcccccc    180

| | |
|---|---|
| aagctgctga tctactgggc cagcagcaga gagagcggcg tgcccgatag attcagcgga | 240 |
| agcggctccg gcacagattt caccctcacc attagctctt tacaagctga ggacgtggcc | 300 |
| gtgtactact gccagcagta ctacaactac cctttaacct tcggccaagg taccaagctg | 360 |
| gagatcaagg gctccacatc cggatccggc aagcccggta gcggagaagg cagcacaaag | 420 |
| ggagaggtgc agctggtgga gagcggaggc ggactggtcc agcccggtgg atctttaagg | 480 |
| ctgtcttgtg ccgccagcgg ctttaccttt aacaagaacg ctatgaactg ggtgaggcaa | 540 |
| gctcccggta agggtttaga gtgggtgggt cgtattcgta ataagaccaa caactacgcc | 600 |
| acctactatg ccgactccgt gaaggctcgt ttcaccatct ctcgtgacga cagcaagaac | 660 |
| agcctctatt tacagatgaa ctctttaaag accgaggaca ccgccgtgta ctattgcgtg | 720 |
| gctggcaact ccttcgccta ctggggccaa ggcactttag tgaccgtgag ctccgggtcc | 780 |
| accacgacgc cagcgccgcg accaccaaca ccggcgccca ccatcgcgtc gcagcccctg | 840 |
| tccctgcgcc cagaggcgtg ccggccagcg gcggggggcg cagtgcacac gagggggctg | 900 |
| gacttcgcct gtgatatcta catctgggcg cccttggccg ggacttgtgg ggtccttctc | 960 |
| ctgtcactgg ttatcaccct ttactgcaaa cggggcagaa agaaactcct gtatatattc | 1020 |
| aaacaaccat ttatgagacc agtacaaact actcaagagg aagatggctg tagctgccga | 1080 |
| tttccagaag aagaagaagg aggatgtgaa ctgagagtga agttcagcag gagcgcagac | 1140 |
| gcccccgcgt accagcaggg ccagaaccag ctctataacg agctcaatct aggacgaaga | 1200 |
| gaggagtacg atgttttgga caagaggcgt ggccgggacc ctgagatggg gggaaagccg | 1260 |
| agaaggaaga accctcagga aggcctgtac aatgaactgc agaaagataa gatggcggag | 1320 |
| gcctacagtg agattgggat gaaaggcgag cgccggaggg caaggggca cgatggcctt | 1380 |
| taccagggtc tcagtacagc caccaaggac acctacgacg cccttcacat gcaggccctg | 1440 |
| ccccctcgc | 1449 |

<210> SEQ ID NO 50
<211> LENGTH: 2094
<212> TYPE: DNA
<213> ORGANISM: Artificial Sequence
<220> FEATURE:
<223> OTHER INFORMATION: Artificial Sequence

<400> SEQUENCE: 50

| | |
|---|---|
| gagcagaagc tgatcagcga ggaggacctc gatatcgtga tgacccagag ccccgactct | 60 |
| ttagctgtgt ctttaggaga gagggccaca atcaactgca agagcagcca gagcctcctc | 120 |
| tacagcagca accagaagaa ctatttagct tggtaccagc aaaagcccgg ccagcccccc | 180 |
| aagctgctga tctactgggc cagcagcaga gagagcggcg tgcccgatag attcagcgga | 240 |
| agcggctccg gcacagattt caccctcacc attagctctt tacaagctga ggacgtggcc | 300 |
| gtgtactact gccagcagta ctacaactac cctttaacct tcggccaagg taccaagctg | 360 |
| gagatcaagg gctccacatc cggatccggc aagcccggta gcggagaagg cagcacaaag | 420 |
| ggagaggtgc agctggtgga gagcggaggc ggactggtcc agcccggtgg atctttaagg | 480 |
| ctgtcttgtg ccgccagcgg ctttaccttt aacaagaacg ctatgaactg ggtgaggcaa | 540 |
| gctcccggta agggtttaga gtgggtgggt cgtattcgta ataagaccaa caactacgcc | 600 |
| acctactatg ccgactccgt gaaggctcgt ttcaccatct ctcgtgacga cagcaagaac | 660 |
| agcctctatt tacagatgaa ctctttaaag accgaggaca ccgccgtgta ctattgcgtg | 720 |
| gctggcaact ccttcgccta ctggggccaa ggcactttag tgaccgtgag ctccgggtcc | 780 |

| | | |
|---|---|---|
| accacgacgc cagcgccgcg accaccaaca ccggcgccca ccatcgcgtc gcagccctg | 840 | |
| tccctgcgcc cagaggcgtg ccggccagcg gcggggggcg cagtgcacac gaggggctg | 900 | |
| gacttcgcct gtgatatcta catctgggcg cccttggccg ggacttgtgg ggtccttctc | 960 | |
| ctgtcactgg ttatcaccct ttactgcaaa cggggcagaa agaaactcct gtatatattc | 1020 | |
| aaacaaccat ttatgagacc agtacaaact actcaagagg aagatggctg tagctgccga | 1080 | |
| tttccagaag aagaagaagg aggatgtgaa ctgagagtga agttcagcag gagcgcagac | 1140 | |
| gcccccgcgt accagcaggg ccagaaccag ctctataacg agctcaatct aggacgaaga | 1200 | |
| gaggagtacg atgttttgga caagaggcgt ggccgggacc ctgagatggg gggaaagccg | 1260 | |
| agaaggaaga accctcagga aggcctgtac aatgaactgc agaaagataa gatggcggag | 1320 | |
| gcctacagtg agattgggat gaaaggcgag cgccggaggg gcaaggggca cgatggcctt | 1380 | |
| taccagggtc tcagtacagc caccaaggac acctacgacg ccccttcacat gcaggccctg | 1440 | |
| cccccctcgcg gctctggaga gggcagaggc tctctgctga cctgcggcga cgtggaagag | 1500 | |
| aacccaggcc ccatgggaag aggtttactg agaggactgt ggcctttaca catcgtgctg | 1560 | |
| tggactcgta tcgccagcac catccccccc catgtgcaga agagcgtgaa caacgacatg | 1620 | |
| atcgtgaccg acaacaatgg cgccgtgaag ttcccccagc tgtgcaagtt ctgcgacgtg | 1680 | |
| aggttcagca cttgtgacaa ccagaagagc tgcatgagca actgcagcat cacctccatc | 1740 | |
| tgcgagaagc cccaagaagt gtgcgtggcc gtgtggagga agaacgacga gaacatcact | 1800 | |
| ttagagacag tgtgccacga ccccaagctg ccctaccacg acttcatttt agaagatgcc | 1860 | |
| gccagcccca agtgcatcat gaaggagaag aagaagcccg gcgagacctt cttcatgtgc | 1920 | |
| agctgcagct ccgacgagtg caacgataac atcatcttca gcgaggagta caacaccagc | 1980 | |
| aaccccgatt tactgctggt gatcttccaa gttaccggca tttctttact gcctcctttta | 2040 | |
| ggcgtggcta tcagcgtgat catcatcttc tactgctata gggtgaacag acag | 2094 | |

<210> SEQ ID NO 51
<211> LENGTH: 1419
<212> TYPE: DNA
<213> ORGANISM: Artificial Sequence
<220> FEATURE:
<223> OTHER INFORMATION: Artificial Sequence

<400> SEQUENCE: 51

| | | |
|---|---|---|
| gatatcgtga tgacccagag ccccgactct ttagctgtga gccttggaga gagggccaca | 60 | |
| atcaactgca gagcagcca gagcctcctc tacagcagca accagaagaa ctatttagct | 120 | |
| tggtaccagc aaaagcccgg ccagccccc aagctgctga tctactgggc cagcagcaga | 180 | |
| gagagcggcg tgcccgatag attcagcgga agcggctccg gcacagattt caccctcacc | 240 | |
| attagctctt tacaagctga ggacgtggcc gtgtactact gccagcagta ctacaactac | 300 | |
| cctttaacct tcggccaagg aacaaagctg gagatcaagg gctccacatc cggatccggc | 360 | |
| aagcccggta gcggagaagg cagcacaaag ggagaggtgc agctggtgga gagcggaggc | 420 | |
| ggactggtcc agcccggtgg atctttaagg ctgtcttgtg ccgccagcgg ctttaccttt | 480 | |
| aacaagaacg ctatgaactg ggtccgacaa gctcccggaa aaggtttaga gtgggtgggt | 540 | |
| cgtattcgta ataagaccaa caactacgcc acctactatg ccgactccgt gaaggctcgt | 600 | |
| ttcaccatct ctcgtgacga cagcaagaac agcctctatt tacaaatgaa ctcttttaaag | 660 | |
| accgaggaca ccgccgtgta ctattgcgtg gctggcaact ccttcgccta ctggggccaa | 720 | |

```
ggcactttag tgaccgtgag ctccgggtcc accacgacgc cagcgccgcg accaccaaca      780
ccggcgccca ccatcgcgtc gcaacccctg tccctgcgcc cgaggcgtg ccggccagcg       840 gcggggggcg cagtgcacac gagggggctg gacttcgcct gtgatatcta catctgggcg      900
cccttggccg ggacttgtgg ggtccttctc ctgtcactgg ttatcaccct ttattgcaaa      960
cggggcagaa agaaactcct gtatatattc aaacaaccat ttatgagacc agtacaaact     1020
actcaagagg aagatggctg tagctgccga tttccagaag aagaagaagg aggatgtgaa     1080
ttgagagtga agttcagcag gagcgcagac gcccccgcct atcagcaagg ccagaaccag     1140
ctctataacg agctcaattt agggcgaaga gaggagtacg atgttttgga caagaggcgt     1200
ggccgggacc ccgaaatggg gggaaagccg agaaggaaga accctcagga aggcttgtac     1260
aatgaattgc agaaggataa gatggcgag gcatacagtg agattgggat gaaaggcgag      1320
cgccggaggg gcaaggggca cgatggcctt tatcagggtc tcagtacagc caccaaggac     1380
acctacgacg cccttcacat gcaagccctg ccccctcgc                            1419

<210> SEQ ID NO 52
<211> LENGTH: 2064
<212> TYPE: DNA
<213> ORGANISM: Artificial Sequence
<220> FEATURE:
<223> OTHER INFORMATION: Artificial Sequence

<400> SEQUENCE: 52
gatatcgtga tgacccagag ccccgactct ttagctgtga gccttggaga gagggccaca      60
atcaactgca agagcagcca gagcctcctc tacagcagca accagaagaa ctatttagct     120
tggtaccagc aaaagcccgg ccagccccc aagctgctga tctactgggc cagcagaga       180 gagagcggcg tgcccgatag attcagcgga agcggctccg gcacagattt caccctcacc     240
attagctctt tacaagctga ggacgtggcc gtgtactact gccagcagta ctacaactac     300
cctttaacct tcggccaagg aacaaagctg gagatcaagg gctccacatc cggatccggc     360
aagcccggta gcggagaagg cagcacaaag ggagaggtgc agctggtgga gagcggaggc     420
ggactggtcc agcccggtgg atctttaagg ctgtcttgtg ccgccagcgg ctttaccttt     480
aacaagaacg ctatgaactg ggtccgacaa gctcccggaa aaggtttaga gtgggtgggt     540
cgtattcgta ataagaccaa caactacgcc acctactatg ccgactccgt gaaggctcgt     600
ttcaccatct ctcgtgacga cagcaagaac agcctctatt tacaaatgaa ctcttttaaag    660 accgaggaca ccgccgtgta ctattgcgtg gctggcaact ccttcgccta ctggggccaa     720
ggcactttag tgaccgtgag ctccgggtcc accacgacgc cagcgccgcg accaccaaca     780
ccggcgccca ccatcgcgtc gcaacccctg tccctgcgcc cgaggcgtg ccggccagcg      840 gcggggggcg cagtgcacac gagggggctg gacttcgcct gtgatatcta catctgggcg      900
cccttggccg ggacttgtgg ggtccttctc ctgtcactgg ttatcaccct ttattgcaaa     960
cggggcagaa agaaactcct gtatatattc aaacaaccat ttatgagacc agtacaaact    1020
actcaagagg aagatggctg tagctgccga tttccagaag aagaagaagg aggatgtgaa    1080
ttgagagtga agttcagcag gagcgcagac gcccccgcct atcagcaagg ccagaaccag    1140
ctctataacg agctcaattt agggcgaaga gaggagtacg atgttttgga caagaggcgt    1200
ggccgggacc ccgaaatggg gggaaagccg agaaggaaga accctcagga aggcttgtac    1260
aatgaattgc agaaggataa gatggcgag gcatacagtg agattgggat gaaaggcgag     1320
cgccggaggg gcaaggggca cgatggcctt tatcagggtc tcagtacagc caccaaggac    1380
```

-continued

| | |
|---|---|
| acctacgacg ccccttcacat gcaagccctg cccctcgcg gctctggaga gggcagaggc | 1440 |
| tctctgctga cctgcggcga cgtggaagag aacccaggcc ccatgggaag aggtttactg | 1500 |
| agaggactgt ggcctttaca catcgtgctg tggactcgta tcgccagcac catcccccc | 1560 |
| catgtccaaa agagcgtgaa caacgacatg atcgtgaccg acaacaatgg cgccgtgaag | 1620 |
| ttcccccagc tgtgcaagtt ctgcgacgtg aggttcagca cttgtgacaa ccagaagagc | 1680 |
| tgcatgagca actgcagcat cacctccatc tgcgagaagc ccaagaagt gtgcgtggcc | 1740 |
| gtgtggagga agaacgacga gaacatcact ttagagacag tgtgccacga ccccaagctg | 1800 |
| ccctaccacg acttcatttt agaagatgcc gccagcccca gtgcatcat gaggagaag | 1860 |
| aagaagcccg gcgagacctt cttcatgtgt tcttgttcgt ctgatgagtg caacgataac | 1920 |
| atcatcttca gcgaggagta caacaccagc aaccccgatt tactgctggt gatcttccaa | 1980 |
| gttaccggca tttcttact gcctccgttg ggcgtggcta tcagcgtgat catcatcttc | 2040 |
| tactgctatc gtgttaatcg tcaa | 2064 |

<210> SEQ ID NO 53
<211> LENGTH: 1476
<212> TYPE: DNA
<213> ORGANISM: Artificial Sequence
<220> FEATURE:
<223> OTHER INFORMATION: Artificial Sequence

<400> SEQUENCE: 53

| | |
|---|---|
| atgcttctcc tggtgacaag ccttctgctc tgtgagttac cacacccagc attcctcctg | 60 |
| atcccacata tggaggtgca gcttgttgag tctggtggag gattggtgca gcctggaggg | 120 |
| tcattgagac tctcatgtgc agcctctgga ttcaccttca ataagaatgc catgaattgg | 180 |
| gtccgccagg ctccaggaaa gggtttggaa tgggttggcc gcataagaaa taaaactaat | 240 |
| aattatgcaa catattatgc cgattcagtg aaagccaggt ttaccatctc cagagatgat | 300 |
| tcaaagaact cactctatct gcaaatgaac agcttgaaaa ccgaggacac agccgtgtac | 360 |
| tattgtgtgg ctggtaactc gttttgcttac tggggccaag ggactctggt cactgtctct | 420 |
| gcaggcggag gcggatcagg tggtggcgga tctgaggtg gcggaagcga cattgtgatg | 480 |
| acccagtctc cagactccct agctgtgtca ctgggagaga gggccactat caactgcaag | 540 |
| tccagtcaga gccttttata tagcagcaat caaaagaact acttggcctg gtaccaacag | 600 |
| aaaccagggc agcctcctaa actgctgatt tactgggcat ccagtaggga atctggggtc | 660 |
| cctgatcgct tcagtggcag tggatctggg acagatttca ctctcaccat cagcagtctg | 720 |
| caggctgaag acgtggcagt ttattactgt cagcaatatt ataactatcc gctcacgttc | 780 |
| ggtcagggga ccaagttgga gatcaaaact agtaccacga cgccagcgcc gcgaccacca | 840 |
| acaccggcgc ccaccatcgc gtcgcagccc ctgtccctgc gcccagaggc gtgccggcca | 900 |
| gcggcggggg gcgcagtgca cacgagggg ctggacttcg cctgtgacat ctacatctgg | 960 |
| gcgcccttgg ccgggacttg tggggtcctt ctcctgtcac tggttatcac caaacggggc | 1020 |
| agaaagaaac tcctgtatat attcaaacaa ccatttatga accagtaca aactactcaa | 1080 |
| gaggaagatg gctgtagctg ccgatttcca gaagaagaag aaggaggatg tgaactgaga | 1140 |
| gtgaagttca gcaggagcgc agacgccccc gcgtaccagc agggccagaa ccagctctat | 1200 |
| aacgagctca atctaggacg aagagaggag tacgatgttt tggacaagag acgtggccgg | 1260 |
| gaccctgaga tgggggggaaa gccgagaagg aagaaccctc aggaaggcct gtacaatgaa | 1320 |

```
ctgcagaaag ataagatggc ggaggcctac agtgagattg ggatgaaagg cgagcgccgg    1380
aggggcaagg ggcacgatgg cctttaccag ggtctcagta cagccaccaa ggacacctac    1440 gacgccttc acatgcaggc cctgccccct cgctga                               1476
```

<210> SEQ ID NO 54
<211> LENGTH: 1476
<212> TYPE: DNA
<213> ORGANISM: Artificial Sequence
<220> FEATURE:
<223> OTHER INFORMATION: Artificial Sequence

<400> SEQUENCE: 54

```
atgcttctcc tggtgacaag ccttctgctc tgcgaattac cacacccagc attcctcctg     60
atcccacata tggaggtgca gcttgttgag tctggtggag gattggtgca gcctggaggg    120
tcattgagac tctcatgtgc agcctctgga ttcaccttca ataagaatgc catgaattgg    180
gtccgccagg ctccaggaaa gggttttgaa tgggttggcc gcataagaaa taaaactaat    240
aattatgcaa catattatgc cgattcagtg aaagccaggt ttaccatctc cagagatgat    300
tcaaagaact cactctatct gcaaatgaac agcttgaaaa ccgaggacac agccgtgtac    360
tattgtgtgc tggaaaactc gtttgcttac tggggccaag ggactctggt cactgtcagc    420
gctggaggag gcggatcagg tggtggcgga tctggaggtg gcggaagcga cattgtgatg    480
acccagtctc cagactccct agctgtgtca ctggagaga gggccactat caactgcaag    540
tccagtcaga gccttttata tagcagcaat caaaagaact acttggcctg gtaccagcaa    600
aagccagggc agcctcctaa actgctgatt tactgggcat ccagtaggga atctggggtc    660
cctgatcgct tcagtggcag tggatctggg acagatttca ctctcaccat cagcagtctg    720
caggctgaag acgtggcagt ttattactgt cagcaatatt ataactatcc gctcacgttc    780
ggtcagggga ccaagttgga gatcaaaact agtaccacga cgccagcgcc gcgaccacca    840
acaccggcgc ccaccatcgc gagtcaacca ctgtccctga ggcctgaagc gtgccggcca    900
gcggcggggg gcgcagtgca cacgaggggg ctggacttcg cctgtgacat ctacatctgg    960
gcgcccttgg ccgggacttg tggggtcctt ctcctgtcac tggttatcac caaacggggc   1020
agaaagaaac tcctgtatat attcaaacaa ccatttatga ccagtaca aactactcaa    1080 gaggaagatg ctgtagctg ccgatttcca gaagaagaag aaggaggatg tgaactgaga   1140
gtgaagttca gcaggagcgc agacgccccc cgcgtaccagc aagggcagaa ccagctctat   1200
aacgagctca atctaggacg aagagaggag tacgatgttt tggacaagag gcgtggccgg   1260
gaccctgaga tgggggggaaa gccgagaagg aagaaccctc aggaaggcct gtacaatgaa   1320
ctgcagaaag ataagatggc ggaggcctac agtgagattg ggatgaaagg cgagcgccgg   1380
aggggcaagg ggcacgatgg cctttaccag ggtctcagta cagccaccaa ggacacctac   1440 gacgccttc acatgcaagc tctgccccct cgctga                               1476
```

<210> SEQ ID NO 55
<211> LENGTH: 2112
<212> TYPE: DNA
<213> ORGANISM: Artificial Sequence
<220> FEATURE:
<223> OTHER INFORMATION: Artificial Sequence

<400> SEQUENCE: 55

```
atgcttctcc tggtgacaag ccttctgctc tgtgagttac cacacccagc attcctcctg     60
atcccacata tggaggtgca gcttgttgag tctggtggag gattggtgca gcctggaggg    120
```

```
tcattgagac tctcatgtgc agcctctgga ttcaccttca ataagaatgc catgaattgg    180
gtccgccagg ctccaggaaa gggtttggaa tgggttggcc gcataagaaa taaaactaat    240
aattatgcaa catattatgc cgattcagtg aaagccaggt ttaccatctc cagagatgat    300
tcaaagaact cactctatct gcaaatgaac agcttgaaaa ccgaggacac agccgtgtac    360
tattgtgtgg ctggtaactc gtttgcttac tggggccaag ggactctggt cactgtctct    420
gcaggcggag gcggatcagg tggtggcgga tctggaggtg gcggaagcga cattgtgatg    480
acccagtctc cagactccct agctgtgtca ctgggagaga gggccactat caactgcaag    540
tccagtcaga gccttttata tagcagcaat caaaagaact acttggcctg gtaccaacag    600
aaaccagggc agcctcctaa actgctgatt tactgggcat ccagtaggga atctggggtc    660
cctgatcgct tcagtggcag tggatctggg acagatttca ctctcaccat cagcagtctg    720
caggctgaag acgtggcagt ttattactgt cagcaatatt ataactatcc gctcacgttc    780
ggtcagggga ccaagttgga gatcaaaact agtaccacga cgccagcgcc gcgaccacca    840
acaccggcgc ccaccatcgc gtcgcagccc ctgtccctgc gcccagaggc gtgccggcca    900
gcggcggggg gcgcagtgca cacgaggggg ctggacttcg cctgtgacat ctacatctgg    960
gcgcccttgg ccgggacttg tggggtcctt ctcctgtcac tggttatcac caaacggggc   1020
agaaagaaac tcctgtatat attcaaacaa ccatttatga ccagtaca aactactcaa     1080
gaggaagatg gctgtagctg ccgatttcca gaagaagaag aaggaggatg tgaactgaga   1140
gtgaagttca gcaggagcgc agacgccccc gcgtaccagc agggccagaa ccagctctat   1200
aacgagctca atctaggacg aagagaggag tacgatgttt tggacaagag acgtggccgg   1260
gaccctgaga tggggggaaa gccgagaagg aagaaccctc aggaaggcct gtacaatgaa   1320
ctgcagaaag ataagatggc ggaggcctac agtgagattg gatgaaagg cgagcgccgg    1380
aggggcaagg ggcacgatgg cctttaccag ggtctcagta cagccaccaa ggacacctac   1440
gacgcccttc acatgcaggc cctgccccct cgcgagggca gaggctctct gctgacctgc   1500
ggcgacgtgg aagagaaccc aggccccatg ggaagaggtt tactgagagg actgtggcct   1560
ttacacatcg tgctgtggac tcgtatcgcc agcaccatcc cccccatgt ccaaaagagc    1620
gtgaacaacg acatgatcgt gaccgacaac aatggcgccg tgaagttccc ccagctgtgc   1680
aagttctgcg acgtgaggtt cagcacttgt gacaaccaga gagctgcat gagcaactgc    1740
agcatcacct ccatctgcga gaagccccaa gaagtgtgcg tggccgtgtg gaggaagaac   1800
gacgagaaca tcactttaga cagtgtgtgc cacgacccca gctgcccta ccacgacttc    1860
attttagaag atgccgccag ccccaagtgc atcatgaagg agaagaagaa gcccggcgag   1920
accttcttca tgtgttcttg ttcgtctgat gagtgcaacg ataacatcat cttcagcgag   1980
gagtacaaca ccagcaaccc cgatttactg ctggtgatct tccaagttac cggcatttct   2040
ttactgcctc cgttgggcgt ggctatcagc gtgatcatca tcttctactg ctatcgtgtt   2100
aatcgtcaat ga                                                       2112

<210> SEQ ID NO 56
<211> LENGTH: 491
<212> TYPE: PRT
<213> ORGANISM: Artificial Sequence
<220> FEATURE:
<223> OTHER INFORMATION: Artificial Sequence

<400> SEQUENCE: 56
```

```
Met Leu Leu Leu Val Thr Ser Leu Leu Leu Cys Glu Leu Pro His Pro
1               5                   10                  15

Ala Phe Leu Leu Ile Pro His Met Glu Val Gln Leu Val Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Asn Lys Asn Ala Met Asn Trp Val Arg Gln Ala
    50                  55                  60

Pro Gly Lys Gly Leu Glu Trp Val Gly Arg Ile Arg Asn Lys Thr Asn
65                  70                  75                  80

Asn Tyr Ala Thr Tyr Tyr Ala Asp Ser Val Lys Ala Arg Phe Thr Ile
                85                  90                  95

Ser Arg Asp Asp Ser Lys Asn Ser Leu Tyr Leu Gln Met Asn Ser Leu
                100                 105                 110

Lys Thr Glu Asp Thr Ala Val Tyr Tyr Cys Val Ala Gly Asn Ser Phe
            115                 120                 125

Ala Tyr Trp Gly Gln Gly Thr Leu Val Thr Val Ser Ala Gly Gly Gly
        130                 135                 140

Gly Ser Gly Gly Gly Gly Ser Gly Gly Gly Gly Ser Asp Ile Val Met
145                 150                 155                 160

Thr Gln Ser Pro Asp Ser Leu Ala Val Ser Leu Gly Glu Arg Ala Thr
                165                 170                 175

Ile Asn Cys Lys Ser Ser Gln Ser Leu Leu Tyr Ser Ser Asn Gln Lys
                180                 185                 190

Asn Tyr Leu Ala Trp Tyr Gln Gln Lys Pro Gly Gln Pro Pro Lys Leu
        195                 200                 205

Leu Ile Tyr Trp Ala Ser Ser Arg Glu Ser Gly Val Pro Asp Arg Phe
    210                 215                 220

Ser Gly Ser Gly Ser Gly Thr Asp Phe Thr Leu Thr Ile Ser Ser Leu
225                 230                 235                 240

Gln Ala Glu Asp Val Ala Val Tyr Tyr Cys Gln Gln Tyr Tyr Asn Tyr
                245                 250                 255

Pro Leu Thr Phe Gly Gln Gly Thr Lys Leu Glu Ile Lys Thr Ser Thr
                260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
        290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
```

-continued

```
                420                 425                 430
Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 57
<211> LENGTH: 491
<212> TYPE: PRT
<213> ORGANISM: Artificial Sequence
<220> FEATURE:
<223> OTHER INFORMATION: Artificial Sequence

<400> SEQUENCE: 57

Met Leu Leu Leu Val Thr Ser Leu Leu Cys Glu Leu Pro His Pro
1               5                   10                  15

Ala Phe Leu Leu Ile Pro His Met Glu Val Gln Leu Val Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Asn Lys Asn Ala Met Asn Trp Val Arg Gln Ala
    50                  55                  60

Pro Gly Lys Gly Leu Glu Trp Val Gly Arg Ile Arg Asn Lys Thr Asn
65                  70                  75                  80

Asn Tyr Ala Thr Tyr Tyr Ala Asp Ser Val Lys Ala Arg Phe Thr Ile
                85                  90                  95

Ser Arg Asp Asp Ser Lys Asn Ser Leu Tyr Leu Gln Met Asn Ser Leu
            100                 105                 110

Lys Thr Glu Asp Thr Ala Val Tyr Tyr Cys Val Ala Gly Asn Ser Phe
        115                 120                 125

Ala Tyr Trp Gly Gln Gly Thr Leu Val Thr Val Ser Ala Gly Gly Gly
    130                 135                 140

Gly Ser Gly Gly Gly Gly Ser Gly Gly Gly Ser Asp Ile Val Met
145                 150                 155                 160

Thr Gln Ser Pro Asp Ser Leu Ala Val Ser Leu Gly Glu Arg Ala Thr
                165                 170                 175

Ile Asn Cys Lys Ser Ser Gln Ser Leu Leu Tyr Ser Ser Asn Gln Lys
            180                 185                 190

Asn Tyr Leu Ala Trp Tyr Gln Gln Lys Pro Gly Gln Pro Pro Lys Leu
        195                 200                 205

Leu Ile Tyr Trp Ala Ser Ser Arg Glu Ser Gly Val Pro Asp Arg Phe
    210                 215                 220

Ser Gly Ser Gly Ser Gly Thr Asp Phe Thr Leu Thr Ile Ser Ser Leu
225                 230                 235                 240

Gln Ala Glu Asp Val Ala Val Tyr Tyr Cys Gln Gln Tyr Tyr Asn Tyr
                245                 250                 255

Pro Leu Thr Phe Gly Gln Gly Thr Lys Leu Glu Ile Lys Thr Ser Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
```

```
                290                 295                 300
Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Ser Leu Val Ile
                325                 330                 335

Thr Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
                355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
                450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 58
<211> LENGTH: 491
<212> TYPE: PRT
<213> ORGANISM: Artificial Sequence
<220> FEATURE:
<223> OTHER INFORMATION: Artificial Sequence

<400> SEQUENCE: 58

Met Leu Leu Leu Val Thr Ser Leu Leu Leu Cys Glu Leu Pro His Pro
1               5                   10                  15

Ala Phe Leu Leu Ile Pro His Met Glu Val Gln Leu Val Glu Ser Gly
                20                  25                  30

Gly Gly Leu Val Gln Pro Gly Gly Ser Leu Arg Leu Ser Cys Ala Ala
                35                  40                  45

Ser Gly Phe Thr Phe Asn Lys Asn Ala Met Asn Trp Val Arg Gln Ala
        50                  55                  60

Pro Gly Lys Gly Leu Glu Trp Val Gly Arg Ile Arg Asn Lys Thr Asn
65                  70                  75                  80

Asn Tyr Ala Thr Tyr Tyr Ala Asp Ser Val Lys Ala Arg Phe Thr Ile
                85                  90                  95

Ser Arg Asp Asp Ser Lys Asn Ser Leu Tyr Leu Gln Met Asn Ser Leu
                100                 105                 110

Lys Thr Glu Asp Thr Ala Val Tyr Tyr Cys Val Ala Gly Asn Ser Phe
                115                 120                 125

Ala Tyr Trp Gly Gln Gly Thr Leu Val Thr Val Ser Ala Gly Gly Gly
        130                 135                 140

Gly Ser Gly Gly Gly Gly Ser Gly Gly Gly Ser Asp Ile Val Met
145                 150                 155                 160

Thr Gln Ser Pro Asp Ser Leu Ala Val Ser Leu Gly Glu Arg Ala Thr
```

```
                    165                 170                 175
Ile Asn Cys Lys Ser Ser Gln Ser Leu Leu Tyr Ser Ser Asn Gln Lys
            180                 185                 190

Asn Tyr Leu Ala Trp Tyr Gln Gln Lys Pro Gly Gln Pro Pro Lys Leu
            195                 200                 205

Leu Ile Tyr Trp Ala Ser Ser Arg Glu Ser Gly Val Pro Asp Arg Phe
            210                 215                 220

Ser Gly Ser Gly Ser Gly Thr Asp Phe Thr Leu Thr Ile Ser Ser Leu
225                 230                 235                 240

Gln Ala Glu Asp Val Ala Val Tyr Tyr Cys Gln Gln Tyr Tyr Asn Tyr
                245                 250                 255

Pro Leu Thr Phe Gly Gln Gly Thr Lys Leu Glu Ile Lys Thr Ser Thr
            260                 265                 270

Thr Thr Pro Ala Pro Arg Pro Pro Thr Pro Ala Pro Thr Ile Ala Ser
            275                 280                 285

Gln Pro Leu Ser Leu Arg Pro Glu Ala Cys Arg Pro Ala Ala Gly Gly
            290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
            355                 360                 365

Phe Pro Glu Glu Glu Glu Gly Gly Cys Glu Leu Arg Val Lys Phe Ser
            370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
            405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```